US006248724B1

(12) United States Patent
Moore et al.

(10) Patent No.: US 6,248,724 B1
(45) Date of Patent: Jun. 19, 2001

(54) ANTISENSE OLIGONUCLEOTIDE COMPOSITIONS TARGETED TO ANGIOTENSIN CONVERTING ENZYME MRNA AND METHODS OF USE

(75) Inventors: Mark D. Moore, Houston, TX (US); M. Ian Phillips; Dagmara Mohuczy, both of Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/162,484

(22) Filed: Sep. 25, 1998

Related U.S. Application Data

(60) Provisional application No. 60/059,661, filed on Sep. 25, 1997.

(51) Int. Cl.[7] .......................... A61K 31/70; A01N 43/04; C07H 21/04; C12Q 1/68; C12N 5/00

(52) U.S. Cl. ................. 514/44; 435/6; 435/91.1; 435/325; 435/375; 536/23.1; 536/24.3; 536/24.33; 536/24.5; 536/24.31

(58) Field of Search ............................. 514/44; 435/375, 435/91.1, 6, 325; 530/24.31; 536/23.1, 24.3, 24.5, 24.33

(56) References Cited

U.S. PATENT DOCUMENTS

| 5,561,041 | * | 10/1996 | Sidransky et al. | .................. 435/6 |
| 5,631,237 | * | 5/1997 | Dzau et al. | ...................... 514/44 |
| 5,663,188 | * | 9/1997 | Fossa | ............................ 514/44 |
| 5,726,019 | * | 3/1998 | Sidransky et al. | .................. 435/6 |

FOREIGN PATENT DOCUMENTS

| WO 91/00354 | | 1/1991 | (WO). |
| WO 91/17771 | | 11/1991 | (WO). |
| WO 94/02595 | | 2/1994 | (WO). |
| WO 95/30330 | | 11/1995 | (WO). |
| WO96/06951 | * | 3/1996 | (WO). |
| WO 97/33623 | | 9/1997 | (WO). |

OTHER PUBLICATIONS

Cushman and Ondetti, "Inhibitors of ACE for treatment of hypertension," *Biochem. Pharmacol.*, 19:1871, 1980.

Gyurko et al., "Time course of inhibition of hypertension by antisense oligonucleotides targeted to $AT_1$ angiotensin receptor mRNA in spontaneously hypertensive rats," *Am. J. Hypertens.*, 10:565–625, 1997.

Gyurko et al., "Antisense inhibition of $AT_1$ receptor mRNA and angiotensinogen mRNA in the brain of spontaneously hypertensive rats reduces hypertension of neurogenic origin," *Reg. Pep.*, 49(2):167–174, 1993.

Koike et al., "Angiotensin converting enzyme and genetic hypertension:cloning of rat cDNAs and characterization of the enzyme," *Biochem. Biophys. Res. Commun.*, 198(1):380–386, 1994.

Linz et al., "Long–term ACE inhibition doubles lifespan of hypertensive rats," *Circulation* 96(9):3164–3172, 1997.

Meng et al., "Antisense oligonucleotide to $AT_1$ receptor mRNA inhibits central angiotensin induced thirst and vasopressin," *Reg. Pep.*, 54:543–551, 1994.

Peris et al., "Antisense inhibition of striatal $GABA_A$ receptor proteins decreases GABA–stimulated chloride uptake and increases cocaine sensitivity in rats," *Mol. Brain Res.*, 57:310–312, 1998.

Phillips, "Antisense inhibition and adeno–associated viral vector delivery for reducing hypertension," *Hypertension*, 29(2):177–187, 1997.

Phillips et al., "Antisense inhibiiton of hypertension: a new strategy for renin–angiotensin candidate genes," *Kidney International*, 46:1554–1556, 1994.

Powell et al., "Inhibitors of angiotensin converting–enzyme prevent myointimal proliferation after vascular injury," *Science*, 245:186–188, 1989.

Wielbo et al., "Antisense inhibition of hypertension in the spontaneously hypertensive rat," *Hypertension*, 25(3):314–319, 1994.

Wielbo et al., "Inhibition of hypertension by peripheral administration of antisense oligodeoxynucleotides," *Hypertension*, 28(1):147–151, 1995.

Wieblo et al., "Antisense inhibition of angiotensinogen in hepatoma cell culture is enhanced by cationic liposome delivery," *Biochem. Biophy. Research Comm.*, 232:794–799, 1997.

Corey, "Peptide nucleic acids: expanding the scope of nucleic acid recognition," *TIBTECH*, 15:224–229, 1997.

International Search Report dated Apr. 7, 1999 (PCTUS98/20121) (4300.008710).

Morishita et al., "Antisense oligonucleotide inhibition of local angiotensin converting enzyme resulted in the inhibition of neointimal formation after vascular injury," *Circulation*, 90(4 Part 2):1–142, Abstract 0757, 1994.

Wang et al., "Long–term inhibition of angiotensin converting enzyme (ACE) activity by viral–mediated delivery of ACE antisense cDNA in rat pulmonmary endothelial cells (RPEC)," *Hypertension*, 32(10):627, Abstract P145, 1998.

Phillips et al., "Antisense Oligonucleotides: New Tools for Physiology," *News Physiol. Sci.* 12:99–105 (1997).

Mesmaeker et al., "Antisense Olignucleotides," *Acc. Chem. Res.* 28:366–374 (1995).

Andrea D. Branch, A good antisense molecule is hard to find, TIBS, 47–48, Feb. 1998.*

(List continued on next page.)

*Primary Examiner*—Robert A. Schwartzman
*Assistant Examiner*—Janet Epps
(74) *Attorney, Agent, or Firm*—Williams, Morgan & Amerson, P.C.

(57) ABSTRACT

Antisense oligonucleotides specific for mammalian ACE mRNA have been identified. Administration of these oligonucleotides to animals resulted in a decrease in blood pressure, but no significant change in heart rate. Methods for discovering other oligonucleotides with the same activity are taught, as are uses of the antisense molecules for treatment of human and animal diseases.

59 Claims, 1 Drawing Sheet

OTHER PUBLICATIONS

Figure 1:
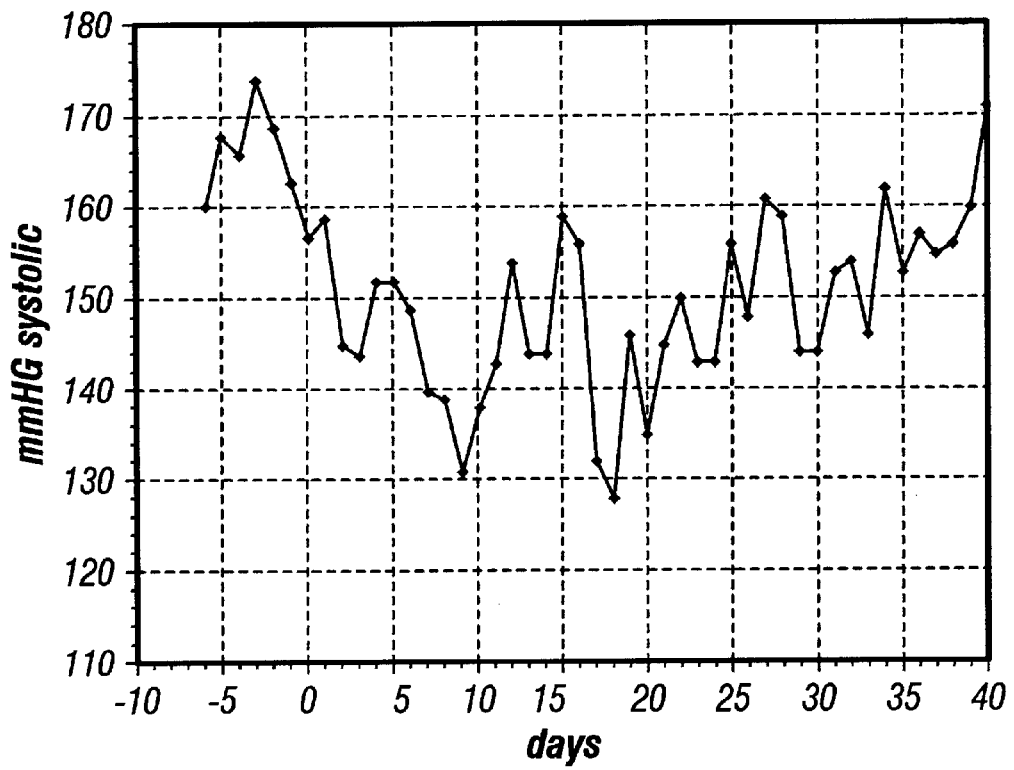

Trisha Gura, Antisense Has Growing Pains, Science, pp. 575–577, Oct. 1995.*

Stanley Crooke, Antisense '97: A rountable on the state of the industry, Nature Biotechnology, p. 522, Jun. 1997.*

Stanley Crooke, Antisense Research and Applications, Chapter 1, Basic Principles of Antisense Therapeutics, Springer–Verlag Press, Berlin, Heidelberg, New York, p. 3, Jul. 1998.*

Stuart H. Orkin, Report and Recommendations of the Panel to Assess the NIH Investment in Research on Gene Therapy, pp. 1–25, Dec. 1995.*

Donna Wielbo et al., Antisense Inhibition of Hypertension in the Spontaneously Hypertensive Rat, Hypertension, 25(3), pp. 314–319, Mar. 1995.*

* cited by examiner

SEQUENCE LISTING

```
<160> NUMBER OF SEQ ID NOS: 19

<210> SEQ ID NO 1
<211> LENGTH: 15
<212> TYPE: DNA
<213> ORGANISM: Artificial Sequence
```

```
<220> FEATURE:
<223> OTHER INFORMATION: Description of Artificial Sequence:
      oligonucleotide primer

<400> SEQUENCE: 1
cccccatggc gcggt                                                    15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 2
ccgcggaaaa gttgc                                                    15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3
gcaatccagg gtcaa                                                    15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4
cccccatgac gcggt                                                    15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
tgcgcggtgc tcggc                                                    15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6
cacgctctgg aacag                                                    15

<210> SEQ ID NO 7
<211> LENGTH: 42
<212> TYPE: DNA
<213> ORGANISM: Artificial Sequence
<220> FEATURE:
```

<223> OTHER INFORMATION: Description of Artificial Sequence:
      oligonucleotide primer

<400> SEQUENCE: 7
gctgctgctg ccgctgccgc tgctgttgct gctgccgccg ca                    42

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
cgatacggag acagatacat caacctcagg ggacccatcc                       40

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
ggtgcctttc ccagacaagc ccaacctcg                                   29

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 10
cacgcctcgg cttgggactt ctacaacagg aaagacttca ggatc                 45

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11
atctgtcctc ctgttacccg aaacgaaacc cactttgatg ctgg                  44

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 12
aggtggtgtg gaacgagtat gccgaggc                                    28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:

oligonucleotide primer

<400> SEQUENCE: 13
gcaaatagcc aaccacaccc tgaagtac                                              28

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 14
tgggagggct ggcgagacaa ggcggggaga gc                                         32

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 15
caacatctat gacttggtgg tgcccttccc ttcagccccc tcg                             43

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 16
aggctgatga tttcttcacc tccctggggc tgctgcc                                    37

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 17
cctgggactt ctacaacggc aaggacttcc                                            30

<210> SEQ ID NO 18
<211> LENGTH: 4024
<212> TYPE: DNA
<213> ORGANISM: Homo sapiens

<400> SEQUENCE: 18
gccgagcacc gcgcaccgcg tcatgggggc cgcctcgggc cgccggggc cggggctgct            60 gctgccgctg ccgctgctgt tgctgctgcc gccgcagccc gccctggcgt tggaccccgg          120
gctgcagccc ggcaactttt ctgctgacga ggcggggcg cagctcttcg cgcagagcta           180
caactccagc gccgaacagg tgctgttcca gagcgtggcc gccagctggg cgcacgacac          240
caacatcacc gcggagaatg caaggcgcca ggaggaagca gccctgctca gccaggagtt          300
tgcggaggcc tggggccaga aggccaagga gctgtatgaa ccgatctggc agaacttcac          360 ggaccccgcag ctgcgcagga tcatcggagc tgtgcgaacc ctgggctctg ccaacctgcc         420

-continued

```
cctggctaag cggcagcagt acaacgccct gctaagcaac atgagcagga tctactccac    480
cgccaaggtc tgcctcccca acaagactgc cacctgctgg tccctggacc cagatctcac    540
caacatcctg gcttcctcgc gaagctacgc catgctcctg tttgcctggg agggctggca    600
caacgctgcg ggcatcccgc tgaaaccgct gtacgaggat ttcactgccc tcagcaatga    660
agcctacaag caggacggct tcacacacac ggggggcctac tggcgctcct ggtacaactc    720
ccccaccttc gaggacgatc tggaacacct ctaccaacag ctagagcccc tctacctgaa    780
cctccatgcc ttcgtccgcc gcgcactgca tcgccgatac ggagacagat acatcaacct    840
caggggaccc atccctgctc atctgctggg agacatgtgg gcccagagct gggaaaacat    900
ctacgacatg gtggtgcctt cccagacaa gcccaacctc gatgtcacca gtactatgct    960
gcagcagggc tggaacgcca cgcacatgtt ccgggtggca gaggagttct tcacctccct   1020
ggagctctcc cccatgcctc ccgagttctg gaagggtcg atgctggaga agccggccga   1080
cgggcgggaa gtggtgtgcc acgcctcggc ttgggacttc tacaacagga aagacttcag   1140
gatcaagcag tgcacacggg tcacgatgga ccagctctcc acagtgcacc atgagatggg   1200
ccatatacag tactacctgc agtacaagga tctgccccgtc tccctgcgtc ggggggccaa   1260
ccccggcttc catgaggcca ttggggacgt gctggcgctc tcggtctcca ctcctgaaca   1320
tctgcacaaa atcggcctgc tggaccgtgt caccaatgac acggaaagtg acatcaatta   1380
cttgctaaaa atggcactgg aaaaaattgc cttcctgccc tttggctact ggtggacca    1440 gtggcgctgg ggggtctta gtgggcgtac ccccccttcc cgctacaact tcgactggtg   1500
gtatcttcga accaagtatc aggggatctg tcctcctgtt acccgaaacg aaacccactt   1560
tgatgctgga gctaagtttc atgttccaaa tgtgacacca tacatcaggt actttgtgag   1620
ttttgtcctg cagttccagt tccatgaagc cctgtgcaag gaggcaggct atgagggccc   1680
actgcaccag tgtgacatct accggtccac caaggcaggg gccaagctcc ggaaggtgct   1740
gcaggctggc tcctccaggc cctgcagga ggtgctgaag acatggtcg gcttagatgc    1800 cctggatgcc cagccgctgc tcaagtactt ccagccagtc acccagtggc tgcaggagca   1860
gaaccagcag aacggcgagg tcctgggctg gcccgagtac cagtggcacc cgccgttgcc   1920
tgacaactac ccggagggca tagacctggt gactgatgag gctgaggcca gcaagtttgt   1980
ggaggaatat gaccggacat cccaggtggt gtggaacgag tatgccgagg ccaactggaa   2040
ctacaacacc aacatcacca cagagaccag caagattctg ctgcagaaga acatgcaaat   2100
agccaaccac accctgaagt acggcaccca ggccaggaag tttgatgtga ccagttgca    2160 gaacaccact atcaagcgga tcataaagaa ggttcaggac ctagaacggg cagcgctgcc   2220
tgcccaggag ctggaggagt acaacaagat cctgttggat atggaaacca cctacagcgt   2280
ggccactgtg tgccacccga atggcagctg cctgcagctc gagccagatc tgacgaatgt   2340
gatggccaca tcccggaaat atgaagacct gttatgggca tgggagggct ggcgagacaa   2400 ggcgggggaga gccatcctcc agttttaccc gaaatacgtg gaactcatca accaggctgc   2460
ccggctcaat ggctatgtag atgcagggga ctcgtggagg tctatgtacg agacaccatc   2520
cctggagcaa gacctggagc ggctcttcca ggagctgcag ccactctacc tcaacctgca   2580
tgcctacgtg cgccgggccc tgcaccgtca ctacgggcc cagcacatca acctggaggg   2640
gcccattcct gctcacctgc tggggaacat gtgggcgcag acctggtcca acatctatga   2700
cttggtggtg cccttcccctt cagcccctc gatggacacc acagaggcta tgctaaagca   2760
```

-continued

| | |
|---|---|
| gggctggacg cccaggagga tgtttaagga ggctgatgat ttcttcacct ccctggggct | 2820 |
| gctgcccgtg cctcctgagt tctggaacaa gtcgatgctg gagaagccaa ccgacgggcg | 2880 |
| ggaggtggtc tgccacgcct cggcctggga cttctacaac ggcaaggact tccggatcaa | 2940 |
| gcagtgcacc accgtgaact tggaggacct ggtggtggcc caccacgaaa tgggccacat | 3000 |
| ccagtatttc atgcagtaca agacttacc tgtggccttg agggagggtg ccaaccccgg | 3060 |
| cttccatgag gccattgggg acgtgctagc cctctcagtg tctacgccca agcacctgca | 3120 |
| cagtctcaac ctgctgagca gtgagggtgg cagcgacgag catgacatca actttctgat | 3180 |
| gaagatggcc cttgacaaga tcgcctttat ccccttcagc tacctcgtcg atcagtggcg | 3240 |
| ctggagggta tttgatggaa gcatcaccaa ggagaactat aaccaggagt ggtgagcct | 3300 |
| caggctgaag taccagggcc tctgcccccc agtgcccagg actcaaggtg actttgaccc | 3360 |
| aggggccaag ttccacattc cttctagcgt gccttacatc aggtactttg tcagcttcat | 3420 |
| catccagttc cagttccacg aggcactgtg ccaggcagct ggccacacgg cccccctgca | 3480 |
| caagtgtgac atctaccagt ccaaggaggc cgggcagcgc ctggcgaccg ccatgaagct | 3540 |
| gggcttcagt aggccgtggc cggaagccat gcagctgatc acgggccagc ccaacatgag | 3600 |
| cgcctcggcc atgttgagct acttcaagcc gctgctggac tggctccgca cggagaacga | 3660 |
| gctgcatggg gagaagctgg gctggccgca gtacaactgg acgccgaact ccgctcgctc | 3720 |
| agaagggccc ctcccagaca gcggccgcgt cagcttcctg ggcctggacc tggatgcgca | 3780 |
| gcaggcccgc gtgggccagt ggctgctgct cttcctgggc atcgccctgc tggtagccac | 3840 |
| cctgggcctc agccagcggc tcttcagcat ccgccaccgc agcctccacc ggcactccca | 3900 |
| cgggcccag ttcggctccg aggtggagct gagacactcc tgaggtgacc cggctgggtc | 3960 |
| ggccctgccc aagggcctcc caccagagac tgggatggga acactggtgg gcagctgagg | 4020 |
| cggt | 4024 |

<210> SEQ ID NO 19
<211> LENGTH: 3942
<212> TYPE: DNA
<213> ORGANISM: Rattus norvegicus

<400> SEQUENCE: 19

| | |
|---|---|
| atgggggccg cgtccggcca gcgggggcgg tggccgttgt caccgccgct cttgatgctg | 60 |
| tcgctgctgc tgctgctgct gctgccgccg tcgcccgccc cggcgcttga ccctggattg | 120 |
| cagccgggca acttttccgc ggacgaggca ggggcgcagc tcttcgctga cagctataac | 180 |
| tcgagtgccg aggtggtgat gttccagagc accgcagcca gctgggcgca cgacaccaac | 240 |
| atcacggagg agaatgcgcg gctccaggag gaagcggccc tgatcaacca ggagtttgca | 300 |
| gaggtctggg gcaagaaggc caaggagctg tatgagtcca tctggcagaa cttcactgac | 360 |
| caaaagctgc gaaggatcat cggatccgta cagaccctag gacctgccaa cctgccctg | 420 |
| acccagcggc tgcagtacaa ctctctgcta agcaacatga gcagaatcta ctccaccggc | 480 |
| aaggtctgct tccccaacaa gactgccacc tgctggtccc tggacccaga gctcaccaac | 540 |
| atcctggctt cctcacgaaa ctatgccaag gtgctgtttg cctgggaagg ctggcatgat | 600 |
| gctgtgggta tcccactgag gcccctctat caggacttta ctgccctcag taatgaagcc | 660 |
| tacagacaag atggcttctc agacacagga gcctactggc gctcctggta tgagtccccc | 720 |
| tcctttgaag agagtttgga gcatctctac caccaagtcg agcccctcta cctgaacctc | 780 |
| catgcctttg tccgtcgcgc actgcaccgc cgctatgggg acaaatacat caatctcaga | 840 |

```
ggtcctattc ccgctcatct gctgggagat atgtgggcgc agagctggga gaacatttac      900
gacatggtag tgcctttccc ggacaaaccc aacctcgatg tcaccagtac aatggtacag      960
aagggctgga atgccacgca catgttccgg gtcgcagagg aattctttac ctcgctgggg     1020
ctctccccca tgcctccaga gttctgggcg gagtcgatgc tggagaaacc agctgatgga     1080
cgggaggtgg tgtgccatgc ctctgcgtgg gacttctaca acaggaagga cttcaggatt     1140
aagcagtgca cgcgggtcac gatggaccag ctgtccacag tacaccacga gatgggccac     1200
gtgcagtact atctccagta caaggacctg cacgtctctc tgcgtcgagg tgccaaccct     1260
ggcttccacg aggccatcgg ggatgtactc gctctctctg tctctacccc agcacatctg     1320
cacaaaattg gcctgctaga ccgtgttgcc aatgacatag aaagtgacat caattacttg     1380
ctaaagatgg ccctagagaa aattgccttc ttgcccttttg gttacctggt ggaccagtgg     1440
cgctgggggg tcttcagtgg acgtacccca ccctctcgct acaactacga ctggtggtat     1500
cttcgaacca agtatcaggg gatctgccca ccagttgctc ggaatgaaac ccattttgac     1560
gctggggcca agtttcacat cccaagcgtg acaccataca tcaggtactt tgtgagtttc     1620
gtgctacagt tccagttcca tcaagcgctg tgcaaggagg caggccacca gggtccacta     1680
caccagtgtg acatctacca gtccaccaag gcagggggcca agctccaaca ggtgctgcag     1740
gctggctgct ccaggccctg gcaggaggtg ctgaaggacc tggtgggttc agatgcgctg     1800
gatgccagtg cgctaatgga gtacttccaa ccagtaagcc agtggctgca ggagcagaat     1860
cagcggaatg gcgaggtcct aggctggccg gagtatcagt ggcgtccacc gttaccagac     1920
aactatccag agggaattga cctagagact gatgaagcca aggctaacag gttcgtggag     1980
gagtatgacc ggacagccaa ggtgttgtgg aacgaatacg cagaggccaa ctggcattat     2040
aacaccaaca ttaccataga gggcagcaag atcctgcttc agaaaaacaa ggaagtgtcc     2100
aaccatacct tgaaatatgg cacctgggcc aagacatttg acgtgagcaa cttccagaac     2160
tctaccatca agcggatcat aaagaaggtt cagaacgtgg accgggcagt gctgcctccc     2220
aacgagttag aagagtacaa ccagatcctg ctagacatgg agacgactta cagtgtagcc     2280 aatgttttgct acacaaatgg cacttgtctg tcactggagc ctgatctgac aaatataatg     2340
gccacgtccc ggaaatacga agaattgctt tgggtgtgga gagctggcg agacaaggtg     2400 gggagagcca tccttccctt ttttcccaaag tacgtggact ctccaacaa gatcgccaag     2460 ctcaacggct actctgatgc agggggattcc tggagatcct catatgagtc cgatgacttg     2520
gagcaagacc tggaaaaact ataccaggag ctgcagccgc tctacctgaa cctgcatgcc     2580
tatgtgcgcc gctccctgca ccgccattat gggtctgagt acatcaacct ggatggtccc     2640
attcctgccc acctgctagg gaacatgtgg gcacagactt ggtccaacat ctatgacttg     2700
gtggcaccct tcccttccgc ccccagtata gatgccacgg aggccatgat aaagcaggga     2760
tggacaccca aaggatatt taaggaagct gacaattttt ttacctcccct ggggctgtta     2820 cctgtgcccc ctgagttctg gaacaagtca atgttagaga agccaaccga tgggagggag     2880
gtggtgtgcc atgcctcagc ctgggacttc tacaacggca aggacttcag gatcaagcaa     2940
tgtacctctg tgaacatgga ggaattggtg atagcccacc acgaaatggg ccacatccag     3000
tatttcatgc agtacaaaga cttgcctgtg acctttcggg agggcgccaa ccccggtttt     3060
catgaggcta ttgagatgt ttttggctctg tctgtgtcta cacccaagca tctacacagt     3120
ctcaacctgc tcagcagtga gggcagtggc tacgagcatg acatcaactt tctaatgaag     3180
```

-continued

```
atggcccttg acaagatcgc cttcatcccc ttcagctacc tcattgacca gtggcgctgg    3240
agggtctttg acggaagcat caccaaggag aactacaacc aggagtggtg gagtctcaga    3300
ctgaagtacc agggtctctg ccctccagtg cctagatccc aaggtgactt tgacccaggg    3360
tccaagttcc acgttcctgc gaatgtgcca tacatcaggt actttatcag cttcatcatc    3420
cagttccagt tccacgaggc actatgtcgc gcagccgggc acaccggccc cctgtacaag    3480
tgtgatatct accaatccaa ggaagcaggg aagctgctgg cagatgccat gaagttgggc    3540
tacagtaagc agtggccaga agccatgaag ataatcacag gccaacctaa catgtcagcc    3600
tctgccatta tgaattactt caagccactg actgaatggc tcgtcacaga gaacaggaga    3660
catggagaga cactgggctg gccggagtac acctggacac caaacacggc tcgtgcagaa    3720
ggctccctcc cagagtccag tcgcgtcaac ttcctgggta tgtacctgga accacagcag    3780
gcccgtgtgg gccagtgggt gctgctcttc ctaggcgtcg ccctgctggt ggccaccgtg    3840
ggtctcgccc accgactcta caacatccat aaccatcaca gcctccgccg gccccaccgt    3900
gggccccagt ttgggtccga ggtggagctc agacactcct ga                      3942
```

ANTISENSE OLIGONUCLEOTIDE COMPOSITIONS TARGETED TO ANGIOTENSIN CONVERTING ENZYME MRNA AND METHODS OF USE

The present application claims priority under 35 USC 119(e) U.S. Provisional Patent Application Ser. No. 60/059,661 filed Sep. 25, 1997, the entire contents of which is specifically incorporated herein by reference in its entirety without disclaimer.

The United States Government has rights in this invention pursuant to Grant No. RO1-HL7334 from the National Institutes of Health.

1.0 BACKGROUND OF THE INVENTION 1.1 Field of the Invention

The present invention relates generally to the fields of cardiovascular disease and hypertension. More particularly, it concerns antisense oligonucleotide compounds that specifically bind to mRNA encoding a mammalian angiotensin converting enzyme (ACE) and inhibit its expression. Disclosed are antisense oligonucleotide and peptide nucleic acid compositions, pharmaceutical formulations thereof, and vectors encoding antisense oligonucleotides that specifically bind ACE mRNA and alter ACE expression in a host cell. Also disclosed are methods for making and using these antisense molecules, compositions, and vectors to reduce ACE activity, decrease translation of ACE-specific mRNA, and treat disorders in a mammal arising from elevated ACE expression, including hypertension.

1.2. Description of Related Art 1.2.1 Hypertension

Hypertension is the result of increased arterial resistance to blood flow and left untreated can lead to various pathological consequences. Hypertension affects approximately 40 million people in the United States. Heart attack (Nicholls et al., 1998), kidney damage (Agodoa, 1998), stroke (Chamorro et al., 1998) and loss of vision (Satllworth and Waldron, 1997) are typical conditions that result from high blood pressure. When blood vessels are subjected to high pressure for extended periods of time, they respond by thickening, vasospasm, and internal build-up of lipids and plaques, a condition known as arteriosclerosis. Arteriosclerosis further causes a decreased blood flow to the kidneys, which respond by releasing the protease renin. An overactive renin-angiotensin system is often implicated in the development of hypertension and cardiovascular disease (Nicholls et al., 1998).

Hypertension is often called the "silent killer," since half of the population afflicted with high blood pressure are unaware of the condition. Thus, an initial step in combating hypertension is early detection. Following diagnosis, actions must be taken to control the disorder. Diuretics, beta-adrenergic blockers, calcium channel blockers and ACE inhibitors are all commonly administered drugs used to treat hypertension. Each of these drugs has negative side effects associated with it, limiting their use in many situations. For example, the commonly prescribed ACE inhibitors captopril, enalapril and lisinopril have demonstrated a variety of adverse side effects such as cough, rash, fetal death, intra-uterine growth retardation, hypotension, acute renal failure and hepatotoxicity (Sadeck et al., 1997; Deira et al., 1997; Menefee et al., 1998). Further, the short lasting effect of these drugs requires a daily dose. Poor compliance is a major problem with drug regimens and can lead to a hypertensive crisis if the drug is not taken as scheduled.

1.2.2 The Renin-Angiotensin System (RAS)

Angiotensinogen (AGT), a protein produced mainly in the liver, is the substrate for the enzyme renin, produced by the kidneys. The action of renin on AGT is the formation of the decapeptide angiotensin I. Angiotensin I is hydrolyzed by angiotensin converting enzyme (ACE), yielding the octapeptide angiotensin II (Ang II). Ang II is considered to be one of the major contributors to hypertension (Alderman et al., 1991) and is also a growth stimulator of heart tissue and vascular smooth muscle cells (Dzau, 1993). Ang II is not only a potent vasoconstrictor and regulator of blood pressure, it may also result in cardiac hypertrophy and possibly play a role in arterial restenosis after angioplasty (Powell et al., 1989). Thus, through the inhibition of ACE, the production of Ang II can be effectively reduced, resulting in a decrease in hypertensive blood pressures and possibly other cardiovascular diseases attributed to excess Ang II production.

1.2.3 Treatments of Hypertension

Currently, four major categories of hypertensive drugs are administered to treat high blood pressure: (1) Diuretics, typically the drug of choice when the abnormal blood pressure is not very high, increase the rate at which the body eliminates urine and salt, resulting in decreased blood pressure by reducing volume (Moser, 1998); (2) β-adrenergic blockers, typically prescribed in combination with diuretics, lower blood pressure and heart rate (Rodgers, 1998); (3) Calcium channel blockers work by preventing the entry of calcium into cells, which reduces vasoconstriction (Rosenthal, 1993); (4) ACE inhibitors prevent the narrowing and constriction of blood vessels by blocking the production of the vasoconstrictive peptide angiotensin II, a product of ACE (Rosenthal, 1993).

1.2.4 Antisense Oligonucleotides

Antisense oligodeoxynucleotides (AS-ODNs) are single-stranded, short sequences of DNA (Cohen, 1989; De Mesmaeker et al., 1995) that are complementary to specific messenger RNA (mRNA). Since AS-ODNs hybridize with the mRNA, they prevent the targeted mRNA from expressing its polypeptide product in the cell.

AS-ODNs have previously been used for the treatment of hypertension (Phillips, 1997; Wielbo et al., 1994; Phillips et al., 1994 and Gyurko et al., 1997), using AS-ODNs targeted to AT-1 angiotensin receptor mRNA (Gyurko et al., 1993 and Meng et al., 1994) and angiotensinogen mRNA protein (Wielbo et al., 1997; Wielbo et al., 1996; Wielbo et al., 1995), that inhibit the synthesis of the AT-1 angiotensin receptor and angiotensinogen protein, respectively. The study by Phillips et al. (1994) confirmed that inhibition of the brain renin-angiotensin system in spontaneously hypertensive rats (SHR) lowers blood pressure, but this work did not extend to the other enzymes in the RAS, such as ACE.

1.3 Deficiencies in the Prior Art

Currently, the art does not provide pharmacological approaches to treating hypertension and abnormalities associated with ACE activity in a cell that avoids these and other problems associated with traditional ACE-inhibitor therapies. Thus, the need exists for an effective hypertensive treatment that circumvents the toxic side effects and provides more specific ACE inhibition with longer acting effects to improve patient compliance. In addition, methods for delivery of antisense oligonucleotides to a host cell, and in particular, non-invasive administration of ACE-specific antisense constructs to a mammal are particularly desirable.

SUMMARY OF THE INVENTION

The present invention overcomes these and other limitations in the prior art by providing antisense oligonucleotide and antisense peptide nucleic acid compositions to specifically inhibit ACE gene expression. The ACE-specific antisense compositions disclosed herein are useful in the identification of ACE-specific mRNAs in a biological sample, in the inhibition of ACE-specific mRNA translation, in the reduction of ACE polypeptide present in a cell, in the preparation of transgenic non-human animals having altered ACE activity, and in the treatment of hypertension in mammals, and in particular, humans using conventional and gene therapy methods for delivering such antisense constructs to an organism.

In a first embodiment, the invention provides antisense oligonucleotide and peptide nucleic acid compositions that specifically bind ACE mRNA in a mammalian cell, and alter the expression of ACE activity in the cell.

The present invention provides a composition comprising at least a first oligonucleotide of at least 9 to about 35 bases in length, wherein the oligonucleotide specifically binds to a portion of mRNA expressed from a gene encoding a mammalian angiotensin converting enzyme, and further wherein binding of the oligonucleotide to the mRNA is effective in decreasing the activity of the enzyme in a host cell expressing the mRNA.

In certain aspects of the invention, the oligonucleotide comprises deoxyribonucleic acid, ribonucleic acid, or peptide-nucleic acid. In particular embodiments, the oligonucleotide comprises a sequence of at least ten, at least eleven, at least twelve, at least thirteen or at least fourteen contiguous bases from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. In certain preferred embodiments, the oligonucleotide comprises the contiguous base sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

In other aspects of the present invention, the oligonucleotide has no more than 4, no more than 3, no more than 2, no more than 1 or no mismatches from the mRNA sequence to which it specifically binds.

In particular aspects of the invention, the composition further comprises at least a second oligonucleotide of at least 9 to about 35 nucleotides in length, wherein the second oligonucleotide specifically binds to a portion of mRNA expressed from a gene encoding angiotensin converting enzyme, AT-1 angiotensin receptor, or angiotensinogen.

In other aspects of the present invention, the composition further comprises at least a first anti-hypertensive agent. In particular embodiments, the anti-hypertensive agent is selected from the group consisting of captopril, enalapril, ramipril, cilazapril, fosinopril, and lisinopril. In certain preferred embodiments, the composition further comprises a pharmaceutically-acceptable vehicle, exemplified by, but not limited to, a liposome, a lipid particle, a lipid vesicle, a nanoparticle, a microparticle, a nanocapsule, a nanosphere, or a sphingosome.

In certain aspects of the invention, the enzyme is a human enzyme. In particular embodiments, the host cell is a mammalian host cell. In certain preferred embodiments of the invention, the host cell is a human cell. In other preferred aspects, the host cell is comprised within a human.

The present invention also provides a polynucleotide of at least 9 to about 35 bases in length, wherein the polynucleotide specifically binds to a portion of mRNA expressed from a DNA segment encoding a mammalian angiotensin converting enzyme, and further wherein binding of the polynucleotide to the mRNA is effective in decreasing the transcription of the mRNA in a host cell expressing the mRNA.

In particular aspects of the invention, the polynucleotide comprises at least 9 to about 30 bases in length, at least 9 to about 25 bases in length, at least 9 to about 20 bases in length or at least 9 to about 15 bases in length. In certain embodiments, the polynucleotide comprises at least 9 contiguous bases from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. In other aspects of the invention, the polynucleotide comprises DNA, RNA, or PNA.

The invention also provides a composition comprising an antisense oligomer of at least 9 to about 35 bases in length that specifically binds to an mRNA encoding a human angiotensin converting enzyme polypeptide, wherein binding of the oligomer to the mRNA is effective in reducing the translation of the mRNA into the polypeptide.

In certain embodiments of the invention, the antisense oligomer comprises at least a nine, at least a ten, at least an eleven, at least a twelve, at least a thirteen or at least a fourteen contiguous-base sequence from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. In certain preferred embodiments, the antisense oligomer comprises the continuous-base sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. In certain aspects of the invention, the antisense oligomer comprises DNA, RNA, or PNA.

The present invention further provides an antisense nucleic acid molecule comprising a segment complementary to a sequence unique to mammalian angiotensin converting enzyme-specific mRNA, wherein when administered to a living organism, the antisense molecule is capable of reducing the amount of the enzyme in the organism.

Additionally, the present invention provides a composition comprising at least a first antisense oligonucleotide specific for a mammalian ACE mRNA and at least a second antisense oligonucleotide specific for a mammalian renin, angiotensin, angiotensinogen, or AT-1 receptor mRNA.

In certain aspects of the invention, the second antisense oligonucleotide is specific for a mammalian angiotensinogen mRNA. In other aspects, the second antisense oligonucleotide is specific for an mRNA that encodes a transcriptional factor. In particular embodiments of the invention, the first antisense oligonucleotide or the second antisense oligonucleotide forms a stable homoduplex or heteroduplex with the mRNA. In yet other embodiments, the composition further comprises a pharmaceutically acceptable carrier. In further aspects, the first and the second oligonucleotides comprise a sequence region of at least 9 to about 35 bases in length.

Therapeutic combinations of two or more antisense oligonucleotides are also provided. At least one first antisense oligonucleotide specific for a mammalian ACE-encoding mRNA and at least one second antisense oligonucleotide specific for the same mRNA, or alternatively, an mRNA encoding another polypeptide in the RAS pathway are combined for treatment of hypertension. The second antisense oligonucleotide may be specific for, e.g., renin, angiotensin type 1 (AT-1) receptor, or angiotensinogen, or other gene involved in biochemical pathways involved in producing or regulating blood pressure and/or causing or contributing to hypertension in an animal. Alternatively, the constructs may even be specific for one or more particular transcription factor(s) that regulate one or more genes involved in producing hypertension in a mammal. Such combined therapy approached using two or more antisense oligonucleotides are particularly desirable where enhanced or synergistic activity towards treating hypertension is achieved.

The invention further provides a method for reducing expression of a gene encoding mammalian angiotensin converting enzyme in a host cell, the method comprising providing to the host cell an amount of a composition comprising an antisense oligomer of at least 9 to about 35 bases in length that specifically binds to an mRNA encoding the enzyme, effective to reduce expression of the gene in the cell.

Additionally, the invention provides a method for reducing the level of ACE activity in a cell, the method comprising introducing into the cell at least a first oligonucleotide of at least 9 to about 35 bases in length, wherein the oligonucleotide specifically binds to a portion of mRNA expressed from a gene encoding a mammalian angiotensin converting enzyme, and further wherein binding of the oligonucleotide to the mRNA is effective in decreasing the activity of the enzyme in a host cell expressing the mRNA, in an amount effective to reduce the level of the activity in the cell.

The invention also provides a method for decreasing hypertension in an animal, the method comprising administering to the animal an effective amount of at least a first antisense oligonucleotide of at least 9 to about 35 bases in length, wherein the oligonucleotide specifically binds to a portion of mRNA expressed from a gene encoding a mammalian angiotensin converting enzyme, and further wherein binding of the oligonucleotide to the mRNA is effective in decreasing the activity of the enzyme in a host cell expressing the mRNA.

The invention additionally provides a method for treating a disease associated with elevated ACE activity in a mammal, the method comprising administering to the animal an effective amount of at least a first oligonucleotide of at least 9 to about 35 bases in length, wherein the oligonucleotide specifically binds to a portion of mRNA expressed from a gene encoding a mammalian angiotensin converting enzyme, and further wherein binding of the oligonucleotide to the mRNA is effective in decreasing the activity of the enzyme in a host cell expressing the mRNA, such that a decrease in ACE activity is effected, thereby resulting in amelioration of the disease.

The invention also provides a method for treating hypertension, the method comprising administering to an animal in need thereof, an amount of at least a first oligonucleotide represented by the formula:

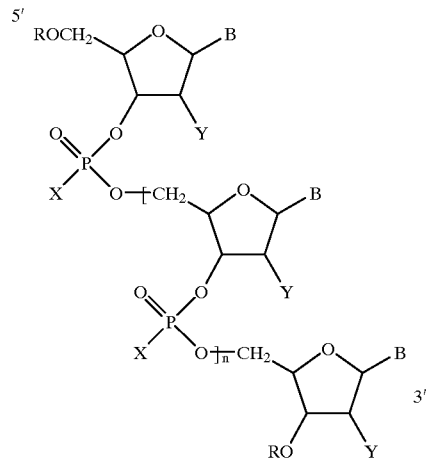

wherein each X independent y is O, S, or $C_{1-4}$ alkyl; each B independently is adenine, guanine, cytosine, or thymine selected such that the oligonucleotide binds to the sense mRNA strand coding for human angiotensin converting enzyme (ACE) when present to thereby inhibit the translation thereof; each R independently is H or $C_{1-4}$ alkyl or $PO_2$-substituted acridine; each Y is independently H or OH; and n is 7 to 33, and pharmaceutically-acceptable salts or hydrates of the oligonucleotide, effective to treat hypertension in the animal.

Furthermore, the invention provides a method for visualizing ACE mRNA in a cell, the method comprising: (i) labeling with a detectable label at least a first oligonucleotide of at least 9 to about 35 bases in length, wherein the oligonucleotide specifically binds to a portion of mRNA expressed from a gene encoding a mammalian angiotensin converting enzyme, and further wherein binding of the oligonucleotide to the mRNA is effective in decreasing the activity of the enzyme in a host cell expressing the mRNA; (ii) contacting the labeled oligonucleotide of (i) with RNA from the cell such that hybridization between the molecule and the RNA is effected; and (iii) visualizing label in the cell.

The invention also provides a therapeutic agent for treating a disease associated with an increase in ACE activity in an animal, the agent comprising an effective amount of a composition comprising at least a first oligonucleotide of at least 9 to about 35 bases in length, wherein the oligonucleotide specifically binds to a portion of mRNA expressed from a gene encoding a mammalian angiotensin converting enzyme, and further wherein binding of the oligonucleotide to the mRNA is effective in decreasing the activity of the enzyme in a host cell expressing the mRNA, in a pharmaceutically acceptable excipient.

The present invention further provides a method for preventing hypertension in a human comprising, administering to a subject an effective amount of at least a first oligonucleotide of at least 9 to about 35 bases in length, wherein the oligonucleotide specifically binds to a portion of mRNA expressed from a gene encoding a mammalian angiotensin converting enzyme, and further wherein binding of the oligonucleotide to the mRNA is effective in decreasing the activity of the enzyme in a host cell expressing the mRNA.

Further provides are kits for treating hypertension in a human comprising a device adapted for delivering atomized particles to the lungs, wherein the atomized particles contain at least a first oligonucleotide of at least 9 to about 35 bases in length, wherein the oligonucleotide specifically binds to a portion of mRNA expressed from a gene encoding a mammalian angiotensin converting enzyme, and further wherein binding of the oligonucleotide to the mRNA is effective in decreasing the activity of the enzyme in a host cell expressing the mRNA; and instructions for using the kit.

In addition to methods involving the delivery of exogenous oligonucleotide compositions to a host cell, or administration of such compositions to an animal in a therapeutic pharmaceutical formulation, the present invention also concerns gene therapy methods for introducing into a host cell a DNA construct that is transcribed by the cell machinery to give rise to an antisense RNA molecule that specifically binds to a portion of an mRNA encoding ACE polypeptide.

Regulation of expression of a gene encoding ACE in a mammalian cell genomes may also be achieved by integration of a gene under the transcription control of a promoter which is functional in the host and in which the transcribed strand of DNA is complementary to the strand of DNA that is transcribed from the endogenous ACE or RAS-related gene(s) one wishes to regulate. The integrated gene, referred to as an antisense gene, provides an RNA sequence capable of binding to naturally existing RNAs, exemplified by ACE mRNA, and inhibiting its expression, where the anti-sense sequence may bind to the coding, non-coding, or both, portions of the RNA. The antisense construction may be introduced into the animal cell in a variety of ways and be integrated into the animal genome for inducible or constitutive transcription of the antisense sequence.

The invention also provides an oligonucleotide represented by the formula:

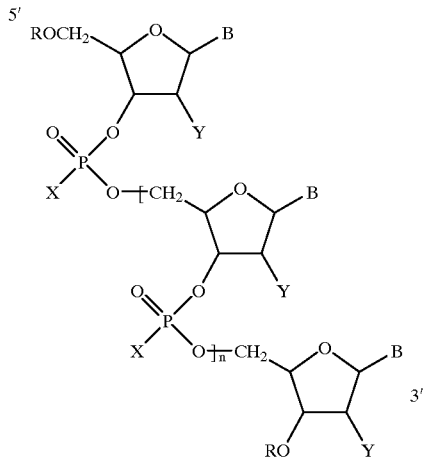

wherein each X independent y is O, S, or $C_{1-4}$ alkyl; each B independently is adenine, guanine, cytosine, or thymine selected such that the oligonucleotide binds to the sense mRNA strand coding for human angiotensin converting enzyme (ACE) when present to thereby inhibit the translation thereof; each R independently is H or $C_{1-4}$ alkyl or $PO_2$-substituted acridine; each Y is independently H or OH; and n is 7 to 33, and pharmaceutically-acceptable salts or hydrates of the oligonucleotide.

In particular preferred embodiments of the invention, B is selected such that the base sequence of the oligonucleotide comprises at least nine contiguous bases from one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

The compositions of the invention comprise one or more antisense oligonucleotides that are substantially complementary to, and that specifically bind to, mammalian ACE mRNA in vivo and in vitro and thus represent a new class of compounds that alter ACE activity by inhibiting ACE protein synthesis directly. These compounds function in sharp contrast to the mechanisms in which present drug treatment modalities for regulating ACE activity in a host cell which act by inhibit ACE protein function. The reduction or complete loss of protein translation by AS-ODNs results in a much longer biological lifetime than the synthetic drug treatments currently available, which require daily administration of the drug. The invention resides in the inhibition ACE expression in humans by administration of oligonucleotide compounds of Formula I:

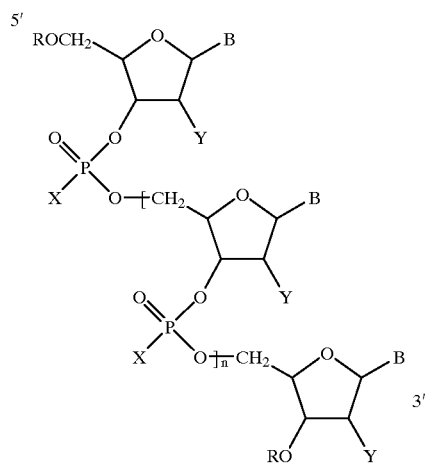

in which:

each X independently is O, S, or $C_{1-4}$ alkyl; each B independently is adenine, guanine, cytosine, or thymine selected such that the oligonucleotide binds to the sense mRNA strand coding for human angiotensin converting enzyme (ACE) to thereby inhibit the translation thereof; each R independently is H or $C_{1-4}$ alkyl or $PO_2$-substituted acridine; each Y independently is H or OH; and n is 9 to 25. The oligonucleotide compound of Formula I may also be a pharmaceutically-acceptable salt or hydrate thereof. Preferably, B is selected such that the base sequence of the oligonucleotide is according to at least nine contiguous bases from one of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

Another aspect of the invention provides a pharmaceutical composition useful for inhibiting expression of ACE comprising a pharmaceutical carrier and oligonucleotides of the above kind. The pharmaceutical carrier is preferably of the kind suitable for a nasal spray.

Another aspect of the invention provides a method for treating hypertension in a human comprising administering to a subject an effective amount of oligonucleotides or compositions of the above kind.

The objects of the present invention therefore include providing compounds, compositions and methods of the above kind that:

(a) avoid many of the side effects of conventional therapies;

(b) avoid invasive surgical procedures;

(c) are effective in lower, less frequent dosing regimens; and (d) specifically bind to ACE-specific mRNA.

2.2 Definitions

The term "ACE" refers to polypeptides having amino acid sequences which are substantially similar to the native mammalian angiotensin converting enzyme (dipeptidyl carboxypeptidase I; peptidyl-dipeptidase, peptidyl-dipeptidase precursor enzyme) amino acid sequences and which are biologically active in that they are capable of converting Ang I to Ang II, or cross-reacting with anti-ACE antibodies raised against an ACE polypeptide or peptide fragment thereof.

The term "ACE" also includes analogs of ACE molecules which exhibit at least some biological activity in common with native human ACE. Exemplary analogs of human ACE are disclosed in rabbit (GenBank X62551; Thellumkaa, 1992), mouse (GenBank J04946; Bernstein et al., 1989), rat (Koike et al., 1994), chicken (GenBank L40175; Esther et al., 1994), and fly (GenBank L43965; Wijffels, 1995). Furthermore, those skilled in the art of mutagenesis will appreciate that other analogs, as yet undisclosed or undiscovered, may be used to construct ACE analogs or ACE fusion proteins or identify ACE-related mRNAs and/or genes using well-known molecular biology techniques, including those described herein. Oligonucleotides complementary to ACE-mRNAs form the heart of the present invention, and oligonucleotides complementary to mammalian ACE-specific mRNAs, especially human ACE, are particularly preferred in the practice of the disclosed methods.

The oligonucleotides (or "ODNs" or "polynucleotides" or "oligos" or "oligomers" or "n-mers") of the present invention are preferably deoxyoligonucleotides (i.e. DNAs), or derivatives thereof; ribo-oligonucleotides (i.e. RNAs) or derivatives thereof; or peptide nucleic acids (PNAs) or derivatives thereof.

The term "substantially complementary," when used to define either amino acid or nucleic acid sequences, means that a particular subject sequence, for example, an oligonucleotide sequence, is substantially complementary to the sequence of ACE-specific sequences (e.g., those identified in SEQ ID NO:18 and SEQ ID NO:19), and thus will specifically bind to a portion of an mRNA encoding an ACE polypeptide. As such, typically the sequences will be highly complementary to the mRNA "target" sequence, and will have no more than 1, 2, 3, 4, 5, 6, 7, 8, 9, or 10 base mismatches throughout the sequence. In many instances, it may be desirable for the sequences to be exact matches, i.e. be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary oligonucleotide sequences will be greater than about 80 percent complementary (or '% exact-match') to the corresponding mRNA target sequence to which the oligonucleotide specifically binds, and will, more preferably be greater than about 85 percent complementary to the corresponding mRNA target sequence to which the oligonucleotide specifically binds. In certain aspects, as described above, it will be desirable to have even more substantially complementary oligonucleotide sequences for use in the practice of the invention, and in such instances, the oligonucleotide sequences will be greater than about 90 percent complementary to the corresponding mRNA target sequence to which the oligonucleotide specifically binds, and may in certain embodiments be greater than about 95 percent complementary to the corresponding mRNA target sequence to which the oligonucleotide specifically binds, and even up to and including 96%, 97%, 98%, 99%, and even 100% exact match complementary to the target mRNA to which the designed oligonucleotide specifically binds.

Percent similarity or percent complementary of any of the disclosed sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli*, will be free of glycan. Protein expressed in yeast may have a glycosylation pattern different from that expressed in mammalian cells.

"Biologically active," as used throughout the specification means that a particular molecule shares sufficient amino acid sequence similarity with the embodiments of the present invention disclosed herein to be capable of converting Ang I to Ang II, and/or specifically cross-react or bind specifically to one or more antibodies raised against a mammalian ACE polypeptide or peptide fragment thereof "DNA sequence" refers to a DNA polymer, in the form of a separate fragment or as a component of a larger DNA construct. Preferably, the DNA sequences are in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal untranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

"RNA sequence" refers to an RNA polymer, in the form of a separate fragment or as a component of a larger RNA construct, such as a messenger RNA (mRNA) encoding one or more ACE polypeptides. Preferably, the RNA sequences are in a quantity or concentration enabling identification, manipulation, and recovery of the sequence and its component nucleotide sequences by standard biochemical methods, for example, using a cloning vector, or alternatively, by chemically synthesizing the RNA molecule completely or partially in vitro.

"Nucleotide sequence" refers to a heteropolymer of deoxyribonucleotides, ribonucleotides, or peptide-nucleic acid sequences that may be assembled from smaller fragments, isolated from larger fragments, or chemically synthesized de novo or partially synthesized by combining shorter oligonucleotide linkers, or from a series of oligonucleotides, to provide a sequence which is capable of specifically binding to an mRNA molecule and acting as an antisense construct to alter, reduce, or inhibit the transcription of the message into polypeptide, and thus, ultimately affect the concentration, amount, or activity of the final gene product in situ, in vitro, or in vivo.

2.3 Exemplary Antisense Constructs for Human ACE-Specific mRNA

TABLE 1

PREFERRED OLIGONUCLEOTIDE BASE SEQUENCES TARGETED TO HUMAN ACE MRNA

| SEQ ID NO: | SEQUENCE | Base Postion in Human ACE Gene (SEQ ID NO:18) |
|---|---|---|
| SEQ ID NO:7 | GCTGCTGCTGCCGCTGCCGCTGCTGTTGCTGCTGCCGCCGCA | 55–96 |
| SEQ ID NO:8 | CGATACGGAGACAGATACATCAACCTCAGGGGACCCATCC | 815–854 |
| SEQ ID NO:9 | GGTGCCTTTCCCAGACAAGCCCAACCTCG | 913–941 |
| SEQ ID NO:10 | CACGCCTCGGCTTGGGACTTCTACAACAGGAAAGACTTCAGGATC | 1100–1144 |
| SEQ ID NO:11 | ATCTGTCCTCCTGTTACCCGAAACGAAACCCACTTTGATGCTGG | 1526–1569 |
| SEQ ID NO:12 | AGGTGGTGTGGAACGAGTATGCCGAGGC | 2004–2031 |
| SEQ ID NO:13 | GCAAATAGCCAACCACACCCTGAAGTAC | 2095–2122 |
| SEQ ID NO:14 | TGGGAGGGCTGGCGAGACAAGGCGGGAGAGC | 2381–2412 |
| SEQ ID NO:15 | CAACATCTATGACTTGGTGGTGCCCTTCCCTTCAGCCCCCTCG | 2689–2731 |
| SEQ ID NO:16 | AGGCTGATGATTTCTTCACCTCCCTGGGGCTGCTGCC | 2790–2826 |
| SEQ ID NO:17 | CCTGGGACTTCTACAACGGCAAGGACTTCC | 2904–2933 |

TABLE 2

PREFERRED HUMAN ACE MRNA-SPECIFIC 15-MER OLIGONUCLEOTIDES

| Beginning Oligo Position for each n-mer | $T_m$ | 3' dG | GC Clamp |
|---|---|---|---|
| 51 | 66.2 | −9.7 | −12.9 |
| 55 | 63.1 | −11.4 | −12.9 |
| 56 | 61.4 | −10.2 | −12.9 |
| 57 | 65.0 | −9.7 | −12.9 |
| 58 | 66.4 | −9.7 | −12.9 |
| 60 | 70.8 | −12.9 | −12.9 |
| 61 | 68.9 | −11.4 | −12.9 |
| 62 | 67.5 | −10.2 | −12.9 |
| 63 | 70.8 | −9.7 | −12.9 |
| 64 | 68.9 | −8.2 | −12.9 |
| 65 | 67.5 | −8.5 | −12.9 |
| 66 | 64.0 | −7.9 | −12.9 |
| 67 | 59.9 | −6.7 | −12.9 |
| 68 | 58.0 | −7.0 | −12.9 |
| 69 | 61.7 | −8.2 | −12.9 |
| 70 | 59.9 | −8.5 | −12.9 |
| 71 | 58.0 | −8.5 | −11.4 |
| 72 | 58.2 | −9.7 | −10.2 |
| 78 | 61.7 | −12.9 | −12.9 |
| 79 | 63.2 | −12.9 | −12.9 |
| 81 | 70.8 | −12.9 | −13.4 |
| 91 | 72.7 | −10.9 | −12.9 |
| 92 | 71.5 | −9.7 | −12.9 |
| 93 | 71.5 | −9.7 | −12.9 |
| 104 | 61.3 | −10.6 | −11.7 |
| 190 | 59.5 | −7.9 | −13.4 |
| 238 | 53.2 | −11.1 | −11.1 |
| 266 | 59.5 | −8.5 | −11.7 |
| 270 | 56.4 | −10.9 | −10.9 |
| 291 | 59.0 | −11.7 | −11.7 |
| 292 | 56.1 | −11.4 | −11.7 |
| 293 | 52.5 | −9.9 | −11.7 |
| 294 | 54.3 | −9.4 | −11.7 |
| 295 | 58.0 | −9.4 | −11.7 |
| 354 | 57.8 | −12.9 | −12.9 |
| 355 | 60.0 | −11.7 | −12.9 |
| 356 | 60.0 | −10.2 | −12.9 |
| 357 | 63.0 | −9.7 | −12.9 |
| 389 | 56.4 | −9.7 | −10.2 |
| 390 | 56.2 | −9.7 | −10.2 |
| 392 | 61.5 | −11.2 | −11.2 |
| 393 | 61.8 | −10.9 | −11.2 |
| 397 | 57.1 | −8.2 | −11.2 |
| 405 | 55.5 | −9.7 | −10.0 |
| 406 | 55.3 | −9.7 | −10.0 |
| 419 | 61.6 | −11.4 | −11.4 |

TABLE 2-continued

PREFERRED HUMAN ACE MRNA-SPECIFIC 15-MER OLIGONUCLEOTIDES

| Beginning Oligo Position for each n-mer | $T_m$ | 3' dG | GC Clamp |
|---|---|---|---|
| 420 | 61.8 | −12.9 | −12.9 |
| 427 | 51.7 | −5.8 | −12.9 |
| 470 | 50.5 | −12.9 | −12.9 |
| 471 | 52.9 | −11.7 | −12.9 |
| 472 | 53.0 | −10.0 | −12.9 |
| 473 | 53.0 | −8.5 | −12.9 |
| 474 | 57.9 | −8.5 | −12.9 |
| 476 | 58.6 | −7.6 | −12.9 |
| 477 | 57.9 | −7.6 | −12.9 |
| 478 | 56.2 | −6.4 | −12.9 |
| 479 | 58.1 | −8.2 | −12.9 |
| 480 | 61.8 | −9.7 | −12.9 |
| 487 | 57.6 | −10.0 | −11.2 |
| 488 | 53.6 | −8.2 | −11.2 |
| 489 | 55.8 | −7.0 | −11.2 |
| 490 | 55.8 | −7.0 | −11.2 |
| 491 | 55.8 | −6.7 | −11.2 |
| 492 | 54.7 | −7.0 | −11.2 |
| 497 | 51.7 | −9.7 | −10.0 |
| 498 | 49.6 | −10.0 | −10.0 |
| 499 | 45.1 | −9.4 | −10.0 |
| 500 | 47.5 | −9.4 | −10.0 |
| 501 | 46.7 | −7.9 | −10.0 |
| 502 | 48.9 | −7.9 | −10.0 |
| 503 | 51.2 | −9.7 | −10.0 |
| 504 | 50.5 | −8.2 | −10.0 |
| 505 | 52.2 | −8.5 | −10.0 |
| 572 | 51.7 | −10.0 | −10.0 |
| 573 | 52.4 | −9.7 | −10.0 |
| 574 | 52.4 | −9.7 | −10.0 |
| 575 | 52.2 | −9.7 | −10.0 |
| 576 | 55.8 | −9.7 | −10.0 |
| 577 | 55.8 | −9.7 | −10.0 |
| 585 | 63.5 | −9.7 | −10.9 |
| 592 | 62.8 | −9.9 | −10.9 |
| 593 | 59.4 | −9.6 | −10.0 |
| 594 | 57.7 | −10.2 | −10.2 |
| 599 | 64.1 | −12.9 | −12.9 |
| 601 | 63.7 | −9.6 | −12.9 |
| 602 | 62.6 | −8.1 | −12.9 |
| 603 | 65.3 | −8.1 | −12.9 |
| 618 | 56.6 | −7.9 | −11.4 |
| 619 | 50.2 | −5.8 | −11.4 |
| 636 | 50.4 | −11.2 | −11.2 |
| 637 | 50.4 | −10.9 | −11.2 |
| 665 | 53.2 | −11.1 | −11.1 |
| 713 | 50.9 | −9.4 | −12.4 |
| 714 | 52.4 | −7.9 | −12.4 |
| 715 | 53.5 | −7.9 | −12.4 |
| 716 | 52.4 | −8.2 | −12.4 |
| 786 | 61.4 | −12.9 | −12.9 |
| 788 | 68.0 | −12.9 | −13.4 |
| 832 | 51.2 | −10.9 | −10.9 |
| 833 | 50.0 | −10.9 | −10.9 |
| 834 | 50.2 | −9.1 | −10.9 |
| 835 | 53.4 | −9.1 | −10.9 |
| 837 | 56.4 | −9.4 | −10.9 |
| 838 | 56.1 | −9.6 | −10.9 |
| 839 | 53.1 | −8.1 | −10.9 |
| 920 | 54.7 | −10.9 | −10.9 |
| 921 | 55.8 | −11.2 | −11.2 |
| 922 | 55.8 | −10.0 | −11.2 |
| 923 | 51.7 | −8.2 | −11.2 |
| 924 | 51.7 | −8.2 | −11.2 |
| 925 | 50.0 | −7.9 | −11.2 |
| 926 | 50.6 | −7.6 | −11.2 |
| 972 | 61.0 | −8.2 | −11.7 |
| 973 | 56.7 | −6.6 | −11.7 |
| 992 | 58.3 | −7.9 | −11.1 |
| 993 | 52.9 | −7.6 | −10.0 |
| 994 | 49.9 | −6.4 | −10.0 |
| 995 | 46.5 | −6.4 | −10.0 |
| 996 | 47.0 | −6.4 | −10.0 |
| 1034 | 53.7 | −6.4 | −11.4 |
| 1035 | 54.3 | −6.4 | −11.4 |
| 1036 | 54.3 | −7.0 | −11.4 |
| 1037 | 54.1 | −8.2 | −11.4 |
| 1078 | 64.3 | −6.4 | −12.9 |
| 1079 | 61.6 | −6.7 | −12.9 |
| 1080 | 64.1 | −7.9 | −12.9 |
| 1081 | 64.1 | −7.6 | −12.9 |
| 1082 | 61.3 | −8.2 | −12.9 |
| 1083 | 57.6 | −7.6 | −12.9 |
| 1084 | 55.8 | −6.4 | −12.9 |
| 1085 | 55.8 | −8.2 | −11.4 |
| 1099 | 63.1 | −8.5 | −11.4 |
| 1100 | 63.1 | −8.5 | −11.4 |
| 1101 | 64.5 | −10.0 | −11.4 |
| 1102 | 65.5 | −9.7 | −11.4 |
| 1103 | 60.7 | −9.1 | −11.4 |
| 1104 | 57.2 | −7.6 | −11.4 |
| 1105 | 54.3 | −6.4 | −11.4 |
| 1106 | 55.0 | −6.4 | −11.4 |
| 1107 | 54.3 | −6.7 | −11.4 |
| 1108 | 47.9 | −6.1 | −10.0 |
| 1109 | 43.6 | −5.5 | −10.0 |
| 1110 | 41.0 | −5.8 | −10.0 |
| 1152 | 56.8 | −8.4 | −11.1 |
| 1153 | 52.1 | −8.0 | −11.1 |
| 1154 | 52.1 | −8.6 | −11.1 |
| 1155 | 56.4 | −8.1 | −11.1 |
| 1156 | 55.2 | −8.1 | −11.1 |
| 1157 | 55.2 | −7.9 | −11.1 |
| 1230 | 56.5 | −9.4 | −12.9 |
| 1231 | 57.2 | −9.4 | −12.9 |
| 1232 | 58.3 | −9.7 | −12.9 |
| 1233 | 62.0 | −9.7 | −12.9 |
| 1235 | 61.0 | −9.9 | −11.1 |
| 1236 | 58.2 | −9.6 | −10.2 |
| 1238 | 58.2 | −9.6 | −10.2 |
| 1354 | 46.0 | −7.0 | −10.2 |
| 1355 | 43.9 | −6.7 | −10.2 |
| 1356 | 44.7 | −6.7 | −10.2 |
| 1360 | 44.7 | −6.3 | −10.2 |
| 1361 | 43.5 | −6.3 | −10.2 |
| 1362 | 45.7 | −6.9 | −10.2 |
| 1384 | 45.9 | −7.9 | −10.0 |
| 1385 | 43.5 | −6.7 | −10.0 |
| 1386 | 47.3 | −7.9 | −10.0 |
| 1387 | 49.3 | −8.2 | −10.0 |
| 1388 | 49.3 | −8.5 | −10.0 |
| 1389 | 49.3 | −8.5 | −10.0 |
| 1390 | 49.3 | −7.3 | −10.0 |
| 1391 | 49.3 | −7.6 | −10.0 |
| 1407 | 58.0 | −10.9 | −11.2 |
| 1408 | 58.0 | −9.7 | −11.2 |
| 1409 | 57.0 | −8.5 | −11.2 |
| 1410 | 55.1 | −7.3 | −11.2 |
| 1411 | 55.1 | −8.8 | −11.2 |
| 1418 | 49.2 | −6.7 | −10.0 |
| 1419 | 49.2 | −8.5 | −10.0 |
| 1420 | 45.1 | −8.2 | −10.0 |
| 1421 | 46.7 | −8.2 | −10.0 |
| 1422 | 49.7 | −9.4 | −10.0 |
| 1450 | 50.4 | −7.9 | −12.4 |
| 1451 | 50.4 | −9.4 | −10.6 |
| 1452 | 50.6 | −11.2 | −11.2 |
| 1454 | 47.9 | −11.1 | −12.9 |
| 1455 | 46.9 | −9.0 | −12.9 |
| 1472 | 60.1 | −7.0 | −12.9 |
| 1473 | 58.6 | −5.8 | −12.9 |
| 1474 | 55.8 | −6.1 | −12.9 |
| 1475 | 52.0 | −6.4 | −12.9 |
| 1476 | 48.4 | −6.7 | −12.9 |
| 1477 | 49.1 | −6.7 | −12.9 |
| 1478 | 48.9 | −6.4 | −12.9 |

TABLE 2-continued

PREFERRED HUMAN ACE MRNA-SPECIFIC
15-MER OLIGONUCLEOTIDES

| Beginning Oligo Position for each n-mer | $T_m$ | 3' dG | GC Clamp |
|---|---|---|---|
| 1511 | 47.0 | −10.9 | −10.9 |
| 1512 | 48.0 | −10.9 | −10.9 |
| 1513 | 43.6 | −9.3 | −10.9 |
| 1532 | 51.7 | −11.4 | −11.4 |
| 1533 | 48.7 | −10.2 | −11.4 |
| 1534 | 49.4 | −9.0 | −11.4 |
| 1535 | 48.5 | −6.7 | −11.4 |
| 1537 | 50.4 | −8.4 | −11.4 |
| 1538 | 49.5 | −8.4 | −11.4 |
| 1539 | 50.6 | −9.0 | −11.4 |
| 1540 | 49.5 | −6.7 | −11.4 |
| 1541 | 54.4 | −8.2 | −11.4 |
| 1542 | 58.1 | −9.4 | −11.4 |
| 1543 | 56.4 | −9.4 | −10.2 |
| 1664 | 55.0 | −10.9 | −10.9 |
| 1707 | 61.4 | −10.9 | −10.9 |
| 1708 | 61.6 | −12.4 | −12.4 |
| 1784 | 47.4 | −5.7 | −11.4 |
| 1785 | 49.6 | −6.6 | −11.4 |
| 1786 | 51.8 | −8.1 | −11.4 |
| 1791 | 51.9 | −9.7 | −11.2 |
| 1792 | 48.6 | −8.2 | −11.2 |
| 1793 | 48.0 | −8.1 | −11.2 |
| 1794 | 48.9 | −8.1 | −11.2 |
| 1795 | 54.4 | −8.1 | −11.2 |
| 1796 | 57.9 | −9.6 | −11.2 |
| 1797 | 60.7 | −11.2 | −11.2 |
| 1862 | 55.2 | −11.1 | −11.1 |
| 1864 | 60.5 | −11.4 | −13.4 |
| 1865 | 57.0 | −9.9 | −13.4 |
| 1866 | 58.7 | −9.9 | −13.4 |
| 1867 | 58.4 | −7.6 | −13.4 |
| 1868 | 55.3 | −7.6 | −13.4 |
| 1869 | 57.1 | −9.1 | −13.4 |
| 1871 | 58.2 | −8.2 | −13.4 |
| 1875 | 60.1 | −10.9 | −11.2 |
| 1877 | 56.9 | −9.7 | −11.2 |
| 1878 | 59.9 | −9.7 | −11.2 |
| 1899 | 61.7 | −12.9 | −12.9 |
| 1932 | 54.5 | −7.6 | −11.2 |
| 2014 | 49.5 | −11.4 | −11.7 |
| 2015 | 49.0 | −9.9 | −11.7 |
| 2016 | 52.0 | −9.9 | −11.7 |
| 2030 | 44.2 | −5.2 | −10.0 |
| 2095 | 50.4 | −8.2 | −10.0 |
| 2096 | 46.1 | −7.6 | −10.0 |
| 2097 | 46.1 | −8.2 | −10.0 |
| 2098 | 44.8 | −6.4 | −10.0 |
| 2099 | 47.9 | −7.6 | −10.0 |
| 2100 | 52.2 | −9.4 | −10.0 |
| 2101 | 53.7 | −9.1 | −10.0 |
| 2102 | 55.5 | −9.7 | −10.0 |
| 2165 | 48.7 | −11.4 | −11.4 |
| 2166 | 49.6 | −11.4 | −11.4 |
| 2167 | 45.2 | −9.8 | −11.4 |
| 2266 | 47.8 | −9.6 | −10.2 |
| 2267 | 48.8 | −9.9 | −10.2 |
| 2288 | 55.1 | −8.6 | −11.4 |
| 2289 | 57.3 | −6.9 | −11.4 |
| 2365 | 47.2 | −11.2 | −11.2 |
| 2366 | 48.9 | −11.2 | −11.2 |
| 2367 | 47.8 | −9.6 | −11.2 |
| 2381 | 65.6 | −11.4 | −11.7 |
| 2382 | 63.7 | −9.9 | −11.7 |
| 2383 | 61.2 | −8.4 | −11.7 |
| 2384 | 57.4 | −6.1 | −11.7 |
| 2385 | 58.5 | −6.4 | −11.7 |
| 2386 | 59.1 | −6.7 | −11.7 |
| 2387 | 55.6 | −6.7 | −11.7 |
| 2388 | 55.6 | −8.5 | −11.7 |
| 2389 | 55.6 | −9.7 | −11.7 |
| 2391 | 62.0 | −12.9 | −12.9 |
| 2392 | 62.0 | −12.9 | −12.9 |
| 2393 | 61.9 | −12.9 | −12.9 |
| 2394 | 57.8 | −10.9 | −12.9 |
| 2395 | 57.2 | −9.4 | −12.9 |
| 2396 | 57.8 | −7.9 | −12.9 |
| 2397 | 57.2 | −6.4 | −12.9 |
| 2398 | 61.0 | −7.9 | −12.9 |
| 2402 | 60.5 | −8.1 | −12.9 |
| 2418 | 49.4 | −11.4 | −11.4 |
| 2419 | 49.6 | −10.2 | −11.4 |
| 2421 | 44.7 | −6.9 | −11.4 |
| 2422 | 43.2 | −6.3 | −11.4 |
| 2423 | 43.2 | −5.7 | −11.4 |
| 2448 | 58.9 | −11.2 | −11.2 |
| 2462 | 52.7 | −7.2 | −11.4 |
| 2483 | 58.0 | −9.9 | −10.9 |
| 2484 | 54.8 | −7.9 | −10.9 |
| 2485 | 53.0 | −8.2 | −10.9 |
| 2486 | 56.6 | −9.4 | −10.9 |
| 2528 | 55.4 | −11.4 | −11.4 |
| 2529 | 57.3 | −12.9 | −12.9 |
| 2618 | 52.3 | −6.7 | −11.2 |
| 2641 | 55.7 | −8.2 | −11.2 |
| 2656 | 54.5 | −6.6 | −11.2 |
| 2699 | 54.3 | −11.2 | −11.2 |
| 2700 | 53.7 | −10.9 | −11.2 |
| 2701 | 54.8 | −9.7 | −11.2 |
| 2702 | 55.4 | −8.2 | −11.2 |
| 2703 | 58.3 | −8.2 | −11.2 |
| 2704 | 60.0 | −9.7 | −11.2 |
| 2705 | 56.5 | −9.4 | −11.2 |
| 2706 | 57.5 | −9.7 | −11.2 |
| 2707 | 56.4 | −8.2 | −11.2 |
| 2708 | 54.7 | −7.0 | −11.2 |
| 2709 | 55.1 | −7.0 | −11.2 |
| 2710 | 57.0 | −8.2 | −10.9 |
| 2712 | 56.8 | −10.9 | −10.9 |
| 2713 | 56.8 | −12.4 | −12.4 |
| 2714 | 60.1 | −12.4 | −12.4 |
| 2715 | 59.5 | −10.9 | −12.4 |
| 2716 | 59.5 | −9.4 | −12.4 |
| 2755 | 54.2 | −7.9 | −10.9 |
| 2757 | 61.4 | −9.6 | −10.9 |
| 2769 | 57.6 | −6.3 | −12.9 |
| 2770 | 53.4 | −6.6 | −11.2 |
| 2805 | 60.4 | −12.4 | −12.4 |
| 2806 | 59.7 | −10.9 | −12.4 |
| 2807 | 59.7 | −9.7 | −12.4 |
| 2808 | 63.5 | −9.7 | −12.4 |
| 2809 | 60.2 | −8.2 | −12.4 |
| 2810 | 62.0 | −8.5 | −12.4 |
| 2811 | 64.7 | −9.7 | −12.4 |
| 2821 | 64.7 | −9.4 | −12.9 |
| 2822 | 61.2 | −7.9 | −12.9 |
| 2823 | 63.1 | −8.2 | −12.9 |
| 2824 | 62.0 | −8.2 | −12.9 |
| 2825 | 58.3 | −6.7 | −11.1 |
| 2860 | 55.0 | −9.6 | −10.0 |
| 2864 | 61.4 | −11.1 | −11.1 |
| 2872 | 66.9 | −7.6 | −12.9 |
| 2873 | 64.3 | −7.9 | −12.9 |
| 2874 | 66.7 | −9.4 | −12.9 |
| 2875 | 66.7 | −7.6 | −12.9 |
| 2876 | 63.0 | −7.9 | −12.9 |
| 2877 | 59.6 | −7.6 | −12.9 |
| 2878 | 58.0 | −6.4 | −12.9 |
| 2879 | 58.0 | −8.2 | −11.4 |
| 2909 | 44.6 | −11.1 | −11.1 |
| 2910 | 45.7 | −11.7 | −11.7 |
| 2911 | 47.0 | −10.0 | −11.7 |
| 2912 | 47.0 | −8.5 | −11.7 |
| 2913 | 50.0 | −8.5 | −11.7 |
| 2914 | 50.0 | −8.2 | −11.7 |
| 2915 | 49.6 | −7.6 | −11.7 |

TABLE 2-continued

PREFERRED HUMAN ACE MRNA-SPECIFIC 15-MER OLIGONUCLEOTIDES

| Beginning Oligo Position for each n-mer | $T_m$ | 3' dG | GC Clamp |
|---|---|---|---|
| 2916 | 51.0 | −7.6 | −11.7 |
| 2917 | 52.2 | −6.4 | −11.7 |
| 2918 | 51.1 | −6.4 | −11.7 |
| 3087 | 43.6 | −6.1 | −10.9 |
| 3088 | 45.7 | −6.1 | −10.9 |
| 3089 | 45.7 | −6.4 | −10.9 |
| 3094 | 44.6 | −11.1 | −11.1 |
| 3095 | 48.6 | −12.9 | −12.9 |
| 3096 | 49.8 | −11.2 | −12.9 |
| 3097 | 48.8 | −10.0 | −12.9 |
| 3098 | 48.8 | −8.5 | −12.9 |
| 3099 | 53.2 | −8.5 | −12.9 |
| 3100 | 53.2 | −8.5 | −12.9 |
| 3101 | 53.2 | −7.9 | −12.9 |
| 3102 | 56.1 | −9.4 | −12.9 |
| 3103 | 56.1 | −7.9 | −12.9 |
| 3104 | 59.2 | −7.9 | −12.9 |
| 3138 | 56.1 | −10.0 | −10.0 |
| 3143 | 58.1 | −9.6 | −10.2 |
| 3145 | 63.0 | −8.1 | −10.2 |
| 3146 | 59.5 | −8.1 | −10.2 |
| 3147 | 59.7 | −9.9 | −10.2 |
| 3148 | 62.0 | −8.2 | −10.2 |
| 3149 | 59.4 | −8.1 | −10.2 |
| 3200 | 53.9 | −10.9 | −11.4 |
| 3201 | 54.5 | −10.9 | −11.4 |
| 3202 | 54.6 | −9.7 | −11.4 |
| 3203 | 50.4 | −8.2 | −10.9 |
| 3204 | 48.3 | −7.0 | −10.9 |
| 3205 | 44.6 | −7.0 | −10.9 |
| 3206 | 48.5 | −8.2 | −10.9 |
| 3239 | 51.8 | −6.3 | −10.2 |
| 3326 | 64.1 | −9.7 | −12.4 |
| 3327 | 61.5 | −8.2 | −11.2 |
| 3328 | 57.7 | −7.6 | −11.2 |
| 3329 | 54.0 | −7.6 | −11.2 |
| 3330 | 50.8 | −6.1 | −11.2 |
| 3331 | 50.8 | −6.4 | −11.2 |
| 3332 | 51.6 | −7.0 | −11.2 |
| 3333 | 52.0 | −7.0 | −11.2 |
| 3334 | 54.0 | −8.5 | −11.2 |
| 3352 | 57.5 | −12.4 | −12.4 |
| 3365 | 48.1 | −6.6 | −10.0 |
| 3620 | 50.6 | −10.2 | −12.9 |
| 3621 | 55.8 | −9.7 | −12.9 |
| 3628 | 59.8 | −6.4 | −12.9 |
| 3629 | 59.6 | −7.9 | −11.4 |
| 3630 | 59.8 | −9.7 | −10.2 |
| 3694 | 57.1 | −10.2 | −13.4 |
| 3695 | 55.0 | −8.4 | −13.4 |
| 3696 | 54.3 | −6.4 | −13.4 |
| 3697 | 55.3 | −6.4 | −13.4 |
| 3700 | 62.0 | −11.4 | −13.4 |
| 3701 | 61.3 | −11.4 | −13.4 |
| 3702 | 62.3 | −9.9 | −13.4 |
| 3706 | 54.8 | −9.9 | −11.4 |
| 3707 | 55.9 | −8.2 | −11.4 |
| 3708 | 55.2 | −6.7 | −11.4 |
| 3709 | 56.3 | −6.7 | −11.4 |
| 3710 | 56.9 | −7.0 | −11.4 |
| 3711 | 56.3 | −6.7 | −11.4 |
| 3714 | 54.9 | −10.9 | −10.9 |
| 3728 | 56.9 | −7.9 | −10.9 |
| 3730 | 58.3 | −11.4 | −11.4 |
| 3731 | 58.5 | −12.9 | −12.9 |
| 3808 | 53.9 | −9.6 | −11.2 |
| 3809 | 50.7 | −8.1 | −11.2 |
| 3811 | 58.8 | −9.8 | −11.2 |
| 3822 | 56.4 | −7.0 | −12.9 |
| 3824 | 58.1 | −8.8 | −10.9 |
| 3868 | 63.7 | −10.2 | −12.9 |
| 3869 | 65.3 | −9.7 | −12.9 |
| 3871 | 68.3 | −9.4 | −12.9 |
| 3872 | 66.0 | −9.4 | −11.7 |
| 3873 | 64.7 | −9.4 | −11.7 |
| 3874 | 63.1 | −8.2 | −11.7 |
| 3875 | 59.3 | −7.9 | −11.7 |
| 3876 | 60.9 | −9.4 | −11.7 |
| 3891 | 64.2 | −12.9 | −12.9 |
| 3905 | 60.5 | −9.4 | −11.4 |
| 3998 | 54.3 | −11.2 | −11.2 |
| 3999 | 52.3 | −11.2 | −11.2 |
| 4000 | 51.7 | −9.7 | −11.2 |
| 4001 | 55.0 | −9.7 | |

Oligo position refers to the starting base position corresponding to the human ACE sequence for each of the indicated 15-mers. For example, the first oligonucleotide begins at base position 51 in the sequence and extends until position 65. The last indicated oligonucleotide begins at base 4001 in the human ACE sequence and continues until position 4015 in the sequence. In addition to the indicated 15-mers, smaller internal n-mers from 9 bases in length up to the fill length 15-mer are also contemplated to be useful in the practice of the present invention. For example, in addition to the first indicated 15-mer (extending from position 51 to 65), the internal 14-mers (extending from position 51 to 64 or from position 52–65) are also considered to fall within the scope of this disclosure, as are all internal 13-mers, all 12-mers, 11-mers, 10-mers, and 9-mers of each of the disclosed 15-mers.

TABLE 3

PREFERRED HUMAN ACE MRNA-SPECIFIC 25-MER OLIGONUCLEOTIDES

| Beginning Oligo Position for each n-mer | $T_m$ | 3' dG | GC Clamp |
|---|---|---|---|
| 55 | 90.6 | −8.5 | −12.9 |
| 56 | 88.6 | −7.9 | −12.9 |
| 57 | 88.8 | −6.7 | −12.9 |
| 58 | 88.8 | −7.0 | −12.9 |
| 59 | 88.8 | −8.2 | −12.9 |
| 60 | 88.8 | −8.5 | −12.9 |
| 61 | 88.8 | −8.5 | −12.9 |
| 62 | 88.8 | −9.7 | −12.9 |
| 63 | 88.8 | −8.2 | −12.9 |
| 64 | 88.8 | −8.5 | −12.9 |
| 65 | 88.8 | −9.7 | −12.9 |
| 66 | 88.8 | −9.7 | −12.9 |
| 68 | 88.8 | −12.9 | −12.9 |
| 69 | 90.7 | −12.9 | −12.9 |
| 71 | 91.7 | −12.9 | −13.4 |
| 822 | 70.5 | −10.9 | −10.9 |
| 823 | 70.5 | −10.9 | −10.9 |
| 824 | 70.3 | −9.1 | −10.9 |
| 825 | 71.9 | −9.1 | −10.9 |
| 827 | 74.3 | −9.4 | −10.9 |
| 828 | 73.7 | −9.6 | −10.9 |
| 829 | 73.7 | −8.1 | −10.9 |
| 913 | 80.0 | −8.2 | −11.2 |
| 914 | 80.0 | −8.2 | −11.2 |
| 915 | 80.1 | −7.9 | −11.2 |
| 916 | 79.4 | −7.6 | −11.2 |
| 1100 | 79.7 | −5.8 | −11.4 |
| 1102 | 78.5 | −6.4 | −11.4 |
| 1103 | 77.1 | −7.0 | −11.4 |
| 1104 | 74.9 | −6.7 | −11.4 |

TABLE 3-continued

PREFERRED HUMAN ACE MRNA-SPECIFIC
25-MER OLIGONUCLEOTIDES

| Beginning Oligo Position for each n-mer | $T_m$ | 3' dG | GC Clamp |
|---|---|---|---|
| 1105 | 74.9 | -7.9 | -11.4 |
| 1106 | 75.6 | -8.2 | -11.4 |
| 1107 | 75.2 | -8.2 | -11.4 |
| 1108 | 72.5 | -8.5 | -10.0 |
| 1109 | 70.4 | -7.0 | -10.0 |
| 1110 | 68.6 | -7.0 | -10.0 |
| 1111 | 68.5 | -6.4 | -10.0 |
| 1529 | 75.4 | -9.0 | -11.4 |
| 1530 | 73.9 | -6.7 | -11.4 |
| 1531 | 76.1 | -8.2 | -11.4 |
| 1532 | 77.4 | -9.4 | -11.4 |
| 1533 | 76.8 | -9.4 | -11.4 |
| 1534 | 76.7 | -9.4 | -11.4 |
| 1535 | 76.0 | -7.9 | -11.4 |
| 1536 | 74.3 | -6.7 | -11.4 |
| 1538 | 74.6 | -7.3 | -11.4 |
| 1539 | 75.3 | -7.3 | -11.4 |
| 1540 | 74.5 | -6.9 | -11.4 |
| 1541 | 76.7 | -6.9 | -11.4 |
| 1542 | 78.9 | -8.1 | -11.4 |
| 1543 | 76.9 | -8.1 | -10.2 |
| 1936 | 73.3 | -6.6 | -11.2 |
| 2004 | 77.9 | -11.4 | -11.7 |
| 2005 | 77.9 | -9.9 | -11.7 |
| 2006 | 77.9 | -9.9 | -11.7 |
| 2095 | 75.4 | -7.0 | -10.0 |
| 2096 | 73.0 | -6.4 | -10.0 |
| 2097 | 70.9 | -5.8 | -10.0 |
| 2381 | 88.1 | -12.9 | -12.9 |
| 2382 | 88.4 | -12.9 | -12.9 |
| 2383 | 88.4 | -12.9 | -12.9 |
| 2384 | 87.4 | -10.9 | -12.9 |
| 2385 | 86.6 | -9.4 | -12.9 |
| 2386 | 87.4 | -7.9 | -12.9 |
| 2387 | 85.5 | -6.4 | -12.9 |
| 2518 | 81.7 | -11.4 | -11.4 |
| 2519 | 84.3 | -12.9 | -12.9 |
| 2696 | 76.3 | -9.7 | -11.2 |
| 2697 | 77.8 | -8.2 | -11.2 |
| 2698 | 79.8 | -7.0 | -11.2 |
| 2699 | 78.3 | -7.0 | -11.2 |
| 2700 | 79.8 | -8.2 | -11.2 |
| 2701 | 81.8 | -9.7 | -11.2 |
| 2702 | 83.8 | -10.9 | -11.2 |
| 2703 | 85.4 | -12.4 | -12.4 |
| 2704 | 85.8 | -12.4 | -12.4 |
| 2705 | 84.0 | -10.9 | -12.4 |
| 2706 | 84.8 | -9.4 | -12.4 |
| 2800 | 80.7 | -8.5 | -12.4 |
| 2801 | 82.5 | -9.7 | -12.4 |
| 2821 | 83.0 | -8.2 | -12.9 |
| 2904 | 77.0 | -8.2 | -11.7 |
| 2905 | 74.8 | -7.6 | -11.7 |
| 2906 | 74.8 | -7.6 | -11.7 |
| 2907 | 73.7 | -6.4 | -11.7 |
| 2908 | 72.2 | -6.4 | -11.7 |
| 3087 | 75.7 | -10.0 | -12.9 |
| 3088 | 76.5 | -8.5 | -12.9 |
| 3089 | 78.7 | -8.5 | -12.9 |
| 3326 | 82.6 | -7.9 | -12.4 |
| 3327 | 81.3 | -7.9 | -11.2 |
| 3328 | 79.1 | -6.1 | -11.2 |
| 3329 | 77.0 | -6.4 | -11.2 |
| 3330 | 75.1 | -6.4 | -11.2 |
| 3331 | 74.0 | -6.7 | -11.2 |

Oligo position refers to the starting base position corresponding to the human ACE sequence for each of the indicated 25-mers. For example, the first oligonucleotide begins at base position 55 in the sequence and extends until position 79. The last indicated oligonucleotide begins at base 3331 in the human ACE sequence and continues until position 3355 in the sequence. In addition to the indicated 25-mers, smaller internal n-mers from 9 bases in length up to the full length 25-mer are also contemplated to be useful in the practice of the present invention. For example, in addition to the first indicated 25-mer (extending from position 55 to 79), the internal 24-mers (extending from position 55 to 78 or from position 56–79) are also considered to fall within the scope of this disclosure, as are all internal 23-mers of each sequence (e.g., base 55 to base 77, base 56 to 78, and base 57–79) are considered useful. In similar fashion, all internal 22-mers, 21-mers, 20-mers, 19-mers, 18-mers, 17-mers, 16-mers, 15-mers, 14-mers, 13-mers, 12-mers, 11-mer, 10-mers, and 9-mers, of each of the disclosed 25-mers are also considered to fall within the scope of this disclosure.

TABLE 4

PREFERRED HUMAN ACE MRNA-SPECIFIC
35-MER OLIGONUCLEOTIDES

| Beginning Oligo Position for each n-mer | $T_m$ | 3' dG | GC Clamp |
|---|---|---|---|
| 55 | 100.4 | -9.7 | -12.9 |
| 56 | 100.3 | -9.7 | -12.9 |
| 58 | 102.2 | -12.9 | -12.9 |
| 59 | 102.2 | -12.9 | -12.9 |
| 61 | 104.0 | -12.9 | -13.4 |
| 815 | 86.0 | -9.1 | -10.9 |
| 817 | 85.9 | -9.4 | -10.9 |
| 818 | 85.9 | -9.6 | -10.9 |
| 819 | 87.0 | -8.1 | -10.9 |
| 1100 | 89.0 | -7.0 | -11.4 |
| 1101 | 87.8 | -6.4 | -11.4 |
| 1102 | 87.8 | -6.1 | -11.4 |
| 1103 | 85.9 | -6.4 | -11.4 |
| 1104 | 85.0 | -6.4 | -11.4 |
| 1105 | 84.6 | -7.0 | -11.4 |
| 1106 | 84.6 | -7.0 | -11.4 |
| 1107 | 85.5 | -8.2 | -11.4 |
| 1108 | 84.0 | -8.2 | -10.0 |
| 1109 | 82.1 | -7.8 | -10.0 |
| 1526 | 85.9 | -6.7 | -11.4 |
| 1528 | 87.0 | -7.3 | -11.4 |
| 1529 | 87.6 | -7.3 | -11.4 |
| 1530 | 86.0 | -6.9 | -11.4 |
| 1531 | 87.2 | -6.9 | -11.4 |
| 1532 | 88.1 | -8.1 | -11.4 |
| 1533 | 86.7 | -8.1 | -11.4 |
| 1534 | 87.9 | -8.5 | -11.4 |
| 2689 | 86.6 | -7.0 | -11.2 |
| 2690 | 87.0 | -8.2 | -11.2 |
| 2691 | 88.2 | -9.7 | -11.2 |
| 2692 | 89.7 | -10.9 | -11.2 |
| 2693 | 89.9 | -12.4 | -12.4 |
| 2694 | 91.8 | -12.4 | -12.4 |
| 2695 | 91.1 | -10.9 | -12.4 |
| 2696 | 91.8 | -9.4 | -12.4 |
| 2790 | 90.9 | -8.5 | -12.4 |
| 2791 | 92.4 | -9.7 | -12.4 |

Oligo position refers to the starting base position corresponding to the human ACE sequence for each of the indicated 35-mers. For example, the first oligonucleotide begins at base position 55 in the sequence and extends until position 89. The last indicated oligonucleotide begins at base 2791 in the human ACE sequence and continues until position 2825 in the sequence. In addition to the indicated 35-mers, smaller internal n-mers from 9 bases in length up to each of the full length 35-mers listed are also contemplated to be useful in the practice of the present invention. For example, in addition to the first indicated 35-mer (extending from position 55 to 89), the internal 34-mers (extending from position 55 to 88 or from position 56–89) are also considered to fall within the scope of this disclosure, as are all internal 34-mers of each sequence as well as all internal 33-mers, 32-mers, 31-mers, 30-mers, 29-mers, 28-mers, 27-mers, 26-mers, 25-mers, 24-mers, 23-mers, 22-mers, 21-mers, 20-mers, 19-mers, 18-mers, 17-mers, 16-mers, 15-mers, 14-mers, 13-mers, 12-mers, 11-mers, 10-mers, and 9-mers, of each of the disclosed 35-mers are also considered to fall within the scope of this disclosure.

3.0 BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. Pattern of blood pressure reduction with a single (3 mg/kg) injection of an AS-ODN in the jugular vein of SHR. The ODN composition comprises a 9-mer consisting of the 3' 9 bases of SEQ ID NO:1. Day O indicates injection day. Blood pressure was monitored using implanted telemetry device with sample for 10 seconds every 10 minutes. Each point represents a mean of 3 hrs, equal 18 measurements.

Figure 2:
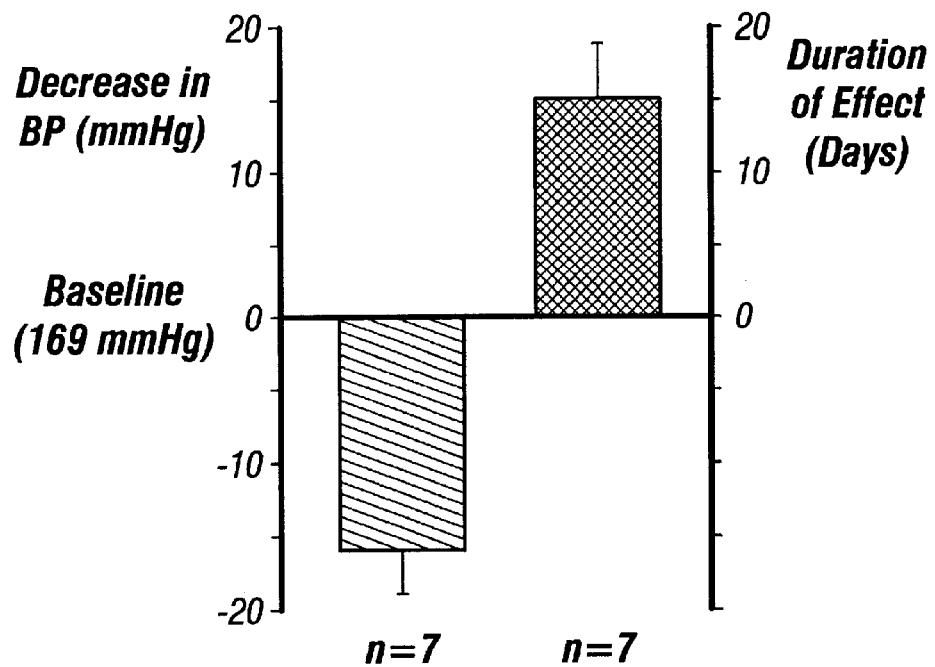

FIG. 2. Effectiveness of ACE antisense 9-mer after i.v. injection of SHR. Dose was 3 mg/kg, in the jugular vein. Hatched bar represents decrease in blood pressure from baseline ±SEM. Baseline was established based on 7 days' measurements before injection. Black bar indicates duration of effect in days ±SEM. Duration of effect is amount of days after injections when blood pressure was below baseline. Blood pressure was monitored using implanted telemetry device with sample for 10 seconds every 10 minutes. Each point represents a mean of 3 hrs, equal 18 measurements.

4.0 DESCRIPTION OF ILLUSTRATIVE EMBODIMENTS

4.1 Antisense Oligonucleotides

The end result of the flow of genetic information is the synthesis of protein. DNA is transcribed by polymerases into messenger RNA and translated on the ribosome to yield a folded, functional protein. Thus, even from this simplistic description of an extremely complex set of reactions, it is obvious that there are several steps along the route where protein synthesis can be inhibited. The native DNA segment coding for ACE, as all such mammalian DNA strands, has two strands: a sense strand and an antisense strand held together by hydrogen bonding. The messenger RNA coding for ACE has the same nucleotide sequence as the sense DNA strand except that the DNA thymidine is replaced by uridine. Thus, synthetic antisense nucleotide sequences will bind to the mRNA coding for ACE and inhibit expression of the protein.

4.1.1 Antisense Oligonucleotides Targeted to mRNA

The targeting of antisense oligonucleotides to bind mRNA is one mechanism to shut down protein synthesis. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829, each specifically incorporated herein by reference in its entirety). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., 1988; Vasanthakumar and Ahmed, 1989; Peris et al., 1998; U.S. Pat. No. 5,801,154; U.S. Pat. No. 5,789,573; U.S. Pat. No. 5,718,709 and U.S. Pat. No. 5,610,288, each specifically incorporated herein by reference in its entirety). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683, each specifically incorporated herein by reference in its entirety).

4.1.2 Ace Antisense Oligonucleotides

The oligonucleotide compounds of the invention bind to the messenger RNA coding for human ACE thereby inhibiting expression of the protein. Preferred compounds of the invention are antisense to the sense DNA sequence coding for human ACE. The sequence coding for the human ACE gene (SEQ ID NO:18) is disclosed in U.S. Pat. No. 5,359,045 and U.S. Pat. No. 5,480,793, each specifically incorporated herein by reference in its entirety.

In the specification and claims, the letters, A, G, C, T, and U respectively indicate nucleotides in which the nucleoside is Adenosine (Ade), Guanosine (Gua), Cytidine (Cyt), Thymidine (Thy), and Uridine (Ura). As used in the specification and claims, compounds that are antisense to the ACE DNA or mRNA sense strand are compounds which have a nucleoside sequence complementary to the sense strand. Table 5 shows the four possible sense strand nucleosides and their complements present in an antisense compound.

TABLE 5

| Sense | Antisense |
|---|---|
| Ade | Thy |
| Gua | Cyt |
| Cyt | Gua |
| Thy | Ade |
| Ura | Ade |

It will be understood by those skilled in the art that the present invention broadly includes oligonucleotide compounds which are capable of binding to the sense mRNA strand coding for ACE. Thus, the invention includes compounds which are not strictly antisense: the compounds may have some non-complementary bases provided such compound have sufficient binding affinity for ACE mRNA to inhibit expression.

The compounds of Formula I also differ from native DNA in that some or all of the phosphates in the nucleotides are replaced by phosphorothioates (X=S) or methylphosphonates (X=$CH_3$) or other $C_{1-4}$ alkylphosphonates. The compounds of Formula I optionally may be further differentiated from native DNA by replacing one or both of the free hydroxy groups of the antisense molecule with $C_{1-4}$ alkoxy groups (R=$C_{1-4}$ alkoxy). As used herein, $C_{1-4}$ alkyl means a branched or unbranched hydrocarbon having 1 to 4 carbonatoms.

Formula I compounds also may be substituted at the 3' and/or 5' ends by a substituted acridine derivative. As used herein, "substituted acridine" means any acridine derivative capable of intercalating nucleotide strands such as DNA. Preferred substituted acridines are 2-methoxy-6-chloro-9-pentylaminoacridine, N-(6-chloro-2-methoxyacridinyl)-O-methoxydiisopropylaminophosphinyl-3-aminopropanol, and N-(6-chloro-2-methoxyacridinyl)-O-methoxydiisopropylaminophosphinyl-5-aminopentanol. Other suitable acridine derivatives are readily apparent to persons skilled in the art. Additionally, as used herein "P(0)

(0)-substituted acridine" means a phosphate covalently linked to a substitute acridine.

The compounds of Formula I have at least 9 to about 35 or so nucleotides in length. As used herein, the term "nucleotides" includes nucleotides in which the phosphate moiety is replaced by phosphorothioate or alkylphosphonate and the nucleotides may be substituted by substituted acridines. Preferred Formula I compounds have at least 9 to about 25 nucleotides, while more preferred compounds have at least 9 to about 15 or so nucleotides. Compounds having fewer than 9 nucleotides are less desirable because they generally have less specificity and compounds having greater than about 35 nucleotides are less desirable because their physical size and charge will attenuate the crossing of the lipophilic cell membrane. Thus, they are less likely to enter cells.

Although Formula I compounds that are antisense to human ACE mRNA are preferred, Formula I includes nucleotide compounds which lack a complement for each nucleotide in a segment of the mRNA sense strand provided such compounds have sufficient binding affinity for human ACE mRNA to inhibit ACE expression. The routine screening procedure of Example 2 is useful for determining whether specific oligonucleotides defined by Formula I are effective in inhibiting human ACE expression.

Formula I compounds in which R is H are preferred. R, however, can be $C_{1-4}$ alkyl provided the resulting compounds retains sufficient binding affinity for the ACE mRNA sense strand to inhibit expression of ACE.

Formula I compounds in which at least one X is S are prepared by the following published procedures: Stec et al., 1984; Adams et al., 1983; Caruthers et al., 1982; Broido et al., 1984. The reaction scheme described in these published procedures is conducted on a solid support.

The reaction scheme involves 1H-tetrazole-catalyzed coupling of phosphoramidites to give phosphate intermediates which are reacted with sulfur in 2,6-lutidine to give phosphate compounds. Oligonucleotide compounds are prepared by treating the phosphate compounds with thiophenoxide (1:2:2 thiophenol/triethylamine/tetra-hydrofuran, room temperature, 1 h). The reaction sequence is repeated until an oligonucleotide compound of the desired length has been prepared (Formula 1). The Formula I compounds are cleaved from the support by treating with ammonium hydroxide at room temperature for 1 h and then are further deprotected by heating at about 50° C. overnight to yield Formula I compounds. Formula I compounds in which at least one X is oxygen are prepared by substituting $I_2 H_2O$ for the sulfur in 2,6-lutidine.

Formula I compounds in which at least X is $CH_3$ or other $C_{1-4}$ alkyl are prepared by the following published procedure: Agarwal and Riftina, 1979. The reaction sequence is conducted on a solid support. The reaction procedure involves phosphorylation of the 3'-hydroxyl group of a 5'-protected nucleoside using methylphosphonoditriazolide as the phosphorylating reagent followed by benzene sulfonyl-catalyzed coupling of the methylphosphonates to yield the methyl phosphonate oligonucleotide. Methylphosphonoditriazolide is prepared in situ from equimolar quantities of methylphosphono-dichloridate, triethylamine, and triazole. Benzene sulfonyl tetrazole also was prepared in situ from pyridine, benzene sulfonic acid and triethylamine. Repeating this reaction sequence followed by cleavage from the support and deprotection yield Formula I compounds Formula I compounds in which R is $C_{1-4}$ alkyl are prepared by replacing the DMT-protected compounds with $C_{1-4}$ alkylethers.

Formula I compounds in which R is P(0) (0)-substituted acridine also are prepared by the following published procedures: Asseline and Thuong, 1989; Stein et al., 1988. These published procedures include synthesis of a nucleoside phosphoramidite-bearing acridine derivative which then is reacted with 2,2'-dithiodiethanol attached to a support. The elongation chain then is carried out of an automatic solid-phase DNA synthesized as described above. These published procedures also include synthesis of nucleoside phosphoramidite-bearing acridine derivatives by reacting substituted 9-(3-hydroxypropyl) amino acridines with N-ethyldiisopropylamine followed by N,N-diisopropylmethylphosphonanidic chloride. Using an automated DNA synthesizer, Formula I compounds in which R is P(0) (0)-substituted acridine are prepared by an extra round of synthesis using the acridinyl phosphoramidites in acetonitrile.

The utility of Formula I compounds in inhibiting expression of human ACE was demonstrated in vitro by the procedures of Example 2.

The compounds of Formula I can be incorporated into convenient pharmaceutical dosage forms such as capsules, tablets, or injectable preparations. Solid or liquid pharmaceutical carriers can be employed. Solid carriers include starch, lactose, calcium sulfate dehydrate, terra alba, sucrose, talc, gelatin, agar, pectin, acacia, magnesium stearate, and stearic acid. Liquid carriers include syrup, peanut oil, olive oil, saline and water. Liposomal, viral vector, and protein conjugate preparations can also be used as carriers. Similarly, the carrier or diluent may include any prolonged release material, such as glyceryl monostearate of glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension. When a liquid carrier is used it will most of ten be a saline solution or phosphate buffered saline solution.

Because the lungs are the major site of angiotensin I conversion to angiotensin II by ACE, an especially advantageous delivery system for the compounds of the present invention involves a pharmaceutical composition of these compounds which is suitable for use in a nasal spray kit. The pharmaceutical carrier in such a nasal spray kit would include, for example, saline.

The pharmaceutical preparations are made following conventional techniques of a pharmaceutical chemist involving mixing, granulating and compressing, when necessary, for tablet forms or mixing, filling, and dissolving the ingredients, as appropriate, to give the desired oral or parenteral products.

Doses of the present Formula I compounds (in a pharmaceutical dosage unit as described above) will be an efficacious, nontoxic quantity selected from the range of 1 ng/kg to 500 mg/kg of active compound, preferably less than 10 mg/kg. The selected dose is administered to a human patient in need of inhibition of ACE expression from 1–6 or more times daily, orally, rectally, by injection, or continuously by infusion. Oral formulations would generally require somewhat larger dosages to overcome the effects of gastric decomposition. Intravenous or intraarterial administration would generally require lower doses since the drug is placed directly into the systemic circulation. Dosages for nasal sprays typically range from about 10 mg to about 50 mg (total) or about 0.1 mg/kg to about 10 mg/kg. Therefore, the dose will depend on the actual route of administration.

This invention relates to an oligonucleotide compound which binds to a region of ACE mRNA preventing the production of ACE protein which is involved in the development and maintenance of hypertensive blood pressure. By placing the antisense molecules in pharmaceutical carriers suitable for a nasal spray it is possible to obtain compositions which can be used in a method to target the delivery of the antisense molecules directly to the lung, the major site of angiotensin I conversion to angiotensin II by ACE in the body.

The compounds and compositions of the present invention are unique because there is no commercially available agent which specially inhibits the cellular synthesis of ACE. Additionally, due to the chemical nature of antisense molecules the action is highly specific, allowing the administration of small doses, with potentially fewer side effects than conventional antihypertensive agents.

In exemplary embodiments, the invention concerns oligonucleotide sequences that comprise all, or a portion of any of the sequences shown in Table 1, Table 2, Table 3, and Table 4, and that specifically bind to ACE mRNA and that alter the translation of such mRNA into mature ACE polypeptide, and that ultimately alter the level of ACE activity in a host cell. In one embodiment, the oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of the naturally-occurring ACE mRNA.

In an illustrative embodiment, sequences complementary to the rat ACE mRNA were prepared and demonstrated in vitro and in vivo to be effective in altering ACE expression and reducing blood pressure in an affected animal. In this example, the following antisense sequences were prepared and analyzed in the accepted animal model for hypertension described herein:

```
5'-CCCCCATGGCGCGGT-3'      (SEQ ID NO:1)

5'-CCGCGGAAAAGTTGC-3'      (SEQ ID NO:2)

5'-GCAATCCAGGGTCAA-3'      (SEQ ID NO:3)
```

These sequences were prepared based on the nucleotide sequence of the rat ACE gene (SEQ ID NO:19) which was disclosed in Koike et al. (1994).

In a second illustrative embodiment, sequences were prepared which were substantially complementary to the human ACE-specific mRNA sequence, and these oligonucleotide compositions were shown to be effective in altering human ACE activity in vitro. The sequence of these antisense ODN were:

```
5'-CCCCCATGACGCGGT-3'      (SEQ ID NO:4)

5'-TGCGCGGTGCTCGGC-3'      (SEQ ID NO:5)

5'-CACGCTCTGGAACAG-3'      (SEQ ID NO:6)
```

These sequences were prepared based on the nucleotide sequence of the human ACE gene (SEQ ID NO:18) which was disclosed in Intl. Pat. Appl. Publ. No. WO 90/03435 (specifically incorporated herein by reference in its entirety).

Selection of antisense compositions specific for a given gene sequence is based upon analysis of the chosen target sequence (i.e. in these illustrative examples the rat and human sequences) and determination of secondary structure, $T_m$, binding energy, relative stability, and antisense compositions were selected based upon their relative inability to form dimers, hairpins, or other secondary structures that would reduce or prohibit specific binding to the target mRNA in a host cell. The results of these analyses are shown in Table 1, Table 2, Table 3, and Table 4, for illustrative 15-, 25-, and 35-mer oligonucleotides and selected target sequences.

Highly preferred target regions of the mRNA, are those which are at or near the AUG translation initiation codon, and those sequences which were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

The sequence of oligonucleotides given above are the most preferred sequences for inhibiting rat and human ACE, respectively. Additional nucleotides at either end derived by the same process (using OLIGO and BLAST) are also envisioned by this invention. The effective length of the ODN is from 9–25 nucleotides. The inventors contemplate oligonucleotide compositions in the range of from at least 9 to about 35 or so bases in length are most preferred for the practice of the methods of the invention. In illustrative embodiments, the antisense compounds of the invention differ from native DNA by the modification of the phosphodiester backbone to extend the life of the antisense ODN, in which the phosphate substituents are replaced by phosphorothioates. Likewise, one or both ends of the oligonucleotide may be substituted by one or more acridine derivatives which intercalates nucleotide strands of DNA.

4.2 ACE Assays

An important aspect of the invention involves the assay of ACE activity, either in vitro or in vivo following administration of one or more of the disclosed antisense compositions. Several methods are well-known for ACE detection in vitro and to assay the efficacy of one or more of the disclosed compositions as an ACE inhibitor. Exemplary assay methods are described herein:

4.2.1 Fluorescent Substrate-Based Assays

Fluorescent ACE substrates can be used to assay ACE activity and to screen antihypertensive compounds, and in particular, the oligonucleotide compositions of the present invention that inhibit ACE activity. An exemplary assay method using such fluorescent substrates is described in U.S. Pat. No. 5,723,307 (specifically incorporated herein by reference in its entirety).

4.2.2 Radiometric and Colorimetric Assays for ACE

Radiolabeled and colorimetric ACE assays have also been developed and described e.g., in U.S. Pat. No. 4,335,041; U.S. Pat. No. 4,292,404 and U.S. Pat. No. 4,407,944 (each specifically incorporated herein by reference in its entirety). The radioisotope assays typically involve radiolabeling of the selected ACE inhibitor, and then assaying for the presence of the radio label. These inhibitors bind ACE and therefore directly assay the presence or formation of ACE.

Alternatively, one may desire to assay ACE inhibitory activity by a colorimetric assay. These assays generally involve the use of compounds that when cleaved by the ACE enzyme, form colorimetric products that are then quantitated by measuring the amount of light absorbed at one or more specific wavelengths.

4.2.3 Antibody-Based ACE Assays

Another method commonly used for measuring levels of ACE, even at femtomolar quantities, uses antibodies that are specific for either a substrate for ACE, including the natural substrate angiotensin I, or antibodies that are specific for a cleavage product of ACE, including the natural ACE product, angiotensin II. Methods using antibodies such as these are described e.g., in U.S. Pat. No. 5,407,803 (specifically incorporated herein by reference in its entirety).

4.3 Methods for Screening Patients at Risk for Hypertension

Because ACE is an important step in the formation of Ang II, which can induce hypertension in an animal, it is often desirable to measure and quantitate levels of ACE activity in an animal under a variety of conditions, even during the course of a treatment regimen designed to ameliorate the hypertensive condition in such an animal. Likewise, in many instances, it is desirable to employ methods for screening polymorphisms of the gene encoding human ACE (SEQ ID NO:18) to identify patients "at risk" for hypertension, and to identify alleles of the gene both in vitro and in vivo.

As such, the use of one or more of the nucleotide compositions described herein as a probe for identifying a gene encoding ACE, and methods for correlating the presence of such nucleotide segments with the risk of hypertension is particularly desirable. Exemplary methods employing oligonucleotide compositions as probes for ACE gene compositions are described in U.S. Pat. No. 5,800,990; U.S. Pat. No. 5,801,040 and U.S. Pat. No. 5,480,793 (each specifically incorporated herein by reference in its entirety).

4.4 ACE Small Molecule and Peptide Inhibitors

The ACE inhibitors captopril (Capoten™, Capozide™, Bristol-Myers Squibb Co.), enalapril (Vasotec™, Vaseretic™, Merck and Co.), fosinopril (Monopril™, Bristol-Myers Squibb Co.) and lisinopril (Prinivil™, Merck and Co.; Zestril™, Zeneca Pharmaceuticals) are common drugs used to treat hypertension. These drug treatments are limited by short biological lifetimes in vivo and often result in a variety of negative side effects (Sadeck et al., 1997; Deira et al., 1997; Menefee et al., 1998). Additional small molecular weight ACE inhibitory compounds and oligopeptides have been synthesized and their methods of use described in U.S. Pat. No. 5,552,397; U.S. Pat. No. 5,449,661; U.S. Pat. No. 5,348,978; U.S. Pat. No. 5,238,921; U.S. Patent 5,098,887 and U.S. Pat. No. 4,216,209 (each specifically incorporated herein by reference in its entirety). In certain embodiments, such small molecules or other antihypertensive agents may be co-administered to an animal along with one or more of the disclosed antisense constructs. The administration of existing anti-hypertensive agents is well-known to those of skill in the art, and particular, to health practitioners who routinely diagnose and/or treat animals or patients suffering from hypertension.

4.5 Pharmaceutical Compositions

Therefore, in certain embodiments, the present invention also concerns formulation of one or more of the antisense polynucleotide compositions disclosed herein in pharmaceutically-acceptable solutions for administration to a cell or an animal, either alone, or in combination with one or more other modalities of antihypertensive therapy.

It will also be understood that, if desired, the nucleic acid segment, RNA, DNA or PNA antisense compositions disclosed herein may be administered in combination with other agents as well, such as, e.g., proteins or polypeptides or various pharmaceutically-active agents. As long as the composition comprises at least one ACE mRNA inhibitory antisense oligonucleotide, there is virtually no limit to other components which may also be included, given that the additional agents do not cause a significant adverse effect upon contact with the target cells or host tissues. The RNA, DNA, or PNA-derived antisense compositions may thus be delivered along with various other agents as required in the particular instance. Such RNA, DNA, or PNA antisense compositions may be purified from host cells or other biological sources, or alternatively may be chemically synthesized as described herein. Likewise, such compositions may comprise substituted or derivatized RNA, DNA, or PNA compositions. Such compositions may include modified peptide or nucleic acid substituent derivatives, as long as the base sequence of the RNA, DNA, or PNA molecule corresponds to one or more of the contiguous base sequences described herein that specifically bind to ACE mRNA, and that reduce or inhibit the extent of translation of this ACE mRNA into biologically-active ACE polypeptide.

The formulation of pharmaceutically-acceptable excipients and carrier solutions are well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

4.5.1 Oral Delivery

The pharmaceutical compositions disclosed herein may be delivered via oral administration to an animal, and as such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as those containing sodium borate, glycerin and potassium bicarbonate, or dispersed in a dentifrice, including: gels, pastes, powders and slurries, or added in a therapeutically effective amount to a paste dentifrice that may include water, binders, abrasives, flavoring agents, foaming agents, and humectants, or alternatively fashioned into a tablet or solution form that may be placed under the tongue or otherwise dissolved in the mouth.

4.5.2 Injectable Delivery

Alternatively, the pharmaceutical compositions disclosed herein may be administered parenterally, intravenously, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

4.5.3 Nasal Delivery

Because a major site of angiotensin II production by ACE is localized in the lungs, in certain embodiments, the inventors contemplate the administration of the pharmaceutical compositions by intranasal sprays, inhalation, and/or other aerosol delivery vehicles. Methods for delivering genes, nucleic acids, and peptide compositions directly to the lungs via nasal aerosol sprays has been described e.g., in U.S. Pat. No. 5,756,353 and U.S. Pat. No. 5,804,212 (each specifically incorporated herein by reference in its entirety), and delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4.5.4 Additional Modes of Delivery for ACE Antisense Compounds

In addition to the methods of delivery described above, the following techniques are also contemplated as alternative methods of ACE inhibitory compound delivery. Sonophoresis (i.e., ultrasound) has been used and described in U.S. Pat. No. 5,656,016 (specifically incorporated herein by reference in its entirety) as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. No. 5,770,219 and U.S. Pat. No. 5,783,208) and feedback controlled delivery (U.S. Pat. No. 5,697,899), each specifically incorporated herein by reference in its entirety.

4.6 Delivery Methods and Compositions

4.6.1 Liposome, Nanocapsule-, and Microparticle-Mediated Delivery

In certain embodiments, the inventors contemplate the use of liposomes, nanocapsules, microparticles, microspheres, lipid particles, vesicles, and the like, for the introduction of the antisense compositions of the present invention into suitable host cells. In particular, the antisense oligonucleotide compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core. Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the polynucleotide compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 µm) should be designed using polymers able to be degraded in vivo. Biodegradable polyalkylcyanoacrylate nanoparticles that meet these requirements are contemplated for use in the present invention, and such particles may be are easily made, as described (Couvreur et al., 1980; 1988; zur Muhlen et al., 1998; Zambaux et al. 1998; Pinto-Alphandry et al., 1995 and U.S. Patent 5,145,684, specifically incorporated herein by reference in its entirety). In particular, methods of antisense oligonucleotide delivery to a target cell using either nanoparticles or nanospheres (Schwab et al., 1994; Truong-Le et al., 1998) are also particularly contemplated to be useful in formulating the disclosed compositions for administration to an animal, and to a human in particular.

4.6.2 Peptide Vectors

The recent development of an antisense delivery method based on the use of a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It was demonstrated in that several molecules of the MPG peptides coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

4.7 Therapeutic and Diagnostic Kits

The invention also encompasses one or more of the antisense oligonucleotide compositions together with one or more pharmaceutically-acceptable excipients, carriers, diluents, adjuvants, and/or other components, such as additional antihypertensive compositions, oligonucleotides, peptides, antigens, or other therapeutic compositions as may be employed in the formulation of particular polynucleotide delivery formulations, and in the preparation of antihypertensive agents for administration to an animal.

As such, preferred animals for administration of the pharmaceutical compositions disclosed herein include mammals, and particularly humans. Other preferred animals include murines, bovines, equines, porcines, canines, and felines. The composition may include partially or significantly purified antisense oligonucleotide compositions, either alone, or in combination with one or more additional active ingredients, which may be obtained from natural or recombinant sources, or which may be obtainable naturally or either chemically synthesized, or alternatively produced in vitro from recombinant host cells expressing DNA segments encoding such additional active ingredients.

Therapeutic kits may also be prepared that comprise at least one of the ACE mRNA-specific antisense oligonucleotides disclosed herein and instructions for using the composition as a therapeutic agent. The container means for such kits may typically comprise at least one vial, test tube, flask, bottle, syringe or other container means, into which the antisense composition(s) may be placed, and preferably suitably aliquoted. Where a second antihypertensive agent is also provided, the kit may also contain a second distinct container means into which this second composition may be placed. Alternatively, the plurality of antihypertensive compositions may be prepared in a single pharmaceutical composition, and may be packaged in a single container means, such as a vial, flask, syringe, bottle, or other suitable single container means. The kits of the present invention will also typically include a means for containing the vial(s) in close confinement for commercial sale, such as, e.g., injection or blow-molded plastic containers into which the desired vial(s) are retained.

Alternatively, for the preparation of diagnostic kits, and for methods relating to the use of these compounds in the identification of ACE-specific nucleic acids in a biological sample, such kits may be prepared that comprise at least one of the ACE mRNA-specific antisense oligonucleotides disclosed herein and instructions for using the composition as a probe for ACE-specific nucleic acids in a hybridization assay. The container means for such kits may typically comprise at least one vial, test tube, microcentrifuge tube, or other container means, into which the antisense composition (s) may be placed and suitably aliquoted. Where a radiolabel or fluorigenic label or other such detecting means is included within the kit, the labeling agent may be provided either in the same container as the oligonucleotide composition, or may alternatively be placed in a second distinct container means into which this second composition may be placed and suitably aliquoted. Alternatively, the oligonucleotide composition and the label may be prepared in a single container means, and in most cases, the kit will also typically include a means for containing the vial(s) in close confinement for commercial sale and/or convenient packaging and delivery.

4.8 ACE mRNA-Specific Oligonucleotide Compositions

As mentioned, in certain aspects, the ACE-encoding DNA sequence information provided by the present disclosure allows for the preparation of relatively short DNA, RNA, PNA, or derivatives thereof having the ability to specifically hybridize to an ACE-specific mRNA sequence encoding all or a portion of the ACE polypeptide, which the inventors have demonstrated useful in (1) the regulation, control, alteration, reduction and/or inhibition of ACE activity in a cell; (2) the treatment of hypertension in an animal; and (3) the detection of ACE-specific nucleic acid sequences in a biological sample.

With respect to the latter, suitable antisense oligonucleotide sequences of an appropriate length may be prepared based on a consideration of the natural mRNA sequence to which it will hybridize, and the size of the particular oligonucleotide used. Such segments may be those that are complementary to native ACE or ACE-derived coding sequences, or alternatively, may be sequences which have undergone site-specific mutations to generate one or more mutations in the oligonucleotide sequence. The ability of such polynucleotides to specifically hybridize to the corresponding ACE-specific mRNA sequences lend them particular utility in a variety of embodiments, including means for altering the ACE activity in a cell, means for inhibiting the translation of ACE-specific mRNA, and means for reducing the level of Ang II both in vitro, as well as in a cell, a transformed host, a transgenic non-human mammal, and in the in vivo therapy of an animal and human disease resulting in elevated ACE activity.

The oligonucleotide sequences of the invention will also find particular utility as the basis for diagnostic hybridization assays for detecting ACE-specific RNA or DNA in clinical samples. Exemplary clinical samples that can be assayed for the presence of ACE or ACE-encoding mRNAs or DNAs include, but are not limited to, blood, serum, plasma, lymph, middle ear fluids, cerebrospinal fluid, sputum, bronchoalveolar fluid and the like. Such samples may be of mammalian origins, and in particular, or human, murine, equine, bovine, feline, porcine, or canine origin. A variety of hybridization techniques and systems are known that can be used in connection with the hybridization aspects of the invention, including diagnostic assays such as those described in U.S. Pat. No. 4,358,535, incorporated herein by reference. Samples derived from non-human mammalian sources, including animals of economic significance such as domestic farm animals, may also provide the basis for clinical specimens.

Accordingly, the nucleotide sequences of the invention are important for their ability to selectively form duplex molecules with complementary stretches of the nucleic acid segments encoding ACE epitopes. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one may desire to employ lower or reduced stringency hybridization conditions. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, one may desire to employ nucleic acid probes to isolate variants from clone banks containing mutated ACE-encoding clones. In particular embodiments, mutant clone colonies growing on solid media that contain variants of the ACE-encoding gene sequence could be identified on duplicate filters using hybridization conditions and methods, such as those used in colony blot assays, to only obtain hybridization between probes containing sequence variants and nucleic acid sequence variants contained in specific colonies. In this manner, small hybridization probes containing short variant sequences of these genes may be utilized to identify those clones growing on solid media that contain sequence variants of the entire genes. These clones can then be grown to obtain desired quantities of the variant nucleic acid sequences or the corresponding antigens.

In clinical and certain diagnostic embodiments, oligonucleotide sequences of the present invention are used in combination with an appropriate means, such as a label, for determining hybridization. A wide variety of appropriate indicator means are known in the art, including radioactive, enzymatic or other ligands, such as avidin/biotin, that are capable of giving a detectable signal. In preferred diagnostic embodiments, one will likely desire to employ an enzyme tag such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with pathogen nucleic acid-containing samples.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., middle ear effusion, bronchoalveolar lavage fluid) or even tissues, is adsorbed or otherwise affixed to a selected matrix or surface. This fixed, nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantified, by means of the label.

4.9 Probes and Primers for ACE-Related Polynucleotide Segments

As described above, the oligonucleotide compositions disclosed herein have utility as probes or primers in a variety of nucleic acid hybridization embodiments. As such, it is contemplated that nucleic acid segments that comprise a sequence region of at least about 9, 10, 11, 12, 13, 14, 15, 16, 17, 18, 19, or 20 or more contiguous bases that has the same sequence as, or is complementary to, a contiguous sequence from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18 or SEQ ID NO:19 will find particular utility in hybridization embodiments. Longer contiguous identical or complementary sequences, e.g., those of about 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 200, 300, 400, 500, 600, 700, 800, 900, 1000, etc. (including all intermediate lengths) and even up to full-length ACE-encoding or ACE-antisense polynucleotide sequences will also be of use in certain embodiments.

The ability of such nucleic acid probes to specifically hybridize to ACE -encoding sequences will enable them to be of use in detecting the presence of complementary sequences in a given sample, and also in the preparation of mutated oligonucleotide primers, or primers for use in preparing other genetic constructions. For example, one may desire to prepare antisense oligonucleotide compositions that are completely homologous to one or more regions of ACE-specific mRNA, or alternatively, compositions that contain at least one base mismatch within the sequence. Sequences having no more than about 4, or about 3, or about 2, or about 1 base mismatches within a given contiguous sequence of the oligonucleotide may be desirable to prepare compositions for diagnostic or therapeutic utility.

Nucleic acid molecules having sequence regions consisting of contiguous nucleotide stretches of about 9, 10, 11, 12, 13, 14, 15, 16, 17, 18, 19, 20, 30, 40, 50, or more identical or complementary bases disclosed in SEQ ID NO:18, or SEQ ID NO:19, are particularly contemplated as hybridization probes for use in, e.g., Southern and Northern blotting. This would allow an ACE-encoding polypeptide or regulatory gene product to be analyzed, both in diverse tissue types, cell lines, transformed and recombinant host cells and the like. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 14 and about 100 nucleotides, but larger contiguous complementarity stretches may be used, according to the length complementary sequences one wishes to detect.

The use of a hybridization probe of about 14–25 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17, or to any continuous portion of the ACE-encoding gene sequences shown in SEQ ID NO:18 or SEQ ID NO:19, and prepare a particular probe or primer. The choice of probe and primer sequences may be governed by various factors, such as, by way of example only, one may wish to employ primers from towards the termini of the total sequence.

The process of selecting and preparing a nucleic acid segment that comprise the contiguous sequence from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19, may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of the entire ACE-encoding gene or gene fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related ACE-encoding genes.

Of course, for some applications, for example, where one desires to prepare mutants employing a mutant primer strand hybridized to an underlying template or where one seeks to isolate one or more ACE-encoding sequences from related cell types, species, functional equivalents, or the like, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

4.10 Peptide Nucleic Acid Compositions

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. An excellent review of PNA including methods of making, characteristics of, and methods of using, is provided by Corey (1997) and is incorporated herein by reference. As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

4.10.1 Methods of Making PNAs

PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Doc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass., USA). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

4.10.2 Physical Properties of PNAs

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11–13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

4.10.3 Applications of PNAs

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

4.11 Methods of Nucleic Acid Delivery and DNA Transfection

In certain embodiments, it is contemplated that one or more RNA, DNA, PNAs and/or substituted polynucleotide compositions disclosed herein will be used to transfect an appropriate host cell. Technology for introduction of PNAs, RNAs, and DNAs into cells is well-known to those of skill in the art.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Wong and Neumann, 1982; Fromm et al., 1985; Tur-Kaspa et al., 1986; Potter et al., 1984; Suzuki et al., 1998; Vanbever et al., 1998), direct microinjection (Capecchi, 1980; Harland and Weintraub, 1985), DNA-loaded liposomes (Nicolau and Sene, 1982; Fraley et al., 1979; Takura, 1998) and lipofectamine-DNA complexes, cell sonication (Fechheimer et al., 1987), gene bombardment using high velocity microprojectiles (Yang et al., 1990; Klein et al., 1992), and receptor-mediated transfection (Curiel et al., 1991; Wagner et al., 1992; Wu and Wu, 1987; Wu and Wu, 1988). Some of these techniques may be successfully adapted for in vivo or ex vivo use.

Moreover, the use of viral vectors (Lu et al., 1993; Eglitis and Anderson, 1988; Eglitis et al., 1988), including retroviruses, baculoviruses, adenoviruses, adenoassociated viruses, vaccinia viruses, Herpes viruses, and the like are well-known in the art, and are described in detail herein.

4.12 Expression Vectors

The present invention contemplates an expression vector comprising at least one polynucleotide of the present invention. Thus, in one embodiment an expression vector is constructed with a specific DNA molecule orientated in the antisense direction. In another embodiment, a promoter is operatively linked to a sequence region that encodes a functional RNA such as a RNA, a ribozyme or an antisense RNA.

As used herein, the term "operatively linked" means that a promoter is connected to a functional RNA in such a way that the transcription of that functional RNA is controlled and regulated by that promoter. Means for operatively linking a promoter to a functional RNA are well known in the art.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

4.13 ACE Inhibitor Treatments and Combination Therapies

In addition to treating hypertension, other clinical uses of ACE small molecule inhibitors have been described. Two particularly interesting uses of ACE small molecule inhibitors are the treatment of voluntary alcohol consumption in humans and cardiac insufficiency, described in U.S. Pat. No. 5,145,864 and U.S. Pat. No. 5,744,496 (each specifically incorporated herein by reference in its entirety).

Combination therapies are commonly used for the treatment of certain types of cancers and are well known in the art (U.S. Pat. No. 5,710,134, specifically incorporated herein by reference in its entirety). A combination therapy requires the administration of more than one compound or treatment to combat a specific disease. Thus, ACE AS-ODNs can be combined with current ACE inhibitory compounds to enhance treatment, as long as the given therapeutic approach is not detrimental to the patient's condition and does not counteract the ACE AS-ODN treatment. For example, a synergistic combination therapy is described in U.S. Pat. No. 5,663,188 (specifically incorporated herein by reference in its entirety) that relates to the administration of a renin inhibitor, an ACE inhibitor and an ANG II antagonist. This suggests that specific inhibitors of the renin-angiotensin system may be combined with the ACE AS-ODNs in the present invention to increase the efficacy of treatment.

4.14 Expression in Animal Cells

The inventors contemplate that an antisense oligonucleotide comprising a contiguous nucleic acid sequence from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17, or a larger oligonucleotide comprising one or more of these nucleic acid sequences or substantially identical sequences thereto, may also be utilized to inhibit the synthesis of ACE in a transformed host cell. Such cells are preferably animal cells, including mammalian cells such as those obtained from a human or other primate, murine, canine, bovine, equine, epine, or porcine species. The cells may be transformed with one or more vectors comprising an ACE-specific antisense construct of interest, such that the antisense construct is sufficient to alter, reduce, or prevent the expression of ACE-specific mRNA in vitro and/or in vivo.

4.14.1 Transgenic Animals

It is contemplated that in some instances the genome of a transgenic non-human animal of the present invention will have been altered through the stable introduction of one or more of the ACE antisense oligonucleotide compositions described herein, either native, synthetically modified, or mutated. As used herein, the term "transgenic animal" is intended to refer to an animal that has incorporated exogenous DNA sequences into its genome. In designing a heterologous gene for expression in animals, sequences which interfere with the efficacy of gene expression, such as polyadenylation signals, polymerase II termination sequences, hairpins, consensus splice sites and the like, are eliminated. Current advances in transgenic approaches and techniques have permitted the manipulation of a variety of animal genomes via gene addition, gene deletion, or gene modifications (Franz et al., 1997). For example, mosquitos (Fallon, 1996), trout (Ono et al., 1997), zebrafish (Caldovic and Hackett, 1995), pigs (Van Cott et al., 1997) and cows (Haskell and Bowen, 1995), are just a few of the many animals being studied by transgenics. The creation of transgenic animals that express human proteins such as α-1-antitrypsin, in sheep (Carver et al., 1993); decay accelerating factor, in pigs (Cozzi et al., 1997); and plasminogen activator, in goats (Ebert et al., 1991) have previously been demonstrated. The transgenic synthesis of human hemoglobin (U.S. Pat. No. 5,602,306) and fibrinogen (U.S. Pat. No. 5,639,940) in non-human animals have also been disclosed, each specifically incorporated herein by reference in its entirety. Further, transgenic mice and rat models have recently been described as new directions to study and treat cardiovascular diseases such as hypertension in humans (Franz et al., 1997; Pinto-Siestma and Paul, 1997). The construction of a transgenic mouse model has recently been used to assay potential treatments for Alzheimer's disease (U.S. Pat. No. 5,720,936, specifically incorporated herein by reference in its entirety). It is contemplated in the present invention that transgenic animals contribute valuable information as models for studying the effects of ACE AS-ODN compositions.

4.14.2 Selection

The enzyme luciferase is useful as a screenable marker in the context of the present invention (Kang et al., 1998). In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time. The above techniques also could be utilized if the screenable marker is the green fluorescent protein.

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. Therefore it is proposed that combinations of selection and screening will enable one to identify transformants in a wider variety of cell and tissue types.

4.14.3 Characterization

To confirm the presence of the exogenous DNA or "transgene(s)" in the transformed cells, a variety of assays may be performed. Such assays include, for example, "molecular biological" assays, such as Southern and Northern blotting, RT-PCR™ and PCR™; "biochemical" assays, such as detecting the presence of a protein product, e.g., by immunological means (ELISAs and Western blots) or by enzymatic function assay.

4.14.4 Gene Expression

While Southern blotting and PCR™ may be used to detect the ACE gene(s) in question, they do not provide information as to whether the gene is being expressed. Expression may be evaluated by RT-PCR™ for mRNA and/or specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Transgenic animals are described that synthesize epitope tagged prion proteins as a method of detecting the expressed protein(s) (U.S. Pat. No. 5,789,655, specifically incorporated herein by reference in its entirety).

Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the cells of the animal or human.

4.14.5 DNA Integration, RNA Expression and Inheritance

Genomic DNA may be isolated from animal cell lines or any animal parts to determine the presence of the exogenous gene through the use of techniques well known to those skilled in the art. Note, that intact sequences will not always be present, presumably due to rearrangement or deletion of sequences in the cell.

The presence of DNA elements introduced through the methods of this invention may be determined by polymerase chain reaction (PCR™). Using this technique discreet fragments of DNA are amplified and detected by gel electrophoresis. This type of analysis permits one to determine whether a gene is present in a stable transformant, but does not prove integration of the introduced gene into the host cell genome. It is the experience of the inventors, however, that DNA has been integrated into the genome of all transformants that demonstrate the presence of the gene through PCR™ analysis (Wu et al., 1998). In addition, it is not possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™ e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Whereas DNA analysis techniques may be conducted using DNA isolated from any part of an animal, RNA will only be expressed in particular cells or tissue types and hence it will be necessary to prepare RNA for analysis from these tissues. PCR™ techniques may also be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

4.15 Vector Backbone

Throughout this application, the term "expression construct" is meant to include any type of genetic construct containing a nucleic acid comprising an antisense sequence that is capable of interacting with the mRNA of ACE and affecting its expression, and/or translation into mature ACE polypeptide.

In certain embodiments, when the antisense construct is placed under the control of a promoter for expression in a transformed host cell, the presence of one or more enhancer elements may be desirable in the vector constructs that comprise the ACE mRNA-specific antisense oligonucleotide sequence.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

In one embodiment, the expression construct of the present invention may be comprised within a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Temin, 1986). The first viruses used as gene vectors were DNA viruses including the papovaviruses (simian virus 40, bovine papilloma virus, and polyoma) (Ridgeway, 1988) and adenoviruses (Ridgeway, 1988). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

4.16 Selectable Markers

In certain embodiments of the invention, the delivery of a nucleic acid in a cell may be identified in vitro or in vivo by including a marker in the expression construct. The marker would result in an identifiable change to the transfected cell permitting ready identification of expression. Usually the inclusion of a drug selection marker aids in cloning and in the selection of transformants, for example, neomycin, puromycin, hygromycin, DHFR, GPT, zeocin and histidinol. Alternatively, enzymes such as herpes simplex virus thymidine kinase (tk) (eukaryotic) or chloramphenicol acetyltransferase (CAT) (prokaryotic) may be employed, as well as markers such as green fluorescent protein, luciferase, and the like. Immunologic markers also can be employed. The selectable marker employed is not believed to be important, as long as it is capable of being expressed simultaneously with the nucleic acid encoding a gene product. Further examples of selectable markers are well known to one of skill in the art.

4.17 Multigene Constructs and IRES

In certain embodiments of the invention, the use of internal ribosome entry sites (IRES) elements are used to create multigene, with a single promoter or polycistronic, messages. IRES elements are able to bypass the ribosome scanning model of 5' methylated Cap dependent tanslation and begin translation at internal sites (Pelletier and Sonenberg, 1988; Yang et al., 1988). IRES elements from two members of the picornovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoterlenhancer to transcribe a single message.

Any heterologous open reading fiame can be linked to IRES elements. This includes genes for secreted proteins, multi-subunit proteins, encoded by independent genes, intracellular or membrane-bound proteins, selectable markers, and most importantly, sequences which are complementary to one or more regions of ACE mRNA. In this way, expression of several oligonucleotides can be simultaneously engineered into a cell with a single construct and a single selectable marker. In some embodiments, it may be desirable to specifically engineer a plurality of antisense constructs into one or more vectors for the suitable transformation of selected host cells.

4.18 In Vivo Delivery and Treatment Protocols

It may be desirable to introduce genetic constructs to cells in vivo. There are a number of ways in which nucleic acids may be introduced into cells. Several methods are outlined below.

4.18.1 Adenovirus

One of the preferred methods for in vivo delivery of one or more antisense oligonucleotide sequences involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

4.18.2 Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more of the ACE mRNA-complementary oligonucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact sequence from the recombinant virus inserts upstream from the gag, pol, and env sequence integrated in the host cell genome. However, new packaging cell lines are now available that should greatly decrease the likelihood of recombination (Markowitz et al., 1988; Hersdorffer et al., 1990).

4.18.3 Adeno-Associated Viruses

AAV (Ridgeway, 1988; Hermonat and Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs (FIG. 2). There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

There are several factors that prompted researchers to study the possibility of using rAAV as an expression vector. One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an imflammatory response. AAV therefore, represents an ideal candidate for delivery of antisense constructs in context of a gene therapy approach to treating ACE overexpression and/or hypertension in an animal (Muzyczka, 1992).

4.18.4 Other Viral Vectors as Expression Constructs

Other viral vectors may be employed as expression constructs in the present invention for the delivery of ACE mRNA-complementary oligonucleotide sequences to a host cell. Vectors derived from viruses such as vaccinia virus (Ridgeway, 1988; Coupar et al., 1988), lentiviruses, polio viruses and herpesviruses may be employed. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

4.18.5 Non-Viral Vectors

In order to effect expression of the ACE mRNA-complementary oligonucleotide antisense sequences of the present invention, the expression construct must be delivered into a cell. This delivery may be accomplished in vitro, as in laboratory procedures for transforming cells lines, or in vivo or ex vivo, as in the treatment of certain disease states, and in particular, in the treatment of hypertension and ACE-related disorders. As described above, the preferred mechanism for delivery is via viral infection where the expression construct is encapsidated in an infectious viral particle.

Once the expression construct has been delivered into the cell the nucleic acid encoding the ACE mRNA-complementary oligonucleotide antisense sequences may be positioned and expressed at different sites. In certain embodiments, the nucleic acid encoding the antisense construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct comprising one or more ACE mRNA-complementary oligonucleotide antisense sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

In a further embodiment of the invention, the expression construct comprising an ACE mRNA-complementary oligonucleotide antisense sequence may be entrapped in one or more nanocapsules, liposomes, or other lipid based DNA delivery agent. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, Eur. Pat. Appli. Publ. No. EP0273085, specifically incorporated herein by reference).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

4.19 Site-Specific Mutagenesis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or change the properties of the polynucleotide itself, and/or alter the properties, activity, composition, stability, or primary sequence of the encoded polypeptide.

In certain embodiments of the present invention, the inventors contemplate the mutagenesis of the disclosed ACE mRNA-complementary oligonucleotide antisense sequences to alter the activity or effectiveness of such antisense constructs in inhibiting or altering ACE activity in a transformed host cell. Likewise in certain embodiments, the inventors contemplate the mutagenesis of the ACE gene itself to facilitate improved regulation of the enzyme's activity in vitro and/or in vivo.

The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector which exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double-stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably reverse transcription and PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-target DNA and an internal or "middle" sequence of the target protein specific RNA is hybridized to DNA which is present in a sample. Upon hybridization, the reaction is treated with RNaseH, and the products of the probe identified as distinctive products generating a signal which are released after digestion. The original template is annealed to another cycling probe and the reaction is repeated. Thus, CPR involves amplifying a signal generated by hybridization of a probe to a target gene specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer which has sequences specific to the target sequence. Following polymerization, DNA/RNA hybrids are digested with RNase H while double stranded DNA molecules are heat denatured again. In either case the single stranded DNA is made fully double stranded by addition of second target-specific primer, followed by polymerization. The double stranded DNA molecules are then multiply transcribed by a polymerase such as T7 or SP6. In an isothermal cyclic reaction, the RNAs are reverse transcribed into DNA, and transcribed once again with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

4.20 Biological Functional Equivalents

Modification and changes may be made in the structure of the polynucleotides and polypeptides of the present invention and still obtain a functional molecule that encodes a polypeptide with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 6.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 6

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Antisense Compositions Inhibit ACE Activity

Three different oligonucleotides represented by Formula I in which B was selected such that the base sequence of the oligonucleotide is according to SEQ ID NO:4, or SEQ ID NO:5 or SEQ ID NO:6 were tested for their ability to inhibit the expression of human ACE. Human umbilical cord endothelial cells (ECV304) were incubated with each oligonucleotide for two days. The cells were lysed using 0.5% Triton® solution. The cells were homogenized and the ACE was measured by the ACE activity assay disclosed in Neels et al., 1983. The data demonstrated that each of the oligonucleotides with base sequences according to SEQ ID NO:4, SEQ ID NO:5, or SEQ ID NO:6 were effective in inhibiting ACE expression.

5.2 Example 2

Therapeutic Efficacy of ACE Antisense Compositions

The present example describes methods for utilizing ACE-specific oligonucleotide compositions as therapeutics for hypertensive animals. These studies utilized the spontaneously hypertensive rat (SHR) model, which has been used for over 30 years as a model system. This model is widely-accepted by researchers in the field as an approved animal model for studying human hypertension (Frohlich, 1986).

The animal studies were carried out to demonstrate the efficacy and time of action of ACE-specific oligonucleotide compositions. Tests were conducted in rats by i.v. injection of the antisense in a lipid carrier comprising N-[1(2,3-dioleoyloxy)propyl]N,N,N-trimethyl ammonium chloride (DOTAP) and dioleoyl phosphatidyle ethanolamine (DOPE) in a ratio of 1:1 wt./wt. DOTAP/DOPE, 2 mg/ml, to which 100 μg of each oligonucleotide composition was added to 100 μg of lipid.

The SHR rats tested weighed 225–250 g, and had systolic blood pressures of 180 mm Hg±5 mm Hg. Blood pressure was measured by tailcuff at 12 h, 1, 2, 3, and 4 days after injection. All tested ODNs were effective in reducing hypertension, with the ODN having a base sequence according to SEQ ID NO:2 producing the greatest initial decrease in blood pressure. Likewise, the ODN having a base sequence according to SEQ ID NO:1 produced the longest-lasting anti-hypertensive effect. The ODN having a base sequence according to SEQ ID NO:3 was also effective, but to a lesser degree than either of the other two ODNs.

5.3 Example 3

Long-Term Therapy Using ACE Antisense Compositions

Six SHR rats were tested using the ODN with the base sequence according to SEQ ID NO:1. For this study, SHR rats were implanted with telemetry devices to continuously record blood pressure from the aorta 24 h a day for several weeks. A baseline was established in each case for approximately 1 wk, then ACE-AS-ODN 100 μg was injected i.v. and the effect on blood pressure and heart rate observed. The effect of the antisense began between 3–6 h by producing a reduction in blood pressure of 20–30 mm Hg. The results were consistent from rat to rat (n=5). The maximum decrease in blood pressure (−40 mm Hg) occurred within 9–12 h but blood pressure remained decreased to normotensive levels for over 60 h with a single dose.

The next test was repeated injection. One week after the first treatment, a second injection with the same dose (100 μg i.v.) was given. Repeated injections showed that the blood pressure was again reduced with a second dose and that the second dose reduced blood pressure longer than the first dose (average over 120 h). Thus, there was no loss of efficacy, and no evidence of tachyphylaxis. Further, no toxicity was noted.

An example of the effectiveness of the ACE-AS (9-mer), the last 9 bases of SEQ. ID NO:1, injected i.v. in a single dose in spontaneously hypertensive rats. A total of 7 rats were injected. The rats were instrumented with telemetry recording of blood pressure which was sampled for 10 seconds, every ten minutes, continuously for over 50 days. The first example shows a typical pattern of blood pressure reduction with a single injection (3 mg/kg) of ACE-AS-ODN in the jugular vein (FIG. 1). Blood pressure fell over the next 10 days by as much as 30 mmHg. An extended recording in the rats showed that despite some lability of the blood pressure, the pretreatment levels were not reattained until 40 days after the injection.

Example 2 shows the effectiveness of ACE antisense (9-mer, 3 mg/kg) injected i.v. in SHR in groups of 7 rats (FIG. 2). There was on average, a 16±3 mmHg drop in blood pressure from a baseline average of 169 mmHg and the duration of effect lasted, on average, 15±4 days. From this experiment we conclude that ACE antisense will reduce blood pressure significantly in a model of hypertension. Secondly, the effect is long-lasting and the antisense could be injected as infrequently as once a week or once every 10 or 15 days.

In summary, these animal data demonstrated that an oligonucleotide comprising a contiguous base sequence according to SEQ ID NO:1, or 9 consecutive sequences based on SEQ ID NO:1 was an effective antihypertensive agent: a single injection (0.3 mg/kg) was effective for 3–4 days, a single injection (3 mg/kg) was effective for a mean of 15 days. Importantly, heart rate was not affected, and administration of the ODN was very well tolerated by the animal, with no apparent side effects.

The above effects of blood pressure in hypertensive rats modeling human essential hypertension was similar to that observed by the inventors previously with other antisense ODNs. This includes AT-1 receptor antisense (Phillips, 1997; Gyurko et al., 1993; Meng et al., 1994) and angiotensinogen antisense (Meng et al., 1994; Wielbo et al., 1994; Wielbo et al., 1995). Injections of these antisenses i.v. in a dose of 100 μg produce a reduction in blood pressure within 12 h and the effect lasts for 3–4 days. A second injection reduces blood pressure for a longer period of time (approximately 10 days) and the effect shows no sign of tachyphylaxis. These other ODNs have been tested for cellular uptake and found to be taken up into kidney, liver and blood vessel walls. With FITC (fluorescent label), antisense ODN was shown to be taken up by cells in these tissues and transported to the nucleus of the cell (Phillips, 1997; Gyurko et al., 1993). From this the inventors presume that the effects are in the nucleus and result in inhibition of transport of messenger RNA from the nucleus to the cytoplasm.

Currently many ACE inhibitors have been synthesized based on the original design of Cushman and Ondetti (1980) using chemical structures with sulfhydryl or other molecules that bind to $Zn^{++}$ in the metallopeptidase ACE enzyme. The drugs, such as captopril, enalapril, ramipril, cilazapril, fosinopril and others, have varying degrees of lipid solubility, and as such must be administered 1–2 times per day to be effective. They often produce side-effects including coughs and rashes (Kaplan, 1998).

The concept of antisense inhibition, using a sequence specific antisense oligonucleotide, is based on a completely different principle to the drug designs. Antisense ODN will have none of the side effects associate with a molecule that is foreign to the body. Animal studies prove that ACE-specific antisense compositions are effective in reducing blood pressure without altering heart rate, or producing side effects. The hypotensive action is longer-lasting than any current drug on the market. The reduction in blood pressure lasts for 3–4 days. Repeated application appears to prolong the antihypertensive action of the antisense. Since the aim of the treatment is to reduce an overexpressed gene, the ACE-specific antisense constructs bring expression down to normal levels and does not interfere with the physiological functions of ACE.

The inventors conclude that ACE-specific antisense compositions are beneficial as antihypertensive agents by reducing overactive effects of angiotensin II in arterial restenosis and cardiac hypertrophy. Such ACE-specific antisense compositions may be used in ways similar to current ACE inhibitors, but have the advantage of being longer-lasting, producing fewer side effects, and reducing many of the problems associated with patient compliance.

5.4 Example 4

Inhibitors of ACE mRNA Translation

Although the present invention has been described with reference to certain preferred embodiments, other variants are possible. For example, the present invention includes oligonucleotide compounds which lack a complement for each nucleotide in a particular segment of the ACE mRNA, provided such compounds have sufficient binding affinity for the ACE mRNA to inhibit expression thereof. The disclosed methods may also be modified when evaluating specific compounds for the inhibition of human ACE. For example, human cells such as human umbilical cord endothelial cells may be used for the cell culture. Also, the present invention is intended to include mixtures of oligonucleotide compounds, each compound being capable of binding to ACE mRNA.

5.5 Example 5

Long-Term Effects of Antisense Therapy

The compositions of the invention may also be tested for the effects of repeated dosing. Since the inventors have shown that a single dose of ACE-AS significantly reduces blood pressure for over 10 days in the spontaneously hypertensive rat model (SHR), groups of 10 rats may be dosed every 10 days and blood pressure continuously monitored through telemetry to establish that their blood pressure remains significantly lower than in the group either of untreated rats or the group of rats treated with ACE-sense-strand ODNs (control group). No toxic effects were observed from continuous dosing, even when ten doses are given.

In a genetic variant of SHR known as stroke prone (SHRSP), death ensues from stroke in adult SHRSP at about 27 weeks. Using repeated dosing every 10 days with ACE-AS, analyses may determine whether or not survival of SHRSP is prolonged. Control groups of untreated and sense treated rats are used for comparison. The inventors contemplate that the antisense treatment will prolong the survival of these rat models of stroke in hypertension. Since ACE inhibitors can prolong their life (Lee et al., 1994; Linz et al., 1997) and reduce kidney dysfunction and cardiac hypertrophy (Inada et al., 1995).

A further test of the prolongation of survival of SHR with antisense to ACE is a test of SHRSP on salt diet (1% NaCl) which has been shown to accelerate blood pressure increase and death in SHRSP treated from the 8th week of life. Death ensues after 5 weeks on the diet, as a consequence of cerebral hemorrhage. Groups of rats are treated either with the ACE-AS oligo or ACE-Sense or vehicle control for 5 weeks of injections every 10 days. The inventors contemplate that death will ensue in the control rats after 5 weeks, (Biagini et al., 1997) but that antisense oligonucleotide-treated rats will have much longer survival.

The effectiveness of the human sequence of ACE-AS may be tested on human coronary arteries endothelial cells and/or pulmonary endothelial cells. These arteries/cells are removed during bypass surgery and/or postmortem conducted. They may be treated with ACE-AS and control ACE-Sense, and the effect on ACE mRNA and ACE protein/ activity measured by RT-PCR and enzymatic assay, respectively. The present results indicated that the ACE-AS treatment may effectively reduce the ACE mRNA and ACE protein in these cells.

Human blood vessels removed during coronary bypass may also be tested for the uptake of human-ACE-AS by labeling the oligo with $I^{125}$ radioactive label and establishing the distribution and uptake of ACE in blood vessels by autoradiography. The blood vessels may be treated in vitro for 24 hours with either ACE-AS or ACE-S as a control.

Nasal spray or intra-lung delivery method will be tested as an alternative to i.v. injection. Longer sequences within ACE gene are inserted in the antisense orientation into the adeno-associated virus-based vector and tested as a plasmid DNA, DNA-liposomes complexes and recombinant AAV. These are used for testing in SHR, SHRSP and human endothelial cells.

A test of ACE-AS on myocardial ischemia is carried out using animals treated with ACE-AS or control ACE-Sense or vehicle 24 hr prior to ischemia (30 minutes total flow reduction to the heart), followed by reperfusion. Measures of heart function-rate, force of contraction, developing ventricular pressure are made to test that ACE-AS has a positive effect on hearts by reducing the deleterious effects of ischemia reperfusion as shown by Yang et al. (1998) using AS targeted to angiotensin type 1 receptor mRNA.

6.0 REFERENCES

The references listed below and all references cited herein are each specifically incorporated herein by reference in its entirety to the extent that they supplement, explain, provide a background for, or teach methodology, techniques, and/or compositions employed herein.

U.S. Pat. No. 4,216,209, issued Aug. 5, 1980.
U.S. Pat. No. 4,292,404, issued Sep. 29, 1981.
U.S. Pat. No. 4,335,041, issued Jun. 15, 1982.
U.S. Pat. No. 4,358,535, issued Nov. 9, 1982.
U.S. Pat. No. 4,407,944, issued Oct. 4, 1983.
U.S. Pat. No. 4,554,101, issued Nov. 19, 1985.
U.S. Pat. No. 4,683,195, issued Jul.28, 1987.
U.S. Pat. No. 4,683,202, issued Jul. 28, 1987.
U.S. Pat. No. 5,098,887, issued Mar. 24, 1992.
U.S. Pat. No. 5,145,684, issued Sep. 8, 1992.
U.S. Pat. No. 5,145,864, issued Sep. 8, 1992.
U.S. Pat. No. 5,238,921, issued Aug. 24, 1993.
U.S. Pat. No. 5,348,978, issued Sep. 20, 1994.
U.S. Pat. No. 5,359,045, issued Oct. 25, 1994.
U.S. Pat. No. 5,399,346, issued Mar. 21, 1995.
U.S. Pat. No. 5,399,363, issued Mar. 21, 1995.
U.S. Pat. No. 5,449,661, issued Sep. 12, 1995.
U.S. Pat. No. 5,466,468, issued Nov. 14, 1995.
U.S. Pat. No. 5,480,793, issued Jan. 2, 1996.
U.S. Pat. No. 5,543,158, issued Apr. 6, 1996.
U.S. Pat. No. 5,552,157, issued Sep. 3, 1996.
U.S. Pat. No. 5,552,397, issued Sep. 3, 1996.
U.S. Pat. No. 5,565,213, issued Oct. 15, 1996.
U.S. Pat. No. 5,567,434, issued Oct. 22, 1996.
U.S. Pat. No. 5,580,579, issued Dec. 3, 1996.
U.S. Pat. No. 5,591,317, issued Jan. 7, 1997.
U.S. Pat. No. 5,602,306, issued Feb. 11, 1997
U.S. Pat. No. 5,610,288, issued Mar. 11, 1997.
U.S. Pat. No. 5,639,940, issued Jun. 17, 1997
U.S. Pat. No. 5,641,515, issued Jun. 24, 1997.
U.S. Pat. No. 5,656,016, issued Aug. 12, 1997.
U.S. Pat. No. 5,663,188, issued Sep. 2, 1997.
U.S. Pat. No. 5,697,899, issued Dec. 16, 1997.
U.S. Pat. No. 5,710,134, issued Jan. 20, 1998.

U.S. Pat. No. 5,718,709, issued Feb. 17, 1998.
U.S. Pat. No. 5,720,936, issued Feb, 24, 1998
U.S. Pat. No. 5,723,307, issued Mar. 3, 1998.
U.S. Pat. No. 5,725,871, issued Mar. 10, 1998.
U.S. Pat. No. 5,738,868, issued Apr. 14, 1998.
U.S. Pat. No. 5,739,119, issued Apr. 14, 1998.
U.S. Pat. No. 5,741,516, issued Apr. 21, 1998.
U.S. Pat. No. 5,744,496, issued Apr. 28, 1998.
U.S. Pat. No. 5,747,470, issued May 5, 1998.
U.S. Pat. No. 5,756,353, issued May 26, 1998.
U.S. Pat. No. 5,759,829, issued Jun. 2, 1998.
U.S. Pat. No. 5,770,219, issued Jun. 23, 1998.
U.S. Pat. No. 5,779,708, issued Jul. 14, 1998.
U.S. Pat. No. 5,780,045, issued Jul. 14, 1998.
U.S. Pat. No. 5,783,208, issued Jul. 21, 1998.
U.S. Pat. No. 5,783,683, issued Jul. 21, 1998.
U.S. Pat. No. 5,789,573, issued Aug. 4, 1998.
U.S. Pat. No. 5,789,655, issued Aug. 4, 1998
U.S. Pat. No. 5,792,451, issued Aug. 11, 1998.
U.S. Pat. No. 5,795,587, issued Aug. 18, 1998.
U.S. Pat. No. 5,797,898, issued Aug. 25, 1998.
U.S. Pat. No. 5,800,990, issued Sep. 1, 1998.
U.S. Pat. No. 5,801,040, issued Sep. 1, 1998.
U.S. Pat. No. 5,801,154, issued Sep. 1, 1998
U.S. Pat. No. 5,804,212, issued Sep. 8, 1998.
Intl. Pat. Appl. No. WO 90/03435.
Adams et al., *J. Am. Chem. Soc.,* 105:661, 1983.
Agarwal and Riftina, "Synthesis and enzymatic properties of deoxyribooligonucleotides containing methyl and phenylphosphonates linkages," *Nucl. Acids Res.,* 6(9): 3009–3023, 1979.
Agodoa, "African American study of kidney disease and hypertension (AASK)—clinical trial update," *Ethn. Dis.,* 8(2):249–253, 1998.
Alderman, Madhavan, Ooi, Cohen, Sealey, Laragh, "Association of the renin-sodium profile with the risk of myocardial infarction in patients with hypertension," *New Eng. J. Med.,* 324(16):1098–1104, 1991.
Allen and Choun, "Large unilamellar liposomes with low uptake into the reticuloendothelial system," *FEBS Lett.,* 223:42–46, 1987.
Altschul et al., "Gapped BLAST and PSI-BLAST: a new generation of protein database search programs," *Nucl. Acids Res.,* 25:3389–3402, 1997.
Armitage, Koch, Frydenlund, Orum, Batz, Schuster, "Peptide nucleic acid-anthraquinone conjugates: strand invasion and photoinduced cleavage of duplex DNA," *Nucl. Acids Res.,* 25(22):4674–4678, 1997.
Armitage, Ly, Koch, Frydenlund, Orum, Batz, Schuster, "Peptide nucleic acid-DNA duplexes: long range hole migration from an internally linked anthraquinone," *Proc. Natl. Acad. Sci. USA,* 94(23):12320–12325, 1997.
Asseline and Thuong, *Tetrahedron Lett.,* 30(19):2521–2524, 1989.
Balazsovits et al., "Analysis of the effect of liposome encapsulation on the vesicant properties, acute and cardiac toxicities, and antitumor efficacy of doxorubicin," *Cancer Chemother. Pharmacol.,* 23:81–86, 1989.
Benvenisty and Reshef, "Direct introduction of genes into rats and expression of the genes," *Proc. Natl. Acad. Sci. USA.;* 83(24): 9551–9555, 1986.
Biagini G., Zoli, M., Toni, C., Boschi, S. Vantaggiato, G., Ballestri, M., Baraldi, A., Agnati, L. F. Protective effects of delapril, indapamide and their combination chronically administered to stroke-prone spontaneously hypertensive rats fed a high-sodium diet *Clin. Sci.* (Colch) 93(5): 401–411, 1997.
Boffa, "Thrombomodulin in human brain microvasculature," *Lupus,* 4(2):165–166, 1995.
Boffa, Berard, Sugi, McIntyre, "Antiphosphatidylethanolamine antibodies as the only antiphospholipid antibodies detected by ELISA.II. Kininogen reactivity," *J. Rheumatol.,* 23(8):1375–1379, 1996.
Bonham, Brown, Boyd, Brown, Bruckenstein, Hanvey, Thomson, Pipe, Hassman, Bisi, et al., "An assessment of the antisense properties of Rnase H-competent and steric-blocking oligomers," *Nucl. Acids Res.,* 23(7):1197–1203, 1995.
Bourlais, Acar, Zia, Sado, Needham, Leverge, "Ophthalmic drug delivery systems—recent advances," *Prog. Retin Eye Res.,* 17(1):33–58, 1998.
Broido et al., *Biochem. Biophys. Res. Commun.,* 119:663, 1984.
Caldovic and Hackett Jr., "Development of position-independent expression vectors and their transfer into transgenic fish," *Mol. Mar. Biol. Biotechnol.,* 4(1):51–61, 1995.
Capecchi, "High efficiency transformation by direct microinjection of DNA into cultured mammalian cells," *Cell,* 22(2):479–488, 1980.
Carlsson, Sandler, Jansson, "Influence of the neurotoxin capsaicin on rat pancreatic islets in culture, and on the pancreatic islet blood flow of rats," *Eur. J Pharmacol.,* 312(1):75–81, 1996.
Caruthers et al., In: *Genetic Engineering,* Settlow and Hollander (Eds.), Plenum Press, New York, 1982.
Carver, Dalrymple, Wright, Cottom, Reeves, Gibson, Keenan, Barrass, Scott, Colman, et al., "Transgenic livestock as bioreactors: stable expression of human alpha-1-antitrypsin by a flock of sheep," *Biotechnology NY,* 11(11):1263–1270, 1993.
Chamorro, Vila, Ascaso, Elices, Schonewille, Blanc, "Blood pressure and functional recovery in acute ischemic stroke," *Stroke,* 29(9):1850–1853, 1998.
Chandran, Roy, Mishra, "Recent trends in drug delivery systems: liposomal drug delivery system—preparation and characterisation," *Indian J. Exp. Biol.,* 35(8): 801–809, 1997.
Chang et al., "Foreign gene delivery and expression in hepatocytes using a hepatitis B virus vector," *Hepatology,* 14:134A, 1991.
Chen and Okayama, "High-efficiency transformation of mammalian cells by plasmid DNA," *Mol. Cell. Biol.,* 7:2745–2752, 1987.
Christensen, Johansen, Marker, Thomsen, "Circulating intracellular adhesion molecule-1 (ICAM-1) as an early and sensitive marker for virus-induced T cell activation," *Clin. Exp. Immunol.,* 102(2):268–273, 1995.
Coffin, "Retroviridae and their replication," In: *Virology,* Fields et al. (eds.), New York: Raven Press, pp. 1437–1500, 1990.
Cohen, "Designing antisense oligonucleotides as pharmaceutical agents," *Trends Pharmacol. Sci.,* 10(11): 435–437, 1989.
Corey, "Peptide nucleic acids: expanding the scope of nucleic acid recognition," *Trends Biotechnol.,* 15(6): 224–229, 1997.
Couch et al., "Immunization with types 4 and 7 adenovirus by selective infection of the intestinal tract," *Am. Rev. Resp. Dis.,* 88:394–403, 1963.
Coune, "Liposomes as drug delivery system in the treatment of infectious diseases: potential applications and clinical experience," *Infection,* 16(3):141–147, 1988.
Coupar et al., "A general method for the construction of recombinant vaccinia virus expressing multiple foreign genes," *Gene,* 68:1–10, 1988.

Couvreur, "Polyalkyleyanoacrylates as colloidal drug carriers," *Crit. Rev. Ther. Drug Carrier Syst.,* 5:1–20, 1988.

Couvreur et al., "Nanocapsules, a new lysosomotropic carrier," *FEBS Lett.,* 84:323–326, 1977.

Couvreur et al., "Tissue distribution of antitumor drugs associated with polyalkylcyanoacrylate nanoparticles," *J. Pharm. Sci.,* 69(2):199–202, 1980.

Cozzi, Tucker, Langford, Pino-Chavez, Wright, O'Connell, Young, Lancaster, McLanghlin, Hunt, Bordin, White, "Characterization of pigs transgenic for human decay-accelerating factor," *Transplantation,* 64(10):1383–1392, 1997.

Curiel, Agarwal, Wagner, Cotten, "Adenovirus enhancement of transferrin-polylysine-mediated gene delivery," *Proc. Natl. Acad. Sci. USA,* 88(19):8850–8854, 1991.

Cushman and Ondetti, "Inhibitors of ACE for treatment of hypertension," *Biochem. Pharmacol.,* 19:1871, 1980.

De Mesmaeker et al., "Antisense oligonucleotides," *Acc. Chem. Res.,* 28:366–374, 1995.

Deira, Corbacho, Bondia, Lerma, Gascon, Martin, Garcia, Tabernero, "Captopril hepatotoxicity in a case of renal crisis due to systemic sclerosis," *Nephrol. Dial. Transplant,* 12(8):1717–1718, 1997.

Douglas, Davis, Illum, "Nanoparticles in drug delivery," *Crit. Rev. Ther. Drug Carrier Syst.,* 3(3):233–261, 1987.

Dubensky et al., "Direct transfection of viral and plasmid DNA into the liver or spleen of mice," *Proc. Nat. Acad. Sci. USA,* 81:7529–7533, 1984.

Dueholm, Motawia, Pedersen, Nielsen, Lundt, "Synthesis of 3'-alkylthio-2',3'-dideoxy nucleosides with potential anti-HIV activity from 2-deoxy-D-ribose, using a phosphorus pentoxide reagent," *Arch. Pharm. (Weinheim),* 325(9):597–601, 1992.

Dzau, "Vascular renin-angiotensin system and vascular protection," *J. Cardiovasc. Pharmacol.,* 22(Suppl.) 5:S1–S9, 1993.

Ebert, Selgrath, DiTullio, Denman, Smith, Memon, Schindler, Monastersky, Vitale, Gordon, "Transgenic production of a variant of human tissue-type plasminogen activator in goat milk: generation of transgenic goats and analysis of expression," *Biotechnology NY,* 9(9):835–838, 1991.

Egholm, Buchardt, Christensen, Behrens, Freier, Driver, Berg, Kim, Norden, Nielsen, "PNA hybridizes to complementary oligonucleotides obeying the Watson-Crick hydrogen-bonding rules," *Nature,* 365(6446):566–568, 1993.

Eglitis and Anderson, "Retroviral vectors for introduction of genes into mammalian cells," *Biotechniques* 6(7):608–614, 1988.

Eglitis, Kantoff, Kohn, Karson, Moen, Lothrop, Blaese, Anderson, "Retroviral-mediated gene transfer into hemopoietic cells," *Avd. Exp. Med. Biol.,* 241:19–27, 1988.

Faller and Baltimore, "Liposome encapsulation of retrovirus allows efficient super infection of resistant cell lines," *J. Virol.,* 49(1):269–272, 1984.

Fechheimer et al., "Transfection of mammalian cells with plasmid DNA by scrape loading and sonication loading," *Proc. Natl. Acad. Sci. USA,* 84:8463–8467, 1987.

Ferkol, Lindberg, Chen, Perales, Crawford, Ratnoff, Hanson, "Regulation of the phosphoenolpyruvate carboxykinase/human factor IX gene introduced into the livers of adult rats by receptor-mediated gene transfer," *FASEB J.,* 7(11):1081–1091, 1993.

Footer, Egholm, Kron, Coull, Matsudaira, "Biochemical evidence that a D-loop is part of a four-stranded PNA-DNA bundle. Nickel-mediated cleavage of duplex DNA by a Gly-Gly-His bis-PNA," *Biochemistry,* 35(33):10673–10679, 1996.

Fraley et al., "Entrapment of a bacterial plasmid in phospholipid vesicles: Potential for gene transfer," *Proc. Natl. Acad. Sci. USA,* 76:3348–3352, 1979.

Franz, Mueller, Haartong, Frey, Katus, "Transgenic animal models: new avenues in cardiovascular physiology," *J. Mol. Med.,* 75(2):115–119, 1997.

Fresat and Puglisi, "Application of liposomes as potential cutaneous drug delivery systems. In vitro and in vivo investigation with radioactively labelled vesicles," *J. Drug Target,* 4(2):95–101, 1996.

Friedmann, "Progress toward human gene therapy," *Science,* 244:1275–1281, 1989.

Frohlich, *Hypertension,* 4(Suppl.):S15–S19, 1986.

Frohman, Downs, Kashio, Brinster, "Tissue distribution and molecular heterogeneity of human growth hormone-releasing factor in the transgenic mouse," *Endocrinology,* 127(5):2149–2156, 1990.

Fromm, Taylor, Walbot, "Expression of genes transferred into monocot and dicot plant cells by electroporation," *Proc. Natl. Acad. Sci. USA,* 82(17):5824–5828, 1985.

Gabizon and Papahadjopoulos, "Liposomes formulations with prolonged circulation time in blood and enhanced uptake by tumors," *Proc. Natl. Acad. Sci. USA,* 85:6949–6953, 1988.

Gambacorti-Passerini, Mologni, Bertazzoli, le Coutre, Marchesi, Grignani, Nielsen, "In vitro transcription and translation inhibition by anti-promyelocytic leukemia (PML)/retinoic acid receptor alpha and anti-PML peptide nucleic acid," *Blood,* 88(4):1411–1417, 1996.

Ghosh-Choudhury et al., "Protein IX, a minor component of the human adenovirus capsid, is essential for the packaging of full-length genomes," *EMBO J.,* 6:1733–1739, 1987.

Ghosh and Bachhawat, "Targeting of liposomes to hepatocytes," In: *Liver diseases, targeted diagnosis and therapy using specific receptors and ligands,* Wu G. and C. Wu ed., New York: Marcel Dekker, pp. 87–104, 1991.

Goldstein and Doi, "Prokaryotic promoters in biotechnology," *Biotechnol. Annu. Rev.,* 1:105–128, 1995.

Gomez-Foix et al., "Adenovirus-mediated tranfer of the muscle glycogen phosphorylase gene into hepatocytes confers altered regulation of glycogen metabolism," *J. Biol. Chem.,* 267(35):25129–25134, 1992.

Good and Nielsen, "Progress in developing PNA as a gene-targeted drug," *Antisense Nucl. Acid Drug Dev.,* 7(4):431–437, 1997.

Gopal, "Gene transfer method for transient gene expression, stable transfection, and cotransfection of suspension cell cultures," *Mol. Cell Biol.,* 5:1188–1190, 1985.

Graham and Prevec, "Manipulation of adenovirus vector," In: *Methods in Molecular Biology: Gene Transfer and Expression Protocol,* E. J. Murray (ed.), Clifton, N.J.: Humana Press, 7:109–128, 1991.

Graham and Prevec, "Adenovirus-based expression vectors and recombinant vaccines," *Biotechnology,* 20:363–390, 1992.

Graham and van der Eb, "Transformation of rat cells by DNA of human adenovirus 5," *Virology,* 54(2):536–539, 1973.

Graham et al., "Characteristics of a human cell line transformed by DNA from human adenovirus type 5", *J. Gen. Virol.,* 36:59–72, 1977.

Gribskov and Burgess, Nucl. Acids Res. 14:6745, 1986, as described by Schwartz and Dayhoff, eds., In: *Atlas of*

*Protein Sequence and Structure,* National Biomedical Research Foundation, pp. 353–358, 1979.

Grunhaus and Horwitz, "Adenovirus as cloning vector," *Sem. in Virol.,* 3:237–252, 1992.

Gyurko, Tran, Phillips, "Time course of inhibition of hypertension by antisense oligonucleotides targeted to $AT_1$ angiotensin receptor mRNA in spontaneously hypertensive rats," *Am. J. Hypertens.,* 10:565–625, 1997.

Gyurko, Wielbo, Phillips, "Antisense inhibition of $AT_1$ receptor mRNA and angiotensinogen mRNA in the brain of spontaneously hypertensive rats reduces hypertension of neurogenic origin," *Reg. Pep.,* 49(2):167–174, 1993.

Haaima, Hansen, Christensen, Daho, Nielsen, "Increased DNA binding and sequence discrimination of PNA oligomers containing 2,6-diaminopurine," *Nucl. Acids Res.,* 25(22):4639–4643, 1997.

Hanvey, Peffer, Bisi, Thomson, Cadilla, Josey, Ricca, Hassman, Bonham, Au, et al., "Antisense and antigene properties of peptide nucleic acids," *Science,* 258(5087):1481–1485, 1992.

Harland and Weintraub, "Translation of mammalian mRNA injected into Xenopus oocytes is specifically inhibited by antisense RNA," *J. Cell Biol.,* 101:1094–1099, 1985.

Haskell and Bowen, "Efficient production of transgenic cattle by retroviral infection of early embryos," *Mol. Reprod. Dev.,* 40(3):386–390, 1995.

Heath and Martin, "The development and application of protein-liposome conjugation techniques," *Chem. Phys. Lipids,* 40:347–358, 1986.

Heath et al., "Liposome-mediated delivery of pteridine antifolates to cells: in vitro potency of methotrexate and its alpha and gamma substituents," *Biochim. Biophys. Acta,* 862:72–80, 1986.

Henry-Michelland et al., "Attachment of antibiotics to nanoparticles; Preparation, drug-release and antimicrobial activity in vitro," *Int. J. Pharm.,* 35:121–127, 1987.

Hermonat and Muzyczka, "Use of adenoassociated virus as a mammalian DNA cloning vector: Transduction of neomycin resistance into mammalian tissue culture cells," *Proc. Natl. Acad. Sci. USA,* 81:6466–6470, 1984.

Hersdorffer et al., "Efficient gene transfer in live mice using a unique retroviral packaging line," *DNA Cell Biol.,* 9:713–723, 1990.

Herz and Gerard, "Adenovirus-mediated transfer of low density lipoprotein receptor gene acutely accelerates cholesterol clearance in normal mice," *Proc. Natl. Acad. Sci. USA* 90:2812–2816, 1993.

Hoover et al., (Eds.), "Remington's Pharmaceutical Sciences," 15th Edition, Mack Publishing Co., Easton, Pa., 1975.

Horwich et al. "Synthesis of hepadenovirus particles that contain replication-defective duck hepatitis B virus genomes in cultured HuH7 cells," *J. Virol.,* 64:642–650, 1990.

Hwang, Park, Park, "Gastric retentive drug-delivery systems," *Crit. Rev. Ther. Drug Carrier Syst.,* 15(3):243–284, 1998.

Hyrup and Nielsen, "Peptide nucleic acids (PNA): synthesis, properties and potential applications," *Bioorg. Med. Chem.,* 4(1):5–23, 1996.

Imaizumi et al., "Liposome-entrapped superoxide dismutase reduces cerebral infarction in cerebral ischemia in rats," *Stroke,* 21(9):1312–1317, 1990a.

Imaizumi et al., "Liposome-entrapped superoxide dismutase ameliorates infarct volume in focal cerebral ischemia," *Acta. Neurochirurgica Suppl.,* 51:236–238, 1990b.

Inada, Y., Ojima, M., Itoh, K., Shino, A., Nishikawa, K. Effects of delapril on stroke, kidney dysfunction and cardiac hypertrophy in stroke-prone spontaneously hypertensive rats. *Drugs Exp. Clin. Res.* 21(2):41–49, 1995.

Jaskulski, deRiel, Mercer, Calabretta, Baserga, "Inhibition of cellular proliferation by antisense oligodeoxynucleotides to PCNA cyclin," *Science,* 240(4858):1544–1546, 1988.

Jensen and Pedersen, "Nocturnal blood pressure and relation to vasoactive hormones and renal function in hypertension and chronic renal failure," *Blood Press.,* 6(6):332–342, 1997.

Jones and Shenk, "Isolation of deletion and substitution mutants of adenovirus type 5," *Cell,* 13:181–188, 1978.

Kaneda, Iwai, Uchida, "Introduction and expression of the human insulin gene in adult rat liver," *J. Biol. Chem.,* 264(21):12126–12129, 1989.

Kang, Cho, Kole, "Up-regulation of luciferase gene expression with antisense oligonucleotides: implications and applications in functional assay development," *Biochemistry,* 37(18):6235–6239, 1998.

Karlsson, Van Doren, Schweiger, Nienhuis, Gluzman, "Stable gene transfer and tissue-specific expression of a human globin gene using adenoviral vectors," *EMBO J.,* 5(9):2377–2385, 1986.

Kato et al., "Expression of hepatitis β virus surface antigen in adult rat liver," *J. Biol. Chem.,* 266:3361–3364, 1991.

Kettel, Murphy, Morales, Ulmann, Baulieu, Yen, "Treatment of endometriosis with the antiprogesterone mifepristone," *Fertil. Steril.,* 65(1):23–28, 1996.

Klein, Kornstein, Sanford, Fromm, *Nature,* 327:70–73, 1987.

Klein, Wolf, Wu, Sanford, "High-velocity microprojectiles for delivering nucleic acids into living cells. 1987," *Biotechnology,* 24:384–386, 1992.

Koike, Krieger, Jacob, Mukoyama, Pratt, Dzau, "Angiotensin converting enzyme and genetic hypertension: cloning of rat cDNAs and characterization of the enzyme," *Biochem. Biophys. Res. Commun.,* 198(1):380–386, 1994.

Koppelhus, Zachar, Nielsen, Liu, Eugen-Olsen, Ebbesen, "Efficient in vitro inhibition of HIV-1 gag reverse transcription by peptide nucleic acid (PNA) at minimal ratios of PNA/RNA," *Nucl. Acids Res.,* 25(11):2167–2173.

Kremsky, Wooters, Dougherty, Meyers, Collins, Brown, "Immobilization of DNA via oligonucleotides containing an aldehyde or carboxylic acid group at the 5' terminus," *Nucl. Acids Res.,* 15(7):2891–2909, 1987.

Kuby, *In: Immunology,* 2nd Edition. W.H. Freeman & Company, New York, 1994.

Kwoh, Davis, Whitfield, Chappelle, DiMichele, Gingeras, "Transcription-based amplification system and detection of amplified human immunodeficiency virus type 1 with a bead-based sandwich hybridization format," *Proc. Natl. Acad. Sci. USA,* 86(4):1173–1177, 1989.

Kyte and Doolittle, "A simple method for displaying the hydropathic character of a protein," *J. Mol. Biol.,* 157(1):105–132, 1982.

Lasic, "Novel applications of liposomes," *Trends Biotechnol.,* 16(7):307–321, 1998.

Le Gal La Salle et al., "An adenovirus vector for gene transfer into neurons and glia in the brain," *Science,* 259:988–990, 1993.

Lee, Wang, Smeda, "Effects of perindopril on hypertension and stroke prevention in experimental animals," *Can. J. Cardiol.* 10 (Suppl D):33D–36D, 1994.

Linz, Jessen, Becker, Scholkens, Wiemer, "Long-term ACE inhibition doubles lifespan of hypertensive rats," *Circulation* 96(9):3164–3172, 1997.

Lopez-Berestein et al., "Liposomal amphotericin B for the treatment of systemic fungal infections in patients with cancer: a preliminary study" *J. Infect. Dis.,* 2151:704, 1985a.

Lopez-Berestein et al., "Protective effect of liposomal-amphotericin B against *C. albicans* infection in mice," *Cancer Drug Delivery,* 2:183, 1985b.

Lu, Xiao, Clapp, Li, Broxmeyer, "High efficiency retroviral mediated gene transducion into single isolated immature and replatable CD34(3+) hematopoietic stem/progenitor cells from human umbilical cord blood," *J. Exp. Med.,* 178(6):2089–2096, 1993.

Macejak and Sanow, "Internal initiation of translation mediated by the 5' leader of a cellular mRNA," *Nature,* 353:90–94, 1991.

Maloy et al., *In: Microbial Genetics,* 2nd Edition, Jones and Barlett Publishers, Boston, Mass., 1994.

Maniatis et al., "Molecular Cloning: a Laboratory Manual," Cold Spring Harbor Laboratory, Cold Spring Harbor, N.Y., 1982.

Mann et al., "Construction of a retrovirus packaging mutant and its use to produce helper-free defective retrovirus," *Cell,* 33:153–159, 1983.

Margalit, "Liposome-mediated drug targeting in topical and regional therapies," *Crit. Rev. Ther. Drug Carrier Syst.,* 12(2–3):233–261, 1995.

Markowitz et al., "A safe packaging line for gene transfer: Separating viral genes on two different plasmids," *J. Virol.,* 62:1120–1124, 1988.

Mathiowitz, Jacob, Jong, Carino, Chickering, Chaturvedi, Santos, Vijayaraghavan, Montgomery, Bassett, Morrell, "Biologically erodable microspheres as potential oral drug delivery systems," *Nature,* 386(6623):410–414, 1997.

Menefee, Chesson, Wall, "Stress urinary incontinence due to prescription medications: alpha-blockers and angiotensin converting enzyme inhibitors," *Obstet. Gynecol.,* 91(5 Pt 2):853–854, 1998.

Meng, Wielbo, Gyurko, Phillips, "$AT_1$ receptor mRNA antisense oligonucleotide inhibits central angiotensin induced thirst and vasopressin," *Reg. Pep.,* 54:543–551, 1994.

Mollegaard, Buchardt, Egholm, Nielsen, "Peptide nucleic acid.DNA strand displacement loops as artificial transcription promoters," *Proc. Natl. Acad. Sci. USA,* 91(9): 3892–3895, 1994.

Mori and Fukatsu, "Anticonvulsant effect of DN-1417 a derivative of thyrotropin-releasing hormone and liposome-entrapped DN-1417 on amygdaloid-kindled rats," *Epilepsia,* 33(6):994–1000, 1992.

Morris et al., "A new peptide vector for effcient delivery of oligonucleotides into mamalain cell," *Nucleic Acids Res.,* 25(14):2730–2736, 1997

Moser, "Why are physicians not prescribing diuretics more frequently in the management of hypertension?," *JAMA,* 279(22):1813–1816, 1998.

Muller et al., "Efficient transfection and expression of heterologous genes in PC12 cells," *Cell, Biol.,* 9(3):221–229, 1990.

Mulligan, "The Basic Science of Gene Therapy," *Science,* 260:926–932, 1993.

Muzyczka, "Use of adeno-associated virus as a general transduction vector for mammalian cells," *In: Current Topics in Microbiology and Immunology,* Springer-Verlag, Berlin, 158:97–129, 1992.

Muzyczka and McLaughlin, "Use of adeno-associated virus as a mamalian transduction vector," *In: Current Communications in Molecular Biology: Viral Vectors,* Glzman and Hughes, eds., Cold Spring Harbor Laboratory Press, Cold Spring Harbor, N.Y., 1988:39–44.

Needleman and Wunsch, *J. Mol. Biol.,* 48:443, 1970, as revised by Smith and Waterman, Adv. Appl. Math. 2:482, 1981.

Neels et al., "Sensitive colorimetric assay for angiotensin converting enzyme in serum," *Clin. Chem.,* 29(7): 1399–1403, 1983.

Nerurkar, Rose, Stobaugh, Borchardt, "Selective fluorogenic derivatization of a peptide nucleic acid trimer with naphthalene-2,3-dicarboxaldehyde," *J. Pharm. Biomed. Anal.,* 15(7):945–950, 1997.

Nicholls, Richards, Agarwal, "The importance of the renin-angiotensin system in cardiovascular disease," *J. Hum. Hypertens,* 12(5):295–299, 1998.

Nicolas and Rubinstein, "Retroviral vectors," *In: Vectors: A survey of molecular cloning vectors and their uses,* Rodriguez and Denhardt (eds.), Stoneham: Butterworth, pp. 494–513, 1988.

Nicolau and Gersonde, "Incorporation of inositol hexaphosphate into intact red blood cells, I. fusion of effector-containing lipid vesicles with erythrocytes," *Naturwissenschaften* (Germany), 66(11):563–566, 1979.

Nicolau and Sene, "Liposome-mediated DNA transfer in eukaryotic cells," *Biochem. Biophys. Acta,* 721:185–190, 1982.

Nicolau et al, "Liposomes as carriers for in vivo gene transfer and expression," *Methods Enzymol.,* 149:157–176, 1987.

Nielsen, DiGiovanni, Christensen, Knepper, Harris, "Cellular and subcellular immunolocalization of vasopressin-regulated water channel in rat kidney," *Proc. Natl. Acad. Sci. USA,* 90(24):11663–11667, 1993.

Norton, Piatyszek, Wright, Shay, Corey, "Inhibition of human telomerase activity by peptide nucleic acids," *Nat. Biotechnol.,* 14(5):615–619, 1996.

Norton, Waggenspack, Varnum, Corey, "Targeting peptide nucleic acid-protein conjugates to structural features within duplex DNA," *Bioorg. Med. Chem.,* 3(4):437–445, 1995.

Ohara, Dort, Gilbert, "One-sided polymerase chain reaction: the amplification of cDNA," *Proc. Natl. Acad. Sci. USA,* 86(15):5673–5677, 1989.

Ono, Hirose, Miyazaki, Yamamoto, Matsumoto, "Transgenic medaka fish bearing the mouse tyrosinase gene: expression and transmission of the transgene following electroporation of the orange-colored variant," *Pigment Cell Res.,* 10(3):168–175, 1997.

Orum, Nielsen, Egholm, Berg, Buchardt, Stanley, "Single base pair mutation analysis by PNA directed PCR™ clamping," *Nucl. Acids Res.,* 21(23):5332–5336, 1993.

Orum, Nielsen, Jorgensen, Larrson, Stanley, Koch, "Sequence-specific purification of nucleic acids by PNA-controlled hybrid selection," *Biotechniques,* 19(3): 472–480, 1995.

Pardridge, Boado, Kang, "Vector-mediated delivery of a polyamide ("peptide") nucleic acid analogue through the blood-brain barrier in vivo," *Proc. Natl. Acad. Sci. USA,* 92(12):5592–5596, 1995.

Paskind et al., "Dependence of moloney murine leukemia virus production on cell growth," *Virology,* 67:242–248, 1975.

Pelletier and Sonenberg, "Internal initiation of translation of eukaryotic mRNA directed by a sequence derived from poliovirus RNA," *Nature,* 334:320–325, 1988.

Perales et al., *Proc. Natl. Acad. Sci. USA,* 91:4086–4090, 1994.

Peris, Jung, Resnick, Walker, Malakhova, Bokrand, Wielbo, "Antisense inhibition of striatal $GABA_A$ receptor proteins decreases GABA-stimulated chloride uptake and increases cocaine sensitivity in rats," *Mol. Brain Res.,* 57:310–312, 1998.

Perry-O'Keefe, Yao, Coull, Fuchs, Egholm, "Peptide nucleic acid pre-gel hybridization: an alternative to southern hybridization," *Proc. Natl. Acad. Sci. USA*, 93(25): 14670–14675, 1996.

Phillips, "Antisense inhibition and adeno-associated viral vector delivery for reducing hypertension," *Hypertension*, 29(2):177–187, 1997.

Phillips and Gyurko, "Antisense oligonucleotides: New tools for physiology," *News Physiol. Sci.*, 12:99–105, 1997.

Phillips, Wielbo, Gyurko, "Anitsense inhibiiton of hypertension: a new strategy for renin-angiotensin candidate genes," *Kidney International*, 46:1554–1556, 1994.

Pikul et al., "In vitro killing of melanoma by liposome-delivered intracellular irradiation, *Arch Surg.*, 122(12): 1417–1420, 1987.

Pinto-Alphandary, Balland, Couvreur, "A new method to isolate polyalkylcyanoacrylate nanoparticle preparations," *J. Drug Target*, 3(2):167–169, 1995.

Pinto-Sietsma and Paul, "Transgenic rats as models for hypertension," *J. Hum. Hypertens.*, 11(9):577–581, 1997.

Potter et al., "Enhancer-dependent expression of human κ immunoglobulin genes introduced into mouse pre-B lymphocytes by electroporation," *Proc. Natl. Acad. Sci. USA*, 81:7161–7165, 1984.

Powell, Clozel, Muller, Kuhn, Hefti, Hosang, Baumgartner, "Inhibitors of angiotensin converting-enzyme prevent myointimal proliferation after vascular injury," *Science*, 245:186–188, 1989.

Prokop and Bajpai, "Recombinant DNA Technology I," Conference on Progress in Recombinant DNA Technology Applications, Potosi, MI, June 3–8, 1990, *Ann. N.Y Acad. Sci.*, 646:1–383, 1991.

Quintanar-Guerrero, Allemann, Doelker, Fessi, "Preparation and characterization of nanocapsules from preformed polymers by a new process based on emulsification-diffusion techinque," *Phamr. Res.*, 15(7):1056–1062, 1998.

Racher et al., *Biotechnology Techniques*, 9:169–174, 1995.

Ragot et al., "Efficient adenovirus-mediated transfer of a human minidystrophin gene to skeletal muscle of mdx mice," *Nature*, 361:647–650, 1993.

Renan, "Cancer genes: current status, future prospects, and applicants in radiotherapy/oncology," *Radiother. Oncol.*, 19:197–218, 1990.

Renneisen et al., "Inhibition of expression of human immunodeficiency virus-1 in vitro by antibody-targeted liposomes containing antisense RNA to the env region," *J. Biol. Chem.*, 265(27):16337–16342, 1990.

Rich et al., "Development and analysis of recombinant adenoviruses for gene therapy of cystic fibrosis," *Hum. Gene Ther.*, 4:461–476, 1993.

Ridgeway, "Mammalian expression vectors," *In: Vectors: A survey of molecular cloning vectors and their uses*, Rodriguez R L, Denhardt D T, ed., Stoneham: Butterworth, pp. 467–492, 1988.

Rippe et al., "DNA-mediated gene transfer into adult rat hepatocytes in primary culture," *Mol. Cell Biol.*, 10:689–695, 1990.

Rodgers, "Combination drug therapy in hypertension: a rational approach for the pharmacist," *J. Am. Pharm. Assoc.*, 38(4):469–479, 1998.

Rosenfeld et al., "Adenovirus-mediated transfer of a recombinant a1-antitrypsin gene to the lung epithelium in vivo," *Science*, 252:431–434, 1991.

Rosenfeld et al., "In vivo transfer of the human cystic fibrosis transmembrane conductance regulator gene to the airway epithelium," *Cell*, 68:143–155, 1992.

Rosenthal, "Drug therapy of renovascular hypertension," *Drugs*, 45(6):895–909, 1993.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Sadeck, Fernandes, Silva, Trindade, Chia, Ramos, Leone, "Captopril use in pregnancy and its effects on the fetus and the newborn: case report," (Article in Portugese), *Rev. Hosp. Clin. Fac. Med. Sao Paulo*, 52(6):328–332, 1997.

Schwab, Chavany, Duroux, Goubin, Lebeau, Helene, Saison-Behmoaras, "Antisense oligonucleotides adsorbed to polyalkylcyanoacrylate nanoparticles specifically inhibit mutated Ha-ras-mediated cell proliferation and tumorigenicity in nude mice," *Proc. Natl. Acad. Sci. USA*, 91(22):10460–10464, 1994.

Sculier et al., "Pilot study of amphotericin B entrapped in sonicated liposomes in cancer patients with fungal infections," *J. Cancer Clin. Oncol.*, 24(3):527–538, 1988.

Seeger, Batz, Orum, "PNA-mediated purification of PCR™ amplifiable human genomic DNA from whole blood," *Biotechniques*, 23(3):512–517, 1997.

Segal, "Biochemical Calculations" 2nd Edition. John Wiley & Sons, New York, 1976.

Stallworth and Waldron, "Cortical blindness as a complication of acute glomerulonephritis," J.S.C. Med. Assoc., 93(3):99–101, 1997.

Stec et al., *J. Am. Chem. Soc.*, 106:6077–6079, 1984.

Stein et al., *Gene*, 72:333–341, 1988.

Stetsenko, Perchnko, Ivchenki, Kit, Petrova, Bahlikova, "The use of microwave resonance therapy in the health-resort treatment of peptic ulcer," *Lik Sprava*, 1–2:119–120, 1996.

Stratford-Perricaudet et al., "Evaluation of the transfer and expression in mice of an enzyme-encoding gene using a human adenovirus vector," *Hum. Gene Ther.*, 1:241–256, 1990.

Stratford-Perricaudet and Perricaudet, "Gene transfer into animals: the promise of adenovirus," p. 51–61, *In: Human Gene Transfer*, Eds, O. Cohen-Haguenauer and M. Boiron, Editions John Libbey Eurotext, France, 1991.

Suzuki, Shin, Fjuikura, Matsuzaki, Takata, "Direct gene transfer into rat liver cells by in vivo electroporation," *FEBS Lett.*, 425(3):436–440, 1998.

Takakura, "Drug delivery systems in gene therapy," *Nippon Rinsho*, 56(3):691–695, 1998.

Takenaga, Serizawa, Azechi, Ochiai, Kosaka, Igarashi, Mizushima, "Microparticle resins as a potential nasal drug delivery system for insulin," *J. Controller Release*, 52(1–2):81–87, 1998.

Temin, "Retrovirus vectors for gene transfer: Efficient integration into and expression of exogenous DNA in vertebrate cell genome," *In: Gene Transfer*, Kucherlapati (ed.), Plenum Press, New York, pp. 149–188, 1986.

Thiede, Bayerdorffer, Blasczyk, Wittig, Neubauer, "Simple and sensitive detection of mutations in the ras proto-oncogenes using PNA-mediated PCR™ clamping," *Nucl. Acids Res.*, 24(5):983–984, 1996.

Top et al., "Immunization with live types 7 and 4 adenovirus vaccines. II. Antibody response and protective effect against acute respiratory disease due to adenovirus type 7," *J. Infect. Dis.*, 124:155–160, 1971.

Truong-Le, August, Leong, "Controlled gene delivery by DNA-gelatin nanopspheres," *Hum. Gene Ther.*, 9(12): 1709–1717, 1998.

Tur-Kaspa et al., "Use of electroporation to introduce biologically active foreign genes into primary rat hepatocytes," *Mol. Cell Biol.,* 6:716–718, 1986.

Van Cott, Lubon, Russell, Butler, Gwazdauskas, Knight, Drohan, Velander, "Phenotypic and genotypic stability of multiple lines of transgenic pigs expressing recombinant human protein C," *Transgenic Res.,* 6(3):203–212, 1997.

Vanbever, Fouchard, Jadoul, De Morre, Preat, Marty, "In vivo noninvasive evaluation of hairless rat skin after high-voltage pulse exposure," *Skin Parmacol. Appl. Skin Physiol.,* 11(1):23–34, 1998.

Varmus et al., "Retroviruses as mutagens: Insertion and excision of a nontransforming provirus alter the expression of a resident transforming provirus," *Cell,* 25:23–36, 1981.

Vasanthakumar and Ahmed, "Modulation of drug resistance in a daunorubicin resistant subline with oligonucleoside methylphosphonates," *Cancer Commun.,* 1(4):225–232, 1989.

Veselkov, Demidov, Frank-Kamenetskii, Nielsen, "PNA as a rare genome-cutter," *Nature,* 379(6562):214, 1996.

Vickers, Griffith, Ramasamy, Risen, Freier, "Inhibition of NF-kappa B specific transcriptional activation by PNA strand invasion," *Nucl. Acids Res.,* 23(15):3003–3008, 1995.

Wagner, Zatloukal, Cotten, Kirlappos, Mechtler, Curiel, Birnstiel, "Coupling of adenovirus to transferrin-polylysine/DNA complexes greatly enhances receptor-mediated gene delivery and expression of transfected genes," *Proc. Natl. Acad. Sci. USA,* 89(13):6099–6103, 1992.

Wagner, Matteucci, Lewis, Gutierrez, Moulds, Froehler, "Antisense gene inhibition by oligonucleotides containing C-5 propyne pyrimidines," *Science,* 260(5113):1510–1513, 1993.

Watson, "Fluid and electrolyte disorders in cardiovascular patients," *Nurs. Clin. North Am.,* 22(4):797–803, 1987.

Webb, Toth, Poehlman, "Influence of physiological factors on the age-related increase in blood pressure in healthy men," *Exp. Gerontol.,* 31(3):341–350, 1996.

Wielbo, Senia, Gyurko, Phillips, "Antisense inhibition of hypertension in the spontaneously hypertensive rat," *Hypertension,* 25(3):314–319, 1994.

Wielbo, Simon, Phillips, Toffolo, "Inhibition of hypertension by peripheral administration of antisense oligodeoxynucleotides," *Hypertension,* 28(1):147–151, 1995.

Wielbo, Simon, Phillips, Toffolo, "Inhibition of hypertension by peripheral administration of antisense oligodeoxynucleotides," *Hypertension,* 28(1):147–151, 1996.

Wieblo, Shi, Sernia, "Antisense inhibition of angiotensinogen in hepatoma cell culture is enhanced by cationic liposome delivery," *Biochem. Biophy. Research Comm.,* 232:794–799, 1997.

Wong and Neumann, "Electric field mediated gene transfer," *Biochim. Biophys. Res. Commun.,* 107(2):584–587, 1982.

Wong et al., "Appearance of β-lactamase activity in animal cells upon liposome mediated gene transfer," *Gene,* 10:87–94, 1980.

Wu and Dean, "Functional significance of loops in the receptor binding domain of *Bacillus thuringiensis* CryIIIA delta-endotoxin," *J. Mol. Biol.,* 255(4):628–640, 1996.

Wu and Wu, "Receptor-mediated in vitro gene transfections by a soluble DNA carrier system," *J. Biol. Chem.,* 262:4429–4432, 1987.

Wu and Wu, "Evidence for targeted gene delivery to HepG2 hepatoma cells in vitro," *Biochemistry,* 27:887–892, 1988.

Wu and Wu, *Adv. Drug Delivery Rev.,* 12:159–167, 1993.

Yang, "Myocardial angiotensin II receptor expression and ischemia reperfusion injury," *Circ. Res.,* 1998.

Yang et al., "In vivo and in vitro gene transfer to mammalian somatic cells by particle bombardment," *Proc. Natl. Acad. Sci. USA,* 87:9568–9572, 1990.

Yang, Zhang, Davey, Mulligan, Cocking, *Plant Cell Rep,* 7:421–425, 1988.

Zambaux, Bonneaux, Gref, Maincent, Dellacherie, Alonso, Labrude, Vigneron, "Influence of experimental paparmeters on the characteristics of poly(lactic acid) nanoparticles prepared by a double emulsion method," *J. Controlled Release,* 50(1–3):31–40, 1998.

Zelenin et al., "High-velocity mechanical DNA transfer of the chloramphenicol acetyltransferase gene into rodent liver, kidney and mammary gland cells in organ explants and in vivo," *FEBS Lett.,* 280:94–96, 1991.

zur Muhlen, Schwarz, Mehnert, "Solid lipid nanoparticles (SLN) for controlled drug delivery—drug release and release mechanism," *Eur. J. Pharm. Biopharm.,* 45(2):149–155, 1998.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. An antisense oligonucleotide:
   (a) 9 to 35 nucleotides in length, said oligonucleotide comprising an at least 9 contiguous base sequence selected from the group consisting of SEQ ID NO:2, SEQ ID NO:3, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; or
   (b) 12 to 35 nucleotides in length, said oligonucleotide comprising an at least 12 contiguous base sequence selected from SEQ ID NO:4.

2. The antisense oligonucleotide of claim 1, wherein said oligonucleotide is 12 to 35 nucleotides in length.

3. The antisense oligonucleotide of claim 2, wherein said oligonucleotide is 12 to 30 nucleotides in length.

4. The antisense oligonucleotide of claim 3, wherein said oligonucleotide is 12 to 20 nucleotides in length.

5. The antisense oligonucleotide of claim 1, wherein said oligonucleotide comprises:
   (a) an at least 10 contiguous base sequence selected from the group consisting of SEQ ID NO:2, SEQ ID NO:3, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; or
   (b) an at least 13 contiguous base sequence selected from SEQ ID NO:4.

6. The antisense oligonucleotide of claim 5, wherein said oligonucleotide comprises an at least 12 contiguous base sequence selected from the group consisting of SEQ ID NO:2, SEQ ID NO:3, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

7. The antisense oligonucleotide of claim 6, wherein said oligonucleotide comprises an at least 14 contiguous base sequence selected from the group consisting of SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

8. The antisense oligonucleotide of claim 7, wherein said oligonucleotide comprises:
   (a) the sequence of SEQ ID NO:2, SEQ ID NO:3, SEQ ID NO:4, or SEQ ID NO:5; or
   (b) an at least 15 contiguous nucleotide sequence from SEQ ID NO:7, SEQ ID NO:8, SEQ ID NO:9, SEQ ID NO:10, SEQ ID NO: 11, SEQ ID NO: 12, SEQ ID NO: 13, SEQ ID NO:14, SEQ ID NO:15, SEQ ID NO:16, or SEQ ID NO:17.

9. The antisense oligonucleotide of claim 8, wherein said oligonucleotide comprises an at least 20 contiguous nucleotide sequence from SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

10. The antisense oligonucleotide of claim 9, wherein said oligonucleotide comprises the sequence of SEQ ID NO:9, SEQ ID NO:12, or SEQ ID NO:13.

11. The antisense oligonucleotide of claim 9, wherein said oligonucleotide comprises an at least 30 contiguous nucleotide sequence from SEQ ID NO:7, SEQ ID NO:8, SEQ ID NO:10, SEQ ID NO:11, SEQ ID NO:13, SEQ ID NO:14, SEQ ID NO:15, SEQ ID NO:16, or SEQ ID NO:17.

12. The antisense oligonucleotide of claim 11, wherein said oligonucleotide comprises the sequence of SEQ ID NO:13, SEQ ID NO:14, or SEQ ID NO:17.

13. The antisense oligonucleotide of claim 11, wherein said oligonucleotide comprises the sequence of SEQ ID NO:7, SEQ ID NO:8, SEQ ID NO:10, SEQ ID NO:11, SEQ ID NO:15, or SEQ ID NO:16.

14. The antisense oligonucleotide of claim 1, wherein said oligonucleotide is complementary to a sequence region of a gene encoding a mammalian angiotensin converting enzyme polypeptide.

15. The antisense oligonucleotide of claim 1, wherein said oligonucleotide spcifically binds to an mRNA expressed from the coding region of a gene encoding a mammalian angiotensin converting enzyme polypeptide, and further wherein binding of said oligonucleotide to said mRNA is effective in altering transcription of said mRNA in a host cell expressing said mRNA.

16. The antisense oligonucleotide of claim 15, wherein said host cell is a human cell.

17. The antisense oligonucleotide of claim 1, wherein said oligonucleotide comprises deoxyribonucleic acid, peptide nucleic acid, ribonucleic acid or derivatized ribonucleic acid.

18. The antisense oligonucleotide of claim 17, wherein said derivatized ribonucleic acid comprises a phosphorothioate, or a $C_{1-4}$ alkylphosphonate derivative.

19. The antisense oligonucleotide of claim 18, wherein said $C_{1-4}$ alkylphosphonate derivative is a methylphosphonate derivative.

20. The antisense oligonucleotide of claim 17, wherein said derivatized ribonucleic acid comprises a 3' or 5' acridine substitution.

21. An antisense oligonucleotide:
    (a) 9 to 30 nucleotides in length, said oligonucleotide comprising an at least 9 contiguous base sequence selected from the group consisting of SEQ ID NO:2, SEQ ID NO:3, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; or
    (b) 12 to 30 nucleotides in length, said oligonucleotide comprising an at least 12 contiguous base sequence selected from SEQ ID NO:4.

22. An antisense oligonucleotide:
    (a) 9 to 25 nucleotides in length, said oligonucleotide comprising an at least 9 contiguous base sequence selected from the group consisting of SEQ ID NO:2, SEQ ID NO:3, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17; or
    (b) 12 to 25 nucleotides in length, said oligonucleotide comprising an at least 12 contiguous base sequence selected from SEQ ID NO:4.

23. An antisense oligonucleotide:
    (a) 9 to 20 nucleotides in length, said oligonucleotide comprising an at least 9 contiguous base sequence selected from the group consisting of SEQ ID NO:2, SEQ ID NO:3, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO: 17; or
    (b) 12 to 20 nucleotides in length, said oligonucleotide comprising an at least 12 contiguous base sequence selected from SEQ ID NO:4.

24. An antisense oligonucleotide having no more than a two basepair mismatch from any one of the sequences of SEQ ID NO:2, SEQ ID NO:3, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

25. The antisense oligonucleotide of claim 24, said oligonucleotide having no more than a one basepair mismatch from any one of the sequences of SEQ ID NO:2, SEQ ID NO:3, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

26. An antisense oligonucleotide consisting of the sequence of SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

27. A recombinant vector comprising a nucleic acid segment that consists of the sequence of SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

28. A virus or viral vector comprising a nucleic acid segment that consists of the sequence of SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

29. A host cell comprising the recombinant vector of claim 27, or the virus or viral vector of claim 28.

30. A composition comprising: (a) the antisense oligonucleotide of claim 1, (b) the recombinant vector of claim 27, (c) the virus or viral vector of claim 28, or (d) the host cell of claim 29; and a pharmaceutical excipient.

31. An oligonucleotide of the formula:

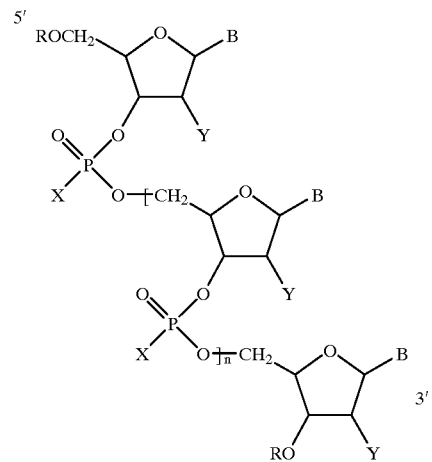

or a pharmaceutically-acceptable salt or hydrate thereof, wherein:
    each X is independently O, S, or $C_{1-4}$ alkyl;
    each R is independently selected from the group consisting of H, $C_{1-4}$ alkyl and $PO_2$-substituted acridine;
    each Y is independently H or OH;
    n is 7 to 33;
    each B is independently selected from the group consisting of adenine, guanine, cytosine or thymine;
    wherein B is selected such that the base sequence of said oligonucleotide comprises:
        (a) a sequence of at least 9 contiguous nucleotides from SEQ ID NO:2, SEQ ID NO:3, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17; or
        (b) a sequence of at least 12 contiguous base sequence selected from SEQ ID NO:4;
    and further wherein said oligonucleotide binds to a mRNA encoding a human angiotensin converting enzyme polypeptide and inhibits the translation thereof.

32. The compound of claim 31, in which B is selected such that the base sequence of said oligonucleotide comprises a sequence of at least 11 contiguous nucleotides from SEQ ID NO:2, SEQ ID NO:3, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

33. The compound of claim 32, in which B is selected such that the base sequence of said oligonucleotide comprises a sequence of at least 13 contiguous nucleotides from SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

34. The compound of claim 33, in which B is selected such that the base sequence of said oligonucleotide comprises a sequence of at least 14 contiguous nucleotides from SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

35. The compound of claim 31, in which B is selected such that the base sequence of said oligonucleotide comprises a sequence of at least 13 contiguous nucleotides from SEQ ID NO:4.

36. The compound of claim 31, in which B is selected such that the base sequence of said oligonucleotide comprises a sequence of at least 14 contiguous nucleotides from SEQ ID NO:4.

37. An oligonucleotide of the formula:

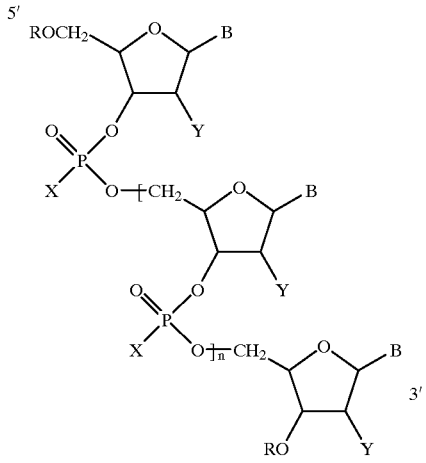

or a pharmaceutically-acceptable salt or hydrate thereof, wherein:
each X is independently O, S, or $C_{1-4}$alkyl;
each R is independently selected from the group consisting of H, $C_{1-4}$ alkyl and $PO_2$-substituted acridine;
each Y is independently H or OH;
n is 7 to 43;
each B is independently selected from the group consisting of adenine, guanine, cytosine or thymine;
wherein B is selected such that the base sequence of said oligonucleotide comprises the sequence of SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO: 17; and further wherein said oligonucleotide binds to a mRNA encoding a human angiotensin converting enzyme polypeptide and inhibits the translation thereof.

38. The compound of claim 37, wherein B is selected such that the base sequence of said oligonucleotide consists of the sequence of SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

39. A composition comprising the compound of claim 31 or claim 37.

40. The composition of claim 39, further comprising a pharmaceutical excipient.

41. The composition of claim further comprising a liposome, a lipid particle, a lipid vesicle, a nanoparticle, a microparticle, a nanocapsule, a nanosphere or a sphingosome.

42. The composition of claim 38, further comprising at least a first anti-hypertensive agent.

43. The composition of claim 42, wherein said anti-hypertensive agent is selected from the group consisting of captopril, enalapril, ramipril, cilazapril, fosinopril and lisinopril.

44. The composition of claim 39, further comprising a second oligonucleotide of at least 9 to about 35 nucleotides in length, wherein said second oligonucleotide specifically binds to a portion of an mRNA that encodes an angiotensin converting enzyme polypeptide, a β-1 adrenoceptor polypeptide, or an AT-1 angiotensin receptor polypeptide.

45. The composition of claim 39, further comprising a second oligonucleotide of at least 9 to about 35 nucleotides in length, wherein said second oligonucleotide specifically binds to a portion of an mRNA that encodes a renin, angiotensin, or angiotensinogen polypeptide.

46. A kit comprising:
(a) the compound of claim 31,
(b) the compound of claim 37, or
(c) a composition comprising:
(1) the antisense oligonucleotide of claim 1,
(2) the recombinant vector of claim 27,
(3) the virus or viral vector of claim 28; or
the host cell of claim 29; and
instructions for using said kit.

47. The kit of claim 46, further comprising a device for delivering said compound or said composition to a mammalian lung.

48. A method for reducing the expression of a gene encoding mammalian angiotensin converting enzyme in a host cell, said method comprising contacting said host cell with an amount of:
(a) a composition comprising:
the antisense oligonucleotide of claim 1; or
(b) the oligonucleotide of claim 31 or claim 37 effective to reduce expression of said enzyme in said cell.

49. A method for reducing the activity of angiotensin converting enzyme in a host cell, said method comprising contacting said host cell with an amount of:
(a) a composition comprising:
the antisense oligonucleotide of claim 1; or
(b) the oligonucleotide of claim 31 or claim 37, effective to reduce the activity of said enzyme in a cell.

50. A method for reducing blood pressure in a mammal comprising administering to said mammal a therapeutically effective amount of:
(a) a composition comprising:
the antisense oligonucleotide of claim 1; or
(b) the oligonucleotide of claim 31 or claim 37, to reduce blood pressure in said mammal.

51. A method for treating hypertension in a mammal comprising administering to said mammal a therapeutically effective amount of:

(a) a composition comprising:
  the antisense oligonucleotide of claim 1; or
(b) the oligonucleotide of claim 31 or claim 37, to treat hypertension in said mammal.

52. The method of claim 48, said method comprising contacting said host cell with an effective amount of the antisense oligonucleotide of claim 1 to reduce expression of said enzyme in said cell.

53. The method of claim 48, said method comprising contacting said host cell with an effective amount of the oligonucleotide of claim 31 or 37 to reduce expression of said enzyme in said cell.

54. The method of claim 49, said method comprising contacting said host cell with an effective amount of the antisense oligonucleotide of claim 1 to reduce activity of said enzyme in said cell.

55. The method of claim 49, said method comprising contacting said host cell with an effective amount of the oligonucleotide of claim 31 or 37 to reduce activity of said enzyme in said cell.

56. The method of claim 50, said method comprising administering to said mammal an effective amount of the antisense oligonucleotide of claim 1 to reduce blood pressure in said mammal.

57. The method of claim 50, said method comprising contacting a host cell with an effective amount of the compound of claim 31 or claim 37 to treat hypertension in said mammal.

58. The method of claim 51, said method comprising administering to said mammal an effective amount of the antisense oligonucleotide of claim 1 to treat hypertension in said mammal.

59. The method of claim 51, said method comprising contacting a host cell with an effective amount of the compound of claim 31 or claim 37 to treat hypertension in said mammal.

* * * * *